United States Patent
Kwan et al.

(10) Patent No.: US 10,849,893 B2
(45) Date of Patent: Dec. 1, 2020

(54) THERAPEUTIC COMBINATIONS OF ORALLY ADMINISTERED DOCETAXEL AND A P-GP INHIBITOR FOR THE TREATMENT OF CANCER

(71) Applicant: Athenex HK Innovative Limited, Sha Tin (HK)

(72) Inventors: Min-Fun Rudolf Kwan, Summit, NJ (US); E. Douglas Kramer, Stamford, CT (US); David Lawrence Cutler, Moorestown, NJ (US); Johnson Yiu-Nam Lau, Houston, TX (US); Wing Kai Chan, Hong Kong (CN)

(73) Assignee: Athenex HK Innovative Limited, Sha Tin (HK)

( * ) Notice: Subject to any disclaimer, the term of this patent is extended or adjusted under 35 U.S.C. 154(b) by 0 days.

(21) Appl. No.: 16/715,735

(22) Filed: Dec. 16, 2019

(65) Prior Publication Data

US 2020/0188386 A1    Jun. 18, 2020

Related U.S. Application Data

(60) Provisional application No. 62/846,869, filed on May 13, 2019, provisional application No. 62/779,742, filed on Dec. 14, 2018.

(51) Int. Cl.
| | | |
|---|---|---|
| *A61K 31/4725* | (2006.01) | |
| *A61K 31/337* | (2006.01) | |
| *A61K 9/00* | (2006.01) | |
| *A61P 35/00* | (2006.01) | |

(52) U.S. Cl.
CPC ........ *A61K 31/4725* (2013.01); *A61K 9/0019* (2013.01); *A61K 9/0053* (2013.01); *A61K 31/337* (2013.01); *A61P 35/00* (2018.01)

(58) Field of Classification Search
CPC .............. A61K 31/4725; A61K 9/0019; A61K 9/0053; A61K 31/337; A61P 35/00
USPC ........................................................ 514/382
See application file for complete search history.

(56) References Cited

U.S. PATENT DOCUMENTS

2015/0272943 A1    10/2015 Kim et al.

FOREIGN PATENT DOCUMENTS

| WO | WO 2005/033097 A1 | 4/2005 |
| WO | WO 2017/054754 A1 | 4/2017 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Braakhuis et al. "In Vitro Antiproliferative Activity of Docetaxel (Taxotere®), Paclitaxel (Taxol®) and Cisplatin against Human Tumour and Normal Bone Marrow Cells", *Anticancer Research* (1994), vol. 14, p. 205-208.
Engblom et al. "Taxane Sensitivity of Ovarian Carcinoma in Vitro", *Anticancer Research* (1997), vol. 17, p. 2475-2480.
Kelland et al. "Comparative in vitro cytotoxicity of taxol and Taxotere against cisplatin-sensitive and -resistant human ovarian carcinoma cell lines", *Cancer Chemotherapy and Pharmacology* (1992), vol. 30, p. 444-450.
Riccardi et al. "Cytotoxicity of Paclitaxel and Docetaxel in Human Neuroblastoma Cell Lines", *Eur J of Cancer* (1995), vol. 31A, No. 4, p. 494-499.

* cited by examiner

*Primary Examiner* — Kristin A Vajda
(74) *Attorney, Agent, or Firm* — Cooley LLP; Heidi A. Erlacher; Chen Chen

(57) ABSTRACT

The present disclosure provides pharmaceutical combinations of orally administered docetaxel and a P-gp inhibitor. The pharmaceutical combinations are suitable for the treatment of cancer in a subject and for reducing or preventing toxicity, hypersensitivity-type infusion reactions, and other negative outcomes resulting from or associated with intravenously administered docetaxel (e.g., Taxotere® or docetaxel formulated with polysorbate 80) therapy in a subject suffering from cancer.

32 Claims, 12 Drawing Sheets

THERAPEUTIC COMBINATIONS OF ORALLY ADMINISTERED DOCETAXEL AND A P-GP INHIBITOR FOR THE TREATMENT OF CANCER

RELATED APPLICATIONS

This application claims priority to, and the benefit of, U.S. Provisional Application No. 62/779,742, filed on Dec. 14, 2018, and 62/846,869, filed on May 13, 2019, the contents of each of which are incorporated herein in their entirety.

BACKGROUND

Docetaxel (Taxotere®) was approved for medical use in 1995 and marketed under the brand name Taxotere®. Docetaxel stabilizes microtubules in the cell, thereby interfering with the normal breakdown of microtubules during mitosis. Docetaxel is indicated to treat many types of cancer, including lung, ovarian, and breast. However, the affinity of docetaxel for the p-glycoprotein pump (P-gp) leads to efflux of docetaxel back into the intestinal lumen, thus making the drug non-bioavailable when taken orally. Its poor absorption through the intestinal epithelium, along with its unfavorable solubility, has necessitated intravenous administration of docetaxel. Excipients, such as polysorbate 80 (Tween 80®), used for intravenous administration of docetaxel often cause tolerability problems such as hypersensitivity-type infusion reactions. Intravenously administered docetaxel (e.g., Taxotere® or docetaxel formulated with polysorbate 80) requires premedication which has its own set of side effects. Further, intravenously administered docetaxel may also be associated with increased incidence or severity of neurotoxicity.

Therefore, an effective therapeutic regimen including an oral formulation of docetaxel along with oral administration of a P-gp inhibitor may be beneficial, and may be expected to improve the treatment outcomes of cancer. By inhibiting the efflux of docetaxel by P-gp back to the intestinal lumen, oral administration would allow therapeutically relevant concentrations of the drug that are now efficacious and also would avoid the use of excipients such as polysorbate 80, thus leading to a wide therapeutic window that will promote antitumor response while mitigating or avoiding the reactions and toxicities associated directly with the drug or the excipients. In addition, oral administration of docetaxel provides a more convenient and safe method. The present disclosure addresses the needs for orally administering docetaxel.

SUMMARY

In some aspects, the present disclosure provides, at least in part, methods for treating a disease or disorder, such as cancer, or reducing or preventing toxicity, hypersensitivity-type infusion reactions and/or other negative outcomes (e.g., skin toxicity, nausea, vomiting, diarrhea, fatigue, sensory neuropathy, and infection) resulting from or associated with intravenously administered docetaxel (e.g., Taxotere® or docetaxel formulated with polysorbate 80) therapy in a subject.

In some aspects, the present disclosure provides a compound for use in the treatment of a disease or disorder in a subject in need thereof, wherein the compound is Compound A:

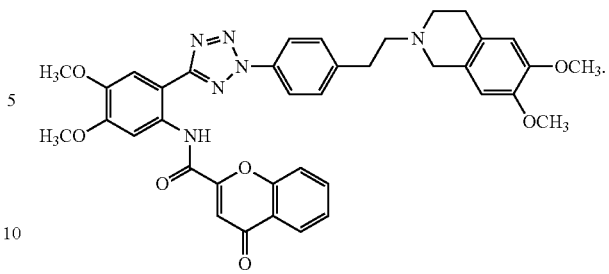

In some aspects, the present disclosure provides Compound A for use in the treatment of cancer in a subject in need thereof.

In some aspects, the present disclosure provides Compound A for use in reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides Compound A for use in reducing or preventing hypersensitivity-type infusion reactions associated with intravenously administered docetaxel (e.g., Taxotere® or docetaxel formulated with polysorbate 80) therapy in a subject in need thereof.

In some aspects, the present disclosure provides a method for treating a disease or disorder in a subject in need thereof, comprising:
  a. oral administration of docetaxel at an amount of about 15 mg/m$^2$ to about 450 mg/m$^2$ to the subject once a day and for 1-7 times a week; and
  b. oral administration of Compound A to the subject once a day and for 1-7 times a week, wherein Compound A is administered simultaneously with or prior to the docetaxel.

In some aspects, the present disclosure provides a method for treating cancer in a subject in need thereof, comprising:
  a. oral administration of docetaxel at an amount of about 15 mg/m$^2$ to about 450 mg/m$^2$ to the subject once a day and for 1-7 times a week; and
  b. oral administration of Compound A to the subject once a day and for 1-7 times a week, wherein Compound A is administered simultaneously with or prior to the docetaxel.

In some aspects, the present disclosure provides a method for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof, comprising:
  a. oral administration of docetaxel at an amount of about 15 mg/m$^2$ to about 450 mg/m$^2$ to the subject once a day and for 1-7 times a week; and
  b. oral administration of Compound A to the subject once a day and for 1-7 times a week, wherein Compound A is administered simultaneously with or prior to the docetaxel.

In some aspects, the present disclosure provides a method for reducing or preventing hypersensitivity-type infusion reactions associated with intravenously administered docetaxel (e.g., Taxotere® or docetaxel formulated with polysorbate 80) therapy in a subject in need thereof, comprising:
  a. oral administration of docetaxel at an amount of about 15 mg/m$^2$ to about 450 mg/m$^2$ to the subject once a day and for 1-7 times a week; and
  b. oral administration of Compound A to the subject once a day and for 1-7 times a week, wherein Compound A is administered simultaneously with or prior to the docetaxel.

In some aspects, the present disclosure provides use of oral docetaxel in combination with Compound A in treating a disease or disorder in a subject in need thereof.

In some aspects, the present disclosure provides use of oral docetaxel in combination with Compound A in treating cancer in a subject in need thereof.

In some aspects, the present disclosure provides use of oral docetaxel in combination with Compound A in reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides use of oral docetaxel in combination with Compound A in reducing or preventing hypersensitivity-type infusion reactions associated with intravenously administered docetaxel (e.g., Taxotere® or docetaxel formulated with polysorbate 80) therapy in a subject in need thereof.

In some aspects, the present disclosure provides docetaxel for oral administration for use in combination with Compound A in treating a disease or disorder in a subject in need thereof.

In some aspects, the present disclosure provides docetaxel for oral administration for use in combination with Compound A in treating cancer in a subject in need thereof.

In some aspects, the present disclosure provides docetaxel for oral administration for use in combination with Compound A in reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides docetaxel for oral administration for use in combination with Compound A in reducing or preventing hypersensitivity-type infusion reactions associated with intravenously administered docetaxel (e.g., Taxotere® or docetaxel formulated with polysorbate 80) therapy in a subject in need thereof.

In some aspects, the present disclosure provides the use of docetaxel in combination with Compound A in the manufacture of a medicament for treating a disease or disorder in a subject in need thereof.

In some aspects, the present disclosure provides the use of docetaxel in combination with Compound A in the manufacture of a medicament for treating cancer in a subject in need thereof.

In some aspects, the present disclosure provides the use of docetaxel in combination with Compound A in the manufacture of a medicament for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides the use of docetaxel in combination with Compound A in the manufacture of a medicament for reducing or preventing hypersensitivity-type infusion reactions associated with intravenously administered docetaxel (e.g., Taxotere® or docetaxel formulated with polysorbate 80) therapy in a subject in need thereof.

In some aspects, the present disclosure provides the use of docetaxel for oral administration in combination with Compound A in the manufacture of a medicament for treating a disease or disorder in a subject in need thereof.

In some aspects, the present disclosure provides the use of docetaxel for oral administration in combination with Compound A in the manufacture of a medicament for treating cancer in a subject in need thereof.

In some aspects, the present disclosure provides the use of docetaxel for oral administration in combination with Compound A in the manufacture of a medicament for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides the use of docetaxel for oral administration in combination with Compound A in the manufacture of a medicament for reducing or preventing hypersensitivity-type infusion reactions associated with intravenously administered docetaxel (e.g., Taxotere® or docetaxel formulated with polysorbate 80) therapy in a subject in need thereof.

In some aspects, the present disclosure provides docetaxel for use with Compound A in a combinational therapy for treating a disease or disorder in a subject in need thereof.

In some aspects, the present disclosure provides docetaxel for use with Compound A in a combinational therapy for treating cancer in a subject in need thereof.

In some aspects, the present disclosure provides docetaxel for use with Compound A in a combinational therapy for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides docetaxel for use with Compound A in a combinational therapy for reducing or preventing hypersensitivity-type infusion reactions associated with intravenously administered docetaxel (e.g., Taxotere® or docetaxel formulated with polysorbate 80) therapy in a subject in need thereof.

In some aspects, the present disclosure provides Compound A for use in a combination therapy with docetaxel in the treatment of a disease or disorder in a subject in need thereof.

In some aspects, the present disclosure provides Compound A for use in a combination therapy with docetaxel in the treatment of cancer in a subject in need thereof.

In some aspects, the present disclosure provides Compound A for use in a combination therapy with docetaxel in reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides Compound A for use in a combination therapy with docetaxel in reducing or preventing hypersensitivity-type infusion reactions associated with intravenously administered docetaxel (e.g., Taxotere® or docetaxel formulated with polysorbate 80) therapy in a subject in need thereof.

In some aspects, the present disclosure provides use of Compound A in the manufacture of a medicament for use in combination with docetaxel in treating a disease or disorder in a subject in need thereof.

In some aspects, the present disclosure provides use of Compound A in the manufacture of a medicament for use in combination with docetaxel in treating cancer in a subject in need thereof.

In some aspects, the present disclosure provides use of Compound A in the manufacture of a medicament for use in combination with docetaxel in reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides use of Compound A in the manufacture of a medicament for use in combination with docetaxel in reducing or preventing hypersensitivity-type infusion reactions associated with intravenously administered docetaxel (e.g., Taxotere® or docetaxel formulated with polysorbate 80) therapy in a subject in need thereof.

In some aspects, the present disclosure provides a medicament for use in a combination therapy with docetaxel in the treatment of a disease or disorder in a subject in need thereof, wherein the medicament comprises Compound A.

In some aspects, the present disclosure provides a medicament for use in a combination therapy with docetaxel in the treatment of cancer in a subject in need thereof, wherein the medicament comprises Compound A.

In some aspects, the present disclosure provides a medicament for use in a combination therapy with docetaxel for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof, wherein the medicament comprises Compound A.

In some aspects, the present disclosure provides a medicament for use in a combination therapy with docetaxel for reducing or preventing hypersensitivity-type infusion reactions associated with intravenously administered docetaxel (e.g., Taxotere® or docetaxel formulated with polysorbate 80) therapy in a subject in need thereof, wherein the medicament comprises Compound A.

In some aspects, the present disclosure provides a medicament for use in a combination therapy with Compound A in the treatment of a disease or disorder in a subject in need thereof, wherein the medicament comprises docetaxel.

In some aspects, the present disclosure provides a medicament for use in a combination therapy with Compound A in the treatment of cancer in a subject in need thereof, wherein the medicament comprises docetaxel.

In some aspects, the present disclosure provides a medicament for use in a combination therapy with Compound A for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof, wherein the medicament comprises docetaxel.

In some aspects, the present disclosure provides a medicament for use in a combination therapy with Compound A for reducing or preventing hypersensitivity-type infusion reactions associated with intravenously administered docetaxel (e.g., Taxotere® or docetaxel formulated with polysorbate 80) therapy in a subject in need thereof, wherein the medicament comprises docetaxel.

In some aspects, the present disclosure provides use of Compound A in a combination therapy with docetaxel in the treatment of a disease or disorder in a subject in need thereof.

In some aspects, the present disclosure provides use of Compound A in a combination therapy with docetaxel in the treatment of cancer in a subject in need thereof.

In some aspects, the present disclosure provides use of Compound A in a combination therapy with docetaxel for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides use of Compound A in a combination therapy with docetaxel for reducing or preventing hypersensitivity-type infusion reactions associated with intravenously administered docetaxel (e.g., Taxotere® or docetaxel formulated with polysorbate 80) therapy in a subject in need thereof.

In some aspects, the present disclosure provides a pharmaceutical combination of docetaxel and Compound A.

In some aspects, the methods, compounds (i.e., Compound A or docetaxel) for use, use (i.e., use of Compound A or docetaxel), medicament, manufacture of medicament, medicament for use, combination, or combination therapy, or the like, described herein, comprises administering orally or oral administration of Compound A, according to the dosage and/or dosing regimen described herein (e.g., once a day and for 1-7 times a week).

In some aspects, the methods, compounds (i.e., Compound A or docetaxel) for use, use (i.e., use of Compound A or docetaxel), medicament, manufacture of medicament, medicament for use, combination, or combination therapy, or the like, described herein, comprises administering orally or oral administration of docetaxel, according to the dosage and/or dosing regimen described herein (e.g., at an amount of about 15 mg/m$^2$ to about 450 mg/m$^2$ to the subject once a day and for 1-7 times a week).

In some aspects, the methods, compounds (i.e., Compound A or docetaxel) for use, use (i.e., use of Compound A or docetaxel), medicament, manufacture of medicament, medicament for use, combination, or combination therapy, or the like, described herein, comprises administering orally or oral administration of Compound A, according to the dosage and/or dosing regimen described herein (e.g., once a day and for 1-7 times a week), simultaneously with or prior to, administering orally or oral administration of docetaxel, according to the dosage and/or dosing regimen described herein (e.g., at an amount of about 15 mg/m$^2$ to about 450 mg/m$^2$ to the subject once a day and for 1-7 times a week).

In some aspects, in the methods, compounds (i.e., Compound A or docetaxel) for use, use (i.e., use of Compound A or docetaxel), medicament, manufacture of medicament, medicament for use, combination, or combination therapy, or the like, described herein, the subject is suffering from cancer and undergoing a docetaxel therapy.

In some aspects, in the methods, compounds (i.e., Compound A or docetaxel) for use, use (i.e., use of Compound A or docetaxel), medicament, manufacture of medicament, medicament for use, combination, or combination therapy, or the like, described herein, the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 30 mg/m$^2$ to 100 mg/m$^2$ over a period of about 1 hour to about 24 hours once every three weeks, once every two weeks, or once every week.

In some aspects, in the methods, compounds (i.e., Compound A or docetaxel) for use, use (i.e., use of Compound A or docetaxel), medicament, manufacture of medicament, medicament for use, combination, or combination therapy, or the like, described herein, the orally administered docetaxel reaches therapeutic blood or plasma levels in the subject.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the present disclosure. In the case of conflict, the present specification, including definitions, will control. In addition, the materials, methods, and examples are illustrative only and are not intended to be limiting.

Other features and advantages of the present disclosure will be apparent from the following detailed descriptions and claims.

DETAILED DESCRIPTION

Figure 1:
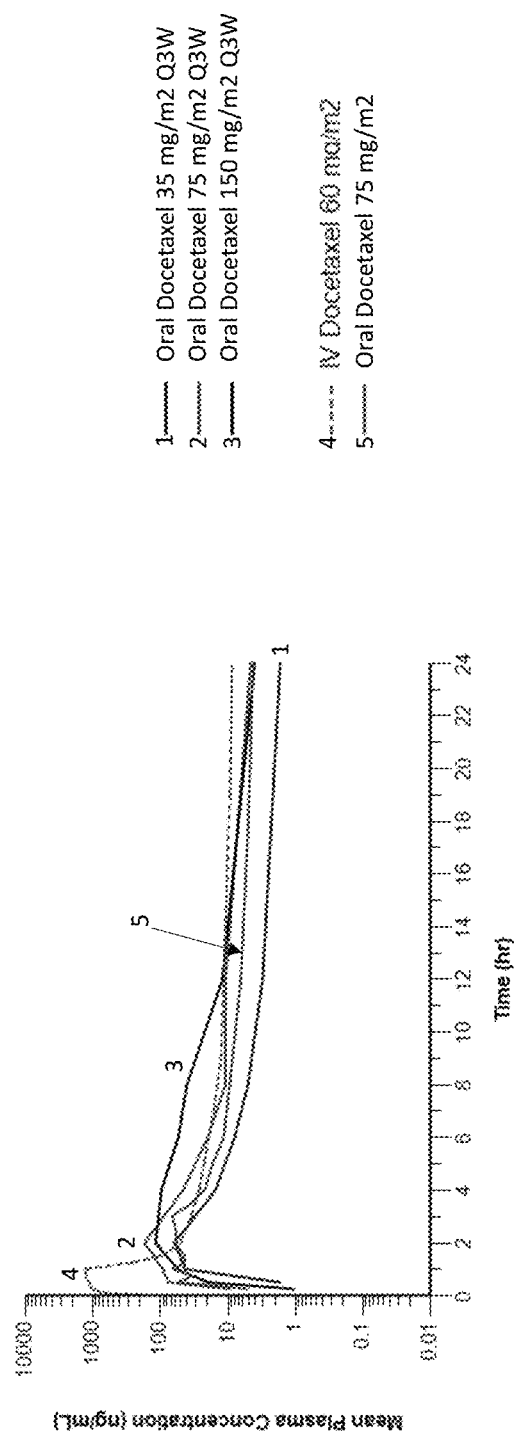
FIG. 1 is a graph showing the comparison of IV docetaxel and oral docetaxel (Mean Plasma Concentration (ng/mL) vs Time (hr)) from 0 to 24 hours.

In some embodiments, the present disclosure pertains, at least in part, to methods for treating cancer in a subject.

In some embodiments, the present disclosure pertains, at least in part, to methods for reducing or preventing toxicity, hypersensitivity-type infusion reactions, and other negative outcomes resulting from or associated with intravenously administered docetaxel (e.g., Taxotere® or docetaxel formulated with polysorbate 80) therapy in a subject suffering from cancer.

In some embodiments, the present disclosure provides a method for treating cancer in a subject in need thereof, comprising:
a. oral administration of docetaxel at an amount of about 15 mg/m$^2$ to about 450 mg/m$^2$ to the subject once a day and for 1-7 times a week; and
b. oral administration of Compound A:

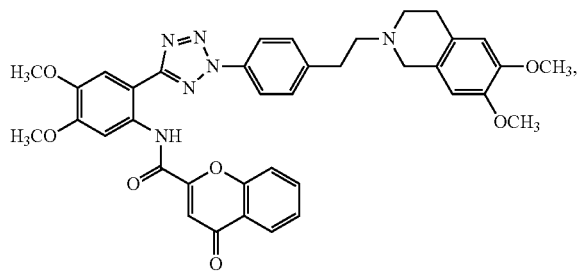 [SMILES: COc1cc2c(cc1OC)CN(CCc1ccc(-n3nnc(-c4cc(OC)c(OC)cc4NC(=O)c4cc(=O)c5ccccc5o4)n3)cc1)CC2]

to the subject once a day and for 1-7 times a week, wherein Compound A is administered simultaneously with or prior to the docetaxel.

In some embodiments, the present disclosure provides a method for reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing a docetaxel therapy, comprising:
a. oral administration of docetaxel at an amount of about 15 mg/m$^2$ to about 450 mg/m$^2$ to the subject once a day and for 1-7 times a week; and
b. oral administration of Compound A to the subject once a day and for 1-7 times a week, wherein the plasma exposure of the orally administered docetaxel, as measured by AUC$_{(0\rightarrow\infty)}$, is equal to or greater than the plasma exposure, as measured by AUC$_{(0\rightarrow\infty)}$, of intravenously administered docetaxel (e.g., Taxotere® or docetaxel formulated with polysorbate 80) at an amount of about 30 mg/m$^2$ to 100 mg/m$^2$ over a period of about 1 hour to about 24 hours once every three weeks, once every two weeks, or once every week, and wherein Compound A is administered simultaneously with or prior to the docetaxel.

In some embodiments, the present disclosure provides a method for reducing or preventing hypersensitivity-type infusion reactions associated with intravenously administered docetaxel (e.g., Taxotere® or docetaxel formulated with polysorbate 80) therapy in a subject in need thereof, comprising:
a. oral administration of docetaxel at an amount of about 15 mg/m$^2$ to about 450 mg/m$^2$ to the subject once a day and for 1-7 times a week; and
b. oral administration of Compound A to the subject once a day for 1-7 times a week, wherein Compound A is administered simultaneously with or prior to the docetaxel.

In some embodiments, the present disclosure pertains, at least in part, to Compound A for use with docetaxel in the treatment of cancer in a subject.

In some embodiments, the present disclosure pertains, at least in part, to Compound A for use with docetaxel in reducing or preventing toxicity, hypersensitivity-type infusion reactions, and other negative outcomes resulting from or associated with intravenously administered docetaxel (e.g., Taxotere® or docetaxel formulated with polysorbate 80) therapy in a subject suffering from cancer.

In some embodiments, the present disclosure provides Compound A for use with docetaxel in the treatment of cancer in a subject in need thereof, wherein the subject is administered docetaxel orally at an amount of about 15 mg/m² to about 450 mg/m² once a day and for 1-7 times a week;

wherein Compound A is administered to the subject once a day and for 1-7 times a week; and wherein Compound A is administered simultaneously with or prior to the docetaxel.

In some embodiments, the present disclosure provides Compound A for use with docetaxel in reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing docetaxel therapy, wherein the subject is administered docetaxel orally at an amount of about 15 mg/m² to about 450 mg/m² once a day and for 1-7 times a week;

wherein Compound A is administered to the subject once a day and for 1-7 times a week; and wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 30 mg/m² to 100 mg/m² over a period of about 1 to about 24 hours once every three weeks, once every two weeks, or once every week, and wherein Compound A is administered simultaneously with or prior to the docetaxel.

In some embodiments, the present disclosure provides Compound A for use with docetaxel in reducing or preventing hypersensitivity-type infusion reactions associated with intravenously administered docetaxel (e.g., Taxotere® or docetaxel formulated with polysorbate 80) therapy in a subject in need thereof, wherein the subject is administered docetaxel orally at an amount of about 15 mg/m² to about 450 mg/m² once a day and for 1-7 times a week;

wherein Compound A is administered to the subject once a day for 1-7 times a week; and
wherein Compound A is administered simultaneously with or prior to the docetaxel.

In some embodiments, the present disclosure pertains, at least in part, to the use of Compound A in the manufacture of a medicament for use with docetaxel in the treatment of cancer in a subject.

In some embodiments, the present disclosure pertains, at least in part, to the use of Compound A in the manufacture of a medicament for use with docetaxel in reducing or preventing toxicity, hypersensitivity-type infusion reactions, and other negative outcomes resulting from or associated with intravenously administered docetaxel (e.g., Taxotere® or docetaxel formulated with polysorbate 80) therapy in a subject suffering from cancer.

In some embodiments, the present disclosure provides the use of Compound A in the manufacture of a medicament for use with docetaxel in treating cancer in a subject in need thereof, wherein the subject is administered docetaxel orally at an amount of about 15 mg/m² to about 450 mg/m² once a day and for 1-7 times a week;

wherein Compound A is administered to the subject once a day and for 1-7 times a week; and wherein Compound A is administered simultaneously with or prior to the docetaxel.

In some embodiments, the present disclosure provides the use of Compound A in the manufacture of a medicament for use with docetaxel in reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing docetaxel therapy, wherein the subject is administered docetaxel orally at an amount of about 15 mg/m² to about 450 mg/m² once a day and for 1-7 times a week;

wherein Compound A is administered to the subject once a day and for 1-7 times a week; and wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel e.g., Taxotere® or docetaxel formulated with polysorbate 80) at an amount of about 30 mg/m² to 100 mg/m² over a period of about 1 to about 24 hours once every three weeks, once every two weeks, or once every week, and wherein Compound A is administered simultaneously with or prior to the docetaxel.

In some embodiments, the present disclosure provides the use of Compound A in the manufacture of a medicament for use with docetaxel in reducing or preventing hypersensitivity-type infusion reactions associated with intravenously administered docetaxel (e.g., Taxotere® or docetaxel formulated with polysorbate 80) therapy in a subject in need thereof, wherein the subject is administered docetaxel orally at an amount of about 15 mg/m² to about 450 mg/m² once a day and for 1-7 times a week;

wherein Compound A is administered to the subject once a day for 1-7 times a week; and
wherein Compound A is administered simultaneously with or prior to the docetaxel.

In some embodiments, the present disclosure pertains, at least in part, to use of Compound A with docetaxel in the treatment of cancer in a subject.

In some embodiments, the present disclosure pertains, at least in part, to use of Compound A with docetaxel in reducing or preventing toxicity, hypersensitivity-type infusion reactions, and other negative outcomes resulting from or associated with intravenously administered docetaxel (e.g., Taxotere® or docetaxel formulated with polysorbate 80) therapy in a subject suffering from cancer.

In some embodiments, the present disclosure provides use of Compound A with docetaxel in the treatment of cancer in a subject in need thereof, wherein the subject is administered docetaxel orally at an amount of about 15 mg/m² to about 450 mg/m² once a day and for 1-7 times a week;

wherein Compound A administered to the subject once a day and for 1-7 times a week; and wherein Compound A is administered simultaneously with or prior to the docetaxel.

In some embodiments, the present disclosure provides use of Compound A with docetaxel in reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing docetaxel therapy, wherein the subject is administered docetaxel orally at an amount of about 15 mg/m² to about 450 mg/m² once a day and for 1-7 times a week;

wherein Compound A is administered to the subject once a day and for 1-7 times a week; and wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 30 mg/m$^2$ to 100 mg/m$^2$ over a period of about 1 to about 24 hours once every three weeks, once every two weeks, or once every week, and wherein Compound A is administered simultaneously with or prior to the docetaxel.

In some embodiments, the present disclosure provides the use of Compound A with docetaxel in reducing or preventing hypersensitivity-type infusion reactions associated with intravenously administered docetaxel (e.g., Taxotere® or docetaxel formulated with polysorbate 80) therapy in a subject in need thereof, wherein the subject is administered docetaxel orally at an amount of about 15 mg/m$^2$ to about 450 mg/m$^2$ once a day and for 1-7 times a week;

wherein Compound A is administered to the subject once a day for 1-7 times a week; and wherein Compound A is administered simultaneously with or prior to the docetaxel.

In some embodiments, the present disclosure pertains, at least in part, to Compound A for use in a combination therapy with docetaxel in the treatment of cancer in a subject.

In some embodiments, the disclosure pertains, at least in part, to Compound A for use in a combination therapy with docetaxel in reducing or preventing toxicity, hypersensitivity-type infusion reactions, and other negative outcomes resulting from or associated with intravenously administered docetaxel (e.g., Taxotere® or docetaxel formulated with polysorbate 80) therapy in a subject suffering from cancer.

In some embodiments, the present disclosure provides Compound A for use in a combination therapy with docetaxel in the treatment of cancer in a subject in need thereof, wherein Compound A is administered to the subject once a day and for 1-7 times a week;

wherein the subject is also administered docetaxel orally at an amount of about 15 mg/m$^2$ to about 450 mg/m$^2$ once a day and for 1-7 times a week; and wherein Compound A is administered simultaneously with or prior to the docetaxel.

In some embodiments, the present disclosure provides Compound A for use in a combination therapy with docetaxel for reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing docetaxel therapy, wherein Compound A is administered to the subject once a day and for 1-7 times a week;

wherein the subject is also administered docetaxel orally at an amount of about 15 mg/m$^2$ to about 450 mg/m$^2$ once a day and for 1-7 times a week;

wherein the plasma exposure of the orally administered docetaxel, as measured by $AUC_{(0 \to \infty)}$, is equal to or greater than the plasma exposure, as measured by $AUC_{(0 \to \infty)}$, of intravenously administered docetaxel (e.g., Taxotere® or docetaxel formulated with polysorbate 80) at an amount of about 30 mg/m$^2$ to 100 mg/m$^2$ over a period of about 1 to about 24 hours once every three weeks, once every two weeks, or once every week; and wherein Compound A is administered simultaneously with or prior to the docetaxel.

In some embodiments, the present disclosure provides Compound A for use in a combination therapy with docetaxel for reducing or preventing hypersensitivity-type infusion reactions associated with intravenously administered docetaxel (e.g., Taxotere® or docetaxel formulated with polysorbate 80) therapy in a subject in need thereof, wherein the subject is administered docetaxel orally at an amount of about 15 mg/m$^2$ to about 450 mg/m$^2$ once a day and for 1-7 times a week;

wherein Compound A is administered to the subject once a day for 1-7 times a week; and wherein Compound A is administered simultaneously with or prior to the docetaxel.

In some embodiments, the disclosure pertains, at least in part, to a medicament comprising Compound A for use in a combination therapy with docetaxel in the treatment of cancer in a subject.

In some embodiments, the present disclosure pertains, at least in part, to a medicament comprising Compound A for use in a combination therapy with docetaxel in reducing or preventing toxicity, hypersensitivity-type infusion reactions, and other negative outcomes resulting from or associated with intravenously administered docetaxel (e.g., Taxotere® or docetaxel formulated with polysorbate 80) therapy in a subject suffering from cancer.

In some embodiments, the present disclosure provides a medicament comprising Compound A for use in a combination therapy with docetaxel in the treatment of cancer in a subject in need thereof, wherein the medicament is administered to the subject once a day and for 1-7 times a week;

wherein the subject is also administered docetaxel orally at an amount of about 15 mg/m$^2$ to about 450 mg/m$^2$ once a day and for 1-7 times a week; and wherein the medicament is administered simultaneously with or prior to the docetaxel.

In some embodiments, the present disclosure provides a medicament comprising Compound A for use in a combination therapy with docetaxel for reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing docetaxel therapy, wherein the medicament is administered to the subject once a day and for 1-7 times a week;

wherein the subject is also administered docetaxel orally at an amount of about 15 mg/m$^2$ to about 450 mg/m$^2$ once a day and for 1-7 times a week;

wherein the plasma exposure of the orally administered docetaxel, as measured by $AUC_{(0 \to \infty)}$, is equal to or greater than the plasma exposure, as measured by $AUC_{(0 \to \infty)}$, of intravenously administered docetaxel (e.g., Taxotere® or docetaxel formulated with polysorbate 80) at an amount of about 30 mg/m$^2$ to 100 mg/m$^2$ over a period of about 1 to about 24 hours once every three weeks, once every two weeks, or once every week; and wherein the medicament is administered simultaneously with or prior to the docetaxel.

In some embodiments, the present disclosure provides a medicament comprising Compound A in a combination therapy with docetaxel for reducing or preventing hypersensitivity-type infusion reactions associated with intravenously administered docetaxel (e.g., Taxotere® or docetaxel formulated with polysorbate 80) therapy in a subject in need thereof, wherein the medicament is administered to the subject once a day for 1-7 times a week; and wherein the subject is also administered docetaxel orally at an amount of about 15 mg/m$^2$ to about 450 mg/m$^2$ once a day and for 1-7 times a week;

wherein the medicament administered simultaneously with or prior to the docetaxel.

In some embodiments, the present disclosure pertains, at least in part, to use of Compound A in a combination therapy with docetaxel in the treatment of cancer in a subject.

In some embodiments, the present disclosure pertains, at least in part, to use of Compound A in a combination therapy with docetaxel for use in reducing or preventing toxicity, hypersensitivity-type infusion reactions, and other negative outcomes resulting from or associated with intravenously administered docetaxel (e.g., Taxotere® or docetaxel formulated with polysorbate 80) therapy in a subject suffering from cancer.

In some embodiments, the present disclosure provides use of Compound A in a combination therapy with docetaxel in the treatment of cancer in a subject in need thereof, wherein Compound A is administered to the subject once a day and for 1-7 times a week;

wherein the subject is also administered docetaxel orally at an amount of about 15 mg/m$^2$ to about 450 mg/m$^2$ once a day and for 1-7 times a week; and wherein Compound A is administered simultaneously with or prior to the docetaxel.

In some embodiments, the present disclosure provides use of Compound A in a combination therapy with docetaxel for reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing docetaxel therapy, wherein Compound A is administered to the subject once a day and for 1-7 times a week;

wherein the subject is also administered docetaxel orally at an amount of about 15 mg/m$^2$ to about 450 mg/m$^2$ once a day and for 1-7 times a week;

wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 30 mg/m$^2$ to 100 mg/m$^2$ over a period of about 1 to about 24 hours once every three weeks, once every two weeks, or once every week; and wherein Compound A is administered simultaneously with or prior to the docetaxel.

In some embodiments, the present disclosure provides use of Compound A in a combination therapy with docetaxel in reducing or preventing hypersensitivity-type infusion reactions associated with intravenously administered docetaxel (e.g., Taxotere® or docetaxel formulated with polysorbate 80) therapy in a subject in need thereof, wherein Compound A is administered to the subject once a day and for 1-7 times a week;

wherein the subject is also administered docetaxel orally at an amount of about 15 mg/m$^2$ to about 450 mg/m$^2$ once a day and for 1-7 times a week;

wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 30 mg/m$^2$ to 100 mg/m$^2$ over a period of about 1 to about 24 hours once every three weeks, once every two weeks, or once every week; and wherein Compound A is administered simultaneously with or prior to the docetaxel.

In some embodiments, the intravenously administered docetaxel (e.g., Taxotere® or docetaxel formulated with polysorbate 80) is infused over a period of about 1 hour once every three weeks.

In some embodiments, the intravenously administered docetaxel (e.g., Taxotere® or docetaxel formulated with polysorbate 80) is infused over a period of about 2 hours once every three weeks.

In some embodiments, the intravenously administered docetaxel (e.g., Taxotere® or docetaxel formulated with polysorbate 80) is infused over a period of about 3 hours once every three weeks.

In some embodiments, the intravenously administered docetaxel (e.g., Taxotere® or docetaxel formulated with polysorbate 80) is infused over a period of about 6 hours once every three weeks.

In some embodiments, the intravenously administered docetaxel (e.g., Taxotere® or docetaxel formulated with polysorbate 80) is infused over a period of about 9 hours once every three weeks.

In some embodiments, the intravenously administered docetaxel (e.g., Taxotere® or docetaxel formulated with polysorbate 80) is infused over a period of about 12 hours once every three weeks.

In some embodiments, the intravenously administered docetaxel (e.g., Taxotere® or docetaxel formulated with polysorbate 80) is infused over a period of about 15 hours once every three weeks.

In some embodiments, the intravenously administered docetaxel (e.g., Taxotere® or docetaxel formulated with polysorbate 80) is infused over a period of about 18 hours once every three weeks.

In some embodiments, the intravenously administered docetaxel (e.g., Taxotere® or docetaxel formulated with polysorbate 80) is infused over a period of about 21 hours once every three weeks.

In some embodiments, the intravenously administered docetaxel (e.g., Taxotere® or docetaxel formulated with polysorbate 80) is infused over a period of about 24 hours once every three weeks.

In some embodiments, the intravenously administered docetaxel (e.g., Taxotere® or docetaxel formulated with polysorbate 80) is infused at about 60 mg/m$^2$ to 100 mg/m$^2$ over a period of about 1 hour, about 2 hours, about 3 hours, about 6 hours, about 9 hours, about 12 hours, about 15 hours, about 18 hours, about 21 hours, or about 24 hours once every three weeks. In some embodiments, the intravenously administered docetaxel (e.g., Taxotere® or docetaxel formulated with polysorbate 80) is infused at about 75 mg/m$^2$.

In some embodiments, the intravenously administered docetaxel (e.g., Taxotere® or docetaxel formulated with polysorbate 80) is infused over a period of about 1 hour once every two weeks.

In some embodiments, the intravenously administered docetaxel (e.g., Taxotere® or docetaxel formulated with polysorbate 80) is infused over a period of about 2 hours once every two weeks.

In some embodiments, the intravenously administered docetaxel (e.g., Taxotere® or docetaxel formulated with polysorbate 80) is infused over a period of about 3 hours once every two weeks.

In some embodiments, the intravenously administered docetaxel (e.g., Taxotere® or docetaxel formulated with polysorbate 80) is infused over a period of about 6 hours once every two weeks.

In some embodiments, the intravenously administered docetaxel (e.g., Taxotere® or docetaxel formulated with polysorbate 80) is infused over a period of about 9 hours once every two weeks.

In some embodiments, the intravenously administered docetaxel (e.g., Taxotere® or docetaxel formulated with polysorbate 80) is infused over a period of about 12 hours once every two weeks.

In some embodiments, the intravenously administered docetaxel (e.g., Taxotere® or docetaxel formulated with polysorbate 80) is infused over a period of about 15 hours once every two weeks.

In some embodiments, the intravenously administered docetaxel (e.g., Taxotere® or docetaxel formulated with polysorbate 80) is infused over a period of about 18 hours once every two weeks.

In some embodiments, the intravenously administered docetaxel (e.g., Taxotere® or docetaxel formulated with polysorbate 80) is infused over a period of about 21 hours once every two weeks.

In some embodiments, the intravenously administered docetaxel (e.g., Taxotere® or docetaxel formulated with polysorbate 80) is infused over a period of about 24 hours once every two weeks.

In some embodiments, the intravenously administered docetaxel (e.g., Taxotere® or docetaxel formulated with polysorbate 80) is infused at about 30 mg/m$^2$ to 80 mg/m$^2$ over a period of about 1 hour, about 2 hours, about 3 hours, about 6 hours, about 9 hours, about 12 hours, about 15 hours, about 18 hours, about 21 hours, or about 24 hours once every two weeks. In some embodiments, the intravenously administered docetaxel (e.g., Taxotere® or docetaxel formulated with polysorbate 80) is infused at about 50 mg/m$^2$.

In some embodiments, the intravenously administered docetaxel (e.g., Taxotere® or docetaxel formulated with polysorbate 80) is infused over a period of about 1 hour once every week.

In some embodiments, the intravenously administered docetaxel (e.g., Taxotere® or docetaxel formulated with polysorbate 80) is infused over a period of about 2 hours once every week.

In some embodiments, the intravenously administered docetaxel (e.g., Taxotere® or docetaxel formulated with polysorbate 80) is infused over a period of about 3 hours once every week.

In some embodiments, the intravenously administered docetaxel (e.g., Taxotere® or docetaxel formulated with polysorbate 80) is infused over a period of about 6 hours once every week.

In some embodiments, the intravenously administered docetaxel (e.g., Taxotere® or docetaxel formulated with polysorbate 80) is infused over a period of about 9 hours once every week.

In some embodiments, the intravenously administered docetaxel (e.g., Taxotere® or docetaxel formulated with polysorbate 80) is infused over a period of about 12 hours once every week.

In some embodiments, the intravenously administered docetaxel (e.g., Taxotere® or docetaxel formulated with polysorbate 80) is infused over a period of about 15 hours once every week.

In some embodiments, the intravenously administered docetaxel (e.g., Taxotere® or docetaxel formulated with polysorbate 80) is infused over a period of about 18 hours once every week.

In some embodiments, the intravenously administered docetaxel (e.g., Taxotere® or docetaxel formulated with polysorbate 80) is infused over a period of about 21 hours once every week.

In some embodiments, the intravenously administered docetaxel (e.g., Taxotere® or docetaxel formulated with polysorbate 80) is infused over a period of about 24 hours once every week.

In some embodiments, the intravenously administered docetaxel (e.g., Taxotere® or docetaxel formulated with polysorbate 80) is infused at about 30 mg/m$^2$ to 60 mg/m$^2$ over a period of about 1 hour, about 2 hours, about 3 hours, about 6 hours, about 9 hours, about 12 hours, about 15 hours, about 18 hours, about 21 hours, or about 24 hours once every week. In some embodiments, the intravenously administered docetaxel (e.g., Taxotere® or docetaxel formulated with polysorbate 80) is infused at about 30 mg/m$^2$. In some embodiments, the docetaxel is intravenously administered for a period of five or six weeks.

In some embodiments, the hematologic toxicity associated with the intravenous administration of docetaxel in a subject suffering from cancer includes anemia and/or myelosuppression. In some embodiments, the myelosuppression may be from leukopenia, neutropenia, and/or thrombocytopenia, or any combination thereof.

In some embodiments, the neurotoxicity associated with the intravenous administration of docetaxel in a subject suffering from cancer includes symptoms such as numbness, tingling, sharp pain, jabbing pain, burning pain, extreme sensitivity, loss of coordination, falling, weakness, paralysis, sweating, heat intolerance, dizziness, changes in blood pressure, bowel problems, and bladder problems, or any combination thereof.

In some embodiments, the present disclosure provides a method for reducing or preventing hypersensitivity-type infusion reactions associated with intravenously administered docetaxel (e.g., Taxotere® or docetaxel formulated with polysorbate 80) therapy in a subject suffering from cancer, comprising:

a. oral administration of docetaxel at an amount of about 15 mg/m$^2$ to about 450 mg/m$^2$ to the subject once a day and for 1-7 times a week; and b. oral administration of Compound A:

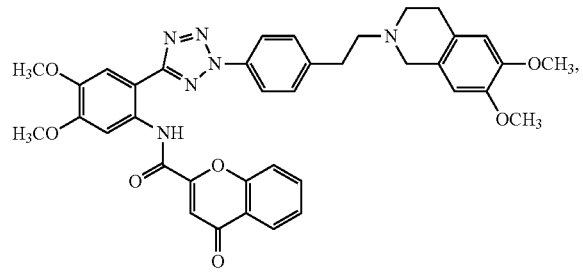 [SMILES: COc1cc2c(cc1OC)CN(CCc1ccc(-n3nnc(-c4cc(OC)c(OC)cc4NC(=O)c4cc(=O)c5ccccc5o4)n3)cc1)CC2]

to the subject once a day and for 1-7 times a week, wherein the orally administered docetaxel reaches therapeutic blood or plasma levels in the subject, and wherein Compound A is administered simultaneously with or prior to the docetaxel.

In some embodiments, the present disclosure provides Compound A for use in reducing or preventing hypersensitivity-type infusion reactions associated with intravenously administered docetaxel (e.g., Taxotere® or docetaxel formulated with polysorbate 80) therapy in a subject suffering from cancer, wherein the subject is administered docetaxel orally at an amount of about 15 mg/m$^2$ to about 450 mg/m$^2$ once a day and for 1-7 times a week;

wherein Compound A:

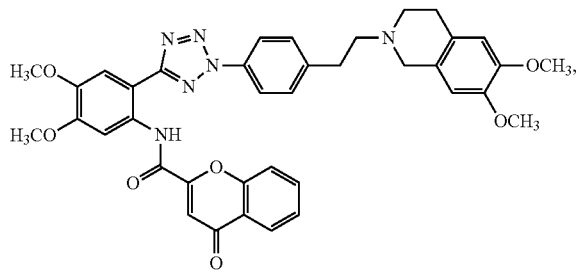 [SMILES: COc1cc2c(cc1OC)CN(CCc1ccc(-n3nnc(-c4cc(OC)c(OC)cc4NC(=O)c4cc(=O)c5ccccc5o4)n3)cc1)CC2]

is administered to the subject once a day and for 1-7 times a week; and wherein the orally administered docetaxel reaches therapeutic blood or plasma levels in the subject, and wherein Compound A is administered simultaneously with or prior to the docetaxel.

In some embodiments, the present disclosure provides the use of Compound A in the manufacture of a medicament for use with docetaxel in reducing or preventing hypersensitivity-type infusion reactions associated with intravenously administered docetaxel (e.g., Taxotere® or docetaxel formulated with polysorbate 80) therapy in a subject suffering from cancer, wherein the subject is administered docetaxel orally at an amount of about 15 mg/m² to about 450 mg/m² once a day and for 1-7 times a week;

wherein Compound A:

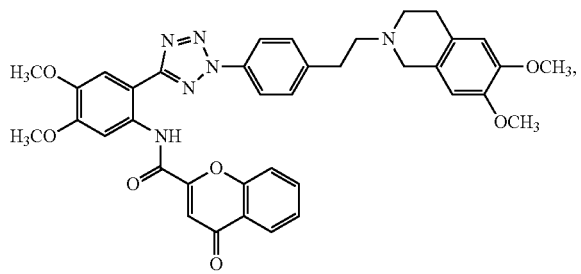 [SMILES: COc1cc2c(cc1OC)CN(CCc1ccc(-n3nnc(-c4cc(OC)c(OC)cc4NC(=O)c4cc(=O)c5ccccc5o4)n3)cc1)CC2]

is administered to the subject once a day and for 1-7 times a week; and wherein the orally administered docetaxel reaches therapeutic blood or plasma levels in the subject, and wherein Compound A is administered simultaneously with or prior to the docetaxel.

In some embodiments, the present disclosure provides the use of Compound A with docetaxel in reducing or preventing hypersensitivity-type infusion reactions associated with intravenously administered docetaxel (e.g., Taxotere® or docetaxel formulated with polysorbate 80) therapy in a subject suffering from cancer, wherein the subject is administered docetaxel orally at an amount of about 15 mg/m² to about 450 mg/m² once a day and for 1-7 times a week;

wherein Compound A:

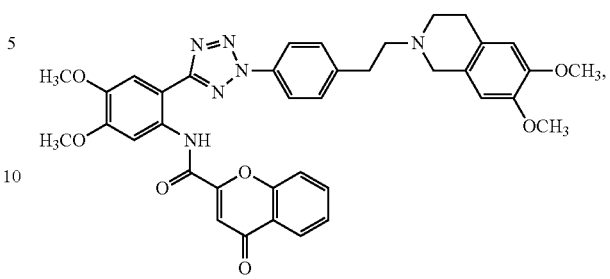

is administered to the subject once a day and for 1-7 times a week; and wherein the orally administered docetaxel reaches therapeutic blood or plasma levels in the subject, and wherein Compound A is administered simultaneously with or prior to the docetaxel.

In some embodiments, the present disclosure provides Compound A for use in a combination therapy with docetaxel for reducing or preventing hypersensitivity-type infusion reactions associated with intravenously administered docetaxel (e.g., Taxotere® or docetaxel formulated with polysorbate 80) therapy in a subject suffering from cancer, wherein Compound A:

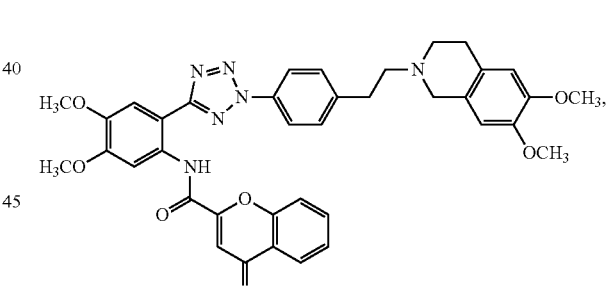

is administered to the subject once a day and for 1-7 times a week; and wherein the subject is also administered docetaxel orally at an amount of about 15 mg/m² to about 450 mg/m² once a day and for 1-7 times a week; and wherein the orally administered docetaxel reaches therapeutic blood or plasma levels in the subject, and wherein Compound A is administered simultaneously with or prior to the docetaxel.

In some embodiments, the present disclosure provides a medicament for use in a combination therapy with docetaxel for reducing or preventing hypersensitivity-type infusion reactions associated with intravenously administered docetaxel (e.g., Taxotere® or docetaxel formulated with polysorbate 80) therapy in a subject suffering from cancer, wherein the medicament comprises Compound A:

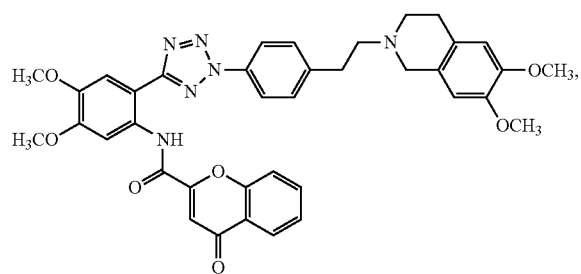 [SMILES: COc1cc2c(cc1OC)CN(CCc1ccc(-n3nnc(-c4cc(OC)c(OC)cc4NC(=O)c4cc(=O)c5ccccc5o4)n3)cc1)CC2]

which is administered to the subject once a day and for 1-7 times a week; and
wherein the subject is also administered docetaxel orally at an amount of about 15 mg/m² to about 450 mg/m² once a day and for 1-7 times a week; and wherein the orally administered docetaxel reaches therapeutic blood or plasma levels in the subject, and
wherein the medicament is administered simultaneously with or prior to the docetaxel.

In some embodiments, the present disclosure provides use of Compound A in a combination therapy with docetaxel for reducing or preventing hypersensitivity-type infusion reactions associated with intravenously administered docetaxel (e.g., Taxotere® or docetaxel formulated with polysorbate 80) therapy in a subject suffering from cancer, wherein Compound A:

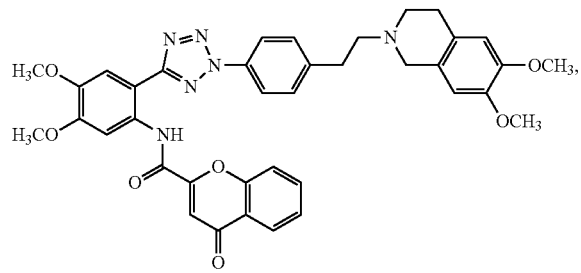 [SMILES: COc1cc2c(cc1OC)CN(CCc1ccc(-n3nnc(-c4cc(OC)c(OC)cc4NC(=O)c4cc(=O)c5ccccc5o4)n3)cc1)CC2]

is administered to the subject once a day and for 1-7 times a week; and
wherein the subject is also administered docetaxel orally at an amount of about 15 mg/m² to about 450 mg/m² once a day and for 1-7 times a week; and wherein the orally administered docetaxel reaches therapeutic blood or plasma levels in the subject, and
wherein Compound A is administered simultaneously with or prior to the docetaxel.

In some embodiments, the hypersensitivity-type infusion reactions associated with the intravenous administration of docetaxel in a subject suffering from cancer includes any sign or symptom on the first day of intravenous administration of docetaxel. In some embodiments, the signs or symptoms in the subject include fever, rash, hives, pruritus, flushing, swelling, dyspnea, bronchospasm, stridor, reduced pulmonary expiratory flow, hypoxia, hypertension, hypotension, hypotonia, syncope, falling, incontinence, abdominal pain, vomiting, urticaria, facial swelling, eye disorders, headache, arrhythmia, tachycardia, nausea, chest pain, and anaphylaxis, and/or any combination thereof.

In some embodiments, the docetaxel is administered orally.

In some embodiments, the docetaxel is administered at an amount of about 15 mg/m² to about 450 mg/m².
In some embodiments, the docetaxel is administered at an amount of about 15 mg/m² to about 400 mg/m².
In some embodiments, the docetaxel is administered at an amount of about 20 mg/m² to about 350 mg/m².
In some embodiments, the docetaxel is administered at an amount of about 25 mg/m² to about 350 mg/m².
In some embodiments, the docetaxel is administered at an amount of about 30 mg/m² to about 350 mg/m².
In some embodiments, the docetaxel is administered at an amount of about 35 mg/m² to about 350 mg/m².
In some embodiments, the docetaxel is administered at an amount of about 40 mg/m² to about 350 mg/m².
In some embodiments, the docetaxel is administered at an amount of about 45 mg/m² to about 350 mg/m².
In some embodiments, the docetaxel is administered at an amount of about 50 mg/m² to about 350 mg/m².
In some embodiments, the docetaxel is administered at an amount of about 50 mg/m² to about 325 mg/m².
In some embodiments, the docetaxel is administered at an amount of about 50 mg/m² to about 300 mg/m².
In some embodiments, the docetaxel is administered at an amount of about 50 mg/m² to about 275 mg/m².
In some embodiments, the docetaxel is administered at an amount of about 50 mg/m² to about 250 mg/m².
In some embodiments, the docetaxel is administered at an amount of about 50 mg/m² to about 225 mg/m².
In some embodiments, the docetaxel is administered at an amount of about 50 mg/m² to about 200 mg/m².
In some embodiments, the docetaxel is administered at an amount of about 50 mg/m² to about 175 mg/m².
In some embodiments, the docetaxel is administered at an amount of about 50 mg/m² to about 150 mg/m².
In some embodiments, the docetaxel is administered at an amount of about 55 mg/m² to about 350 mg/m².
In some embodiments, the docetaxel is administered at an amount of about 55 mg/m² to about 325 mg/m².
In some embodiments, the docetaxel is administered at an amount of about 55 mg/m² to about 300 mg/m².
In some embodiments, the docetaxel is administered at an amount of about 55 mg/m² to about 275 mg/m².
In some embodiments, the docetaxel is administered at an amount of about 55 mg/m² to about 250 mg/m².
In some embodiments, the docetaxel is administered at an amount of about 55 mg/m² to about 225 mg/m².
In some embodiments, the docetaxel is administered at an amount of about 55 mg/m² to about 200 mg/m².
In some embodiments, the docetaxel is administered at an amount of about 55 mg/m² to about 175 mg/m².
In some embodiments, the docetaxel is administered at an amount of about 55 mg/m² to about 150 mg/m².
In some embodiments, the docetaxel is administered at an amount of about 60 mg/m² to about 350 mg/m².
In some embodiments, the docetaxel is administered at an amount of about 60 mg/m² to about 325 mg/m².
In some embodiments, the docetaxel is administered at an amount of about 60 mg/m² to about 300 mg/m².
In some embodiments, the docetaxel is administered at an amount of about 60 mg/m² to about 275 mg/m².

In some embodiments, the docetaxel is administered at an amount of about 60 mg/m² to about 250 mg/m².

In some embodiments, the docetaxel is administered at an amount of about 60 mg/m² to about 225 mg/m².

In some embodiments, the docetaxel is administered at an amount of about 60 mg/m² to about 200 mg/m².

In some embodiments, the docetaxel is administered at an amount of about 60 mg/m² to about 175 mg/m².

In some embodiments, the docetaxel is administered at an amount of about 60 mg/m² to about 150 mg/m².

In some embodiments, the docetaxel is administered at an amount of about 65 mg/m² to about 350 mg/m².

In some embodiments, the docetaxel is administered at an amount of about 65 mg/m² to about 325 mg/m².

In some embodiments, the docetaxel is administered at an amount of about 65 mg/m² to about 300 mg/m².

In some embodiments, the docetaxel is administered at an amount of about 65 mg/m² to about 275 mg/m².

In some embodiments, the docetaxel is administered at an amount of about 65 mg/m² to about 250 mg/m².

In some embodiments, the docetaxel is administered at an amount of about 65 mg/m² to about 225 mg/m².

In some embodiments, the docetaxel is administered at an amount of about 65 mg/m² to about 200 mg/m².

In some embodiments, the docetaxel is administered at an amount of about 65 mg/m² to about 175 mg/m².

In some embodiments, the docetaxel is administered at an amount of about 65 mg/m² to about 150 mg/m².

In some embodiments, the docetaxel is administered at an amount of about 70 mg/m² to about 350 mg/m².

In some embodiments, the docetaxel is administered at an amount of about 70 mg/m² to about 325 mg/m².

In some embodiments, the docetaxel is administered at an amount of about 70 mg/m² to about 300 mg/m².

In some embodiments, the docetaxel is administered at an amount of about 70 mg/m² to about 275 mg/m².

In some embodiments, the docetaxel is administered at an amount of about 70 mg/m² to about 250 mg/m².

In some embodiments, the docetaxel is administered at an amount of about 70 mg/m² to about 225 mg/m².

In some embodiments, the docetaxel is administered at an amount of about 70 mg/m² to about 200 mg/m².

In some embodiments, the docetaxel is administered at an amount of about 70 mg/m² to about 175 mg/m².

In some embodiments, the docetaxel is administered at an amount of about 70 mg/m² to about 150 mg/m².

In some embodiments, the docetaxel is administered at an amount of about 75 mg/m² to about 350 mg/m².

In some embodiments, the docetaxel is administered at an amount of about 75 mg/m² to about 325 mg/m².

In some embodiments, the docetaxel is administered at an amount of about 75 mg/m² to about 300 mg/m².

In some embodiments, the docetaxel is administered at an amount of about 75 mg/m² to about 275 mg/m².

In some embodiments, the docetaxel is administered at an amount of about 75 mg/m² to about 250 mg/m².

In some embodiments, the docetaxel is administered at an amount of about 75 mg/m² to about 225 mg/m².

In some embodiments, the docetaxel is administered at an amount of about 75 mg/m² to about 200 mg/m².

In some embodiments, the docetaxel is administered at an amount of about 75 mg/m² to about 175 mg/m².

In some embodiments, the docetaxel is administered at an amount of about 75 mg/m² to about 150 mg/m².

In some embodiments, the docetaxel is administered at an amount of about 80 mg/m² to about 350 mg/m².

In some embodiments, the docetaxel is administered at an amount of about 80 mg/m² to about 325 mg/m².

In some embodiments, the docetaxel is administered at an amount of about 80 mg/m² to about 300 mg/m².

In some embodiments, the docetaxel is administered at an amount of about 80 mg/m² to about 275 mg/m².

In some embodiments, the docetaxel is administered at an amount of about 80 mg/m² to about 250 mg/m².

In some embodiments, the docetaxel is administered at an amount of about 80 mg/m² to about 225 mg/m².

In some embodiments, the docetaxel is administered at an amount of about 80 mg/m² to about 200 mg/m².

In some embodiments, the docetaxel is administered at an amount of about 80 mg/m² to about 175 mg/m².

In some embodiments, the docetaxel is administered at an amount of about 80 mg/m² to about 150 mg/m².

In some embodiments, the docetaxel is administered at an amount of about 85 mg/m² to about 350 mg/m².

In some embodiments, the docetaxel is administered at an amount of about 85 mg/m² to about 325 mg/m².

In some embodiments, the docetaxel is administered at an amount of about 85 mg/m² to about 300 mg/m².

In some embodiments, the docetaxel is administered at an amount of about 85 mg/m² to about 275 mg/m².

In some embodiments, the docetaxel is administered at an amount of about 85 mg/m² to about 250 mg/m².

In some embodiments, the docetaxel is administered at an amount of about 85 mg/m² to about 225 mg/m².

In some embodiments, the docetaxel is administered at an amount of about 85 mg/m² to about 200 mg/m².

In some embodiments, the docetaxel is administered at an amount of about 85 mg/m² to about 175 mg/m².

In some embodiments, the docetaxel is administered at an amount of about 85 mg/m² to about 150 mg/m².

In some embodiments, the docetaxel is administered at an amount of about 90 mg/m² to about 350 mg/m².

In some embodiments, the docetaxel is administered at an amount of about 90 mg/m² to about 325 mg/m².

In some embodiments, the docetaxel is administered at an amount of about 90 mg/m² to about 300 mg/m².

In some embodiments, the docetaxel is administered at an amount of about 90 mg/m² to about 275 mg/m².

In some embodiments, the docetaxel is administered at an amount of about 90 mg/m² to about 250 mg/m².

In some embodiments, the docetaxel is administered at an amount of about 90 mg/m² to about 225 mg/m².

In some embodiments, the docetaxel is administered at an amount of about 90 mg/m² to about 200 mg/m².

In some embodiments, the docetaxel is administered at an amount of about 90 mg/m² to about 175 mg/m².

In some embodiments, the docetaxel is administered at an amount of about 90 mg/m² to about 150 mg/m².

In some embodiments, the docetaxel is administered at an amount of about 95 mg/m² to about 350 mg/m².

In some embodiments, the docetaxel is administered at an amount of about 95 mg/m² to about 325 mg/m².

In some embodiments, the docetaxel is administered at an amount of about 95 mg/m² to about 300 mg/m².

In some embodiments, the docetaxel is administered at an amount of about 95 mg/m² to about 275 mg/m².

In some embodiments, the docetaxel is administered at an amount of about 95 mg/m² to about 250 mg/m².

In some embodiments, the docetaxel is administered at an amount of about 95 mg/m² to about 225 mg/m².

In some embodiments, the docetaxel is administered at an amount of about 95 mg/m² to about 200 mg/m².

In some embodiments, the docetaxel is administered at an amount of about 95 mg/m$^2$ to about 175 mg/m$^2$.

In some embodiments, the docetaxel is administered at an amount of about 95 mg/m$^2$ to about 150 mg/m$^2$.

In some embodiments, the docetaxel is administered at an amount of about 100 mg/m$^2$ to about 350 mg/m$^2$.

In some embodiments, the docetaxel is administered at an amount of about 100 mg/m$^2$ to about 325 mg/m$^2$.

In some embodiments, the docetaxel is administered at an amount of about 100 mg/m$^2$ to about 300 mg/m$^2$.

In some embodiments, the docetaxel is administered at an amount of about 100 mg/m$^2$ to about 275 mg/m$^2$.

In some embodiments, the docetaxel is administered at an amount of about 100 mg/m$^2$ to about 250 mg/m$^2$.

In some embodiments, the docetaxel is administered at an amount of about 100 mg/m$^2$ to about 225 mg/m$^2$.

In some embodiments, the docetaxel is administered at an amount of about 100 mg/m$^2$ to about 200 mg/m$^2$.

In some embodiments, the docetaxel is administered at an amount of about 100 mg/m$^2$ to about 175 mg/m$^2$.

In some embodiments, the docetaxel is administered at an amount of about 100 mg/m$^2$ to about 150 mg/m$^2$.

In some embodiments, the docetaxel is administered at an amount of about 105 mg/m$^2$ to about 350 mg/m$^2$.

In some embodiments, the docetaxel is administered at an amount of about 105 mg/m$^2$ to about 325 mg/m$^2$.

In some embodiments, the docetaxel is administered at an amount of about 105 mg/m$^2$ to about 300 mg/m$^2$.

In some embodiments, the docetaxel is administered at an amount of about 105 mg/m$^2$ to about 275 mg/m$^2$.

In some embodiments, the docetaxel is administered at an amount of about 105 mg/m$^2$ to about 250 mg/m$^2$.

In some embodiments, the docetaxel is administered at an amount of about 105 mg/m$^2$ to about 225 mg/m$^2$.

In some embodiments, the docetaxel is administered at an amount of about 105 mg/m$^2$ to about 200 mg/m$^2$.

In some embodiments, the docetaxel is administered at an amount of about 105 mg/m$^2$ to about 175 mg/m$^2$.

In some embodiments, the docetaxel is administered at an amount of about 105 mg/m$^2$ to about 150 mg/m$^2$.

In some embodiments, the docetaxel is administered at an amount of about 110 mg/m$^2$ to about 350 mg/m$^2$.

In some embodiments, the docetaxel is administered at an amount of about 110 mg/m$^2$ to about 325 mg/m$^2$.

In some embodiments, the docetaxel is administered at an amount of about 110 mg/m$^2$ to about 300 mg/m$^2$.

In some embodiments, the docetaxel is administered at an amount of about 110 mg/m$^2$ to about 275 mg/m$^2$.

In some embodiments, the docetaxel is administered at an amount of about 110 mg/m$^2$ to about 250 mg/m$^2$.

In some embodiments, the docetaxel is administered at an amount of about 110 mg/m$^2$ to about 225 mg/m$^2$.

In some embodiments, the docetaxel is administered at an amount of about 110 mg/m$^2$ to about 200 mg/m$^2$.

In some embodiments, the docetaxel is administered at an amount of about 110 mg/m$^2$ to about 175 mg/m$^2$.

In some embodiments, the docetaxel is administered at an amount of about 110 mg/m$^2$ to about 150 mg/m$^2$.

In some embodiments, the docetaxel is administered at an amount of about 115 mg/m$^2$ to about 350 mg/m$^2$.

In some embodiments, the docetaxel is administered at an amount of about 115 mg/m$^2$ to about 325 mg/m$^2$.

In some embodiments, the docetaxel is administered at an amount of about 115 mg/m$^2$ to about 300 mg/m$^2$.

In some embodiments, the docetaxel is administered at an amount of about 115 mg/m$^2$ to about 275 mg/m$^2$.

In some embodiments, the docetaxel is administered at an amount of about 115 mg/m$^2$ to about 250 mg/m$^2$.

In some embodiments, the docetaxel is administered at an amount of about 115 mg/m$^2$ to about 225 mg/m$^2$.

In some embodiments, the docetaxel is administered at an amount of about 115 mg/m$^2$ to about 200 mg/m$^2$.

In some embodiments, the docetaxel is administered at an amount of about 115 mg/m$^2$ to about 175 mg/m$^2$.

In some embodiments, the docetaxel is administered at an amount of about 115 mg/m$^2$ to about 150 mg/m$^2$.

In some embodiments, the docetaxel is administered at an amount of about 120 mg/m$^2$ to about 350 mg/m$^2$.

In some embodiments, the docetaxel is administered at an amount of about 120 mg/m$^2$ to about 325 mg/m$^2$.

In some embodiments, the docetaxel is administered at an amount of about 120 mg/m$^2$ to about 300 mg/m$^2$.

In some embodiments, the docetaxel is administered at an amount of about 120 mg/m$^2$ to about 275 mg/m$^2$.

In some embodiments, the docetaxel is administered at an amount of about 120 mg/m$^2$ to about 250 mg/m$^2$.

In some embodiments, the docetaxel is administered at an amount of about 120 mg/m$^2$ to about 225 mg/m$^2$.

In some embodiments, the docetaxel is administered at an amount of about 120 mg/m$^2$ to about 200 mg/m$^2$.

In some embodiments, the docetaxel is administered at an amount of about 120 mg/m$^2$ to about 175 mg/m$^2$.

In some embodiments, the docetaxel is administered at an amount of about 120 mg/m$^2$ to about 150 mg/m$^2$.

In some embodiments, the docetaxel is administered at an amount of about 125 mg/m$^2$ to about 350 mg/m$^2$.

In some embodiments, the docetaxel is administered at an amount of about 125 mg/m$^2$ to about 325 mg/m$^2$.

In some embodiments, the docetaxel is administered at an amount of about 125 mg/m$^2$ to about 300 mg/m$^2$.

In some embodiments, the docetaxel is administered at an amount of about 125 mg/m$^2$ to about 275 mg/m$^2$.

In some embodiments, the docetaxel is administered at an amount of about 125 mg/m$^2$ to about 250 mg/m$^2$.

In some embodiments, the docetaxel is administered at an amount of about 125 mg/m$^2$ to about 225 mg/m$^2$.

In some embodiments, the docetaxel is administered at an amount of about 125 mg/m$^2$ to about 200 mg/m$^2$.

In some embodiments, the docetaxel is administered at an amount of about 125 mg/m$^2$ to about 175 mg/m$^2$.

In some embodiments, the docetaxel is administered at an amount of about 125 mg/m$^2$ to about 150 mg/m$^2$.

In some embodiments, the docetaxel is administered at an amount of about 130 mg/m$^2$ to about 350 mg/m$^2$.

In some embodiments, the docetaxel is administered at an amount of about 130 mg/m$^2$ to about 325 mg/m$^2$.

In some embodiments, the docetaxel is administered at an amount of about 130 mg/m$^2$ to about 300 mg/m$^2$.

In some embodiments, the docetaxel is administered at an amount of about 130 mg/m$^2$ to about 275 mg/m$^2$.

In some embodiments, the docetaxel is administered at an amount of about 130 mg/m$^2$ to about 250 mg/m$^2$.

In some embodiments, the docetaxel is administered at an amount of about 130 mg/m$^2$ to about 225 mg/m$^2$.

In some embodiments, the docetaxel is administered at an amount of about 130 mg/m$^2$ to about 200 mg/m$^2$.

In some embodiments, the docetaxel is administered at an amount of about 130 mg/m$^2$ to about 175 mg/m$^2$.

In some embodiments, the docetaxel is administered at an amount of about 130 mg/m$^2$ to about 150 mg/m$^2$.

In some embodiments, the docetaxel is administered at an amount of about 135 mg/m$^2$ to about 350 mg/m$^2$.

In some embodiments, the docetaxel is administered at an amount of about 135 mg/m² to about 325 mg/m².

In some embodiments, the docetaxel is administered at an amount of about 135 mg/m² to about 300 mg/m².

In some embodiments, the docetaxel is administered at an amount of about 135 mg/m² to about 275 mg/m².

In some embodiments, the docetaxel is administered at an amount of about 135 mg/m² to about 250 mg/m².

In some embodiments, the docetaxel is administered at an amount of about 135 mg/m² to about 225 mg/m².

In some embodiments, the docetaxel is administered at an amount of about 135 mg/m² to about 200 mg/m².

In some embodiments, the docetaxel is administered at an amount of about 135 mg/m² to about 175 mg/m².

In some embodiments, the docetaxel is administered at an amount of about 135 mg/m² to about 150 mg/m².

In some embodiments, the docetaxel is administered at an amount of about 140 mg/m² to about 350 mg/m².

In some embodiments, the docetaxel is administered at an amount of about 140 mg/m² to about 325 mg/m².

In some embodiments, the docetaxel is administered at an amount of about 140 mg/m² to about 300 mg/m².

In some embodiments, the docetaxel is administered at an amount of about 140 mg/m² to about 275 mg/m².

In some embodiments, the docetaxel is administered at an amount of about 140 mg/m² to about 250 mg/m².

In some embodiments, the docetaxel is administered at an amount of about 140 mg/m² to about 225 mg/m².

In some embodiments, the docetaxel is administered at an amount of about 140 mg/m² to about 200 mg/m².

In some embodiments, the docetaxel is administered at an amount of about 140 mg/m² to about 175 mg/m².

In some embodiments, the docetaxel is administered at an amount of about 140 mg/m² to about 150 mg/m².

In some embodiments, the docetaxel is administered at an amount of about 145 mg/m² to about 350 mg/m².

In some embodiments, the docetaxel is administered at an amount of about 145 mg/m² to about 325 mg/m².

In some embodiments, the docetaxel is administered at an amount of about 145 mg/m² to about 300 mg/m².

In some embodiments, the docetaxel is administered at an amount of about 145 mg/m² to about 275 mg/m².

In some embodiments, the docetaxel is administered at an amount of about 145 mg/m² to about 250 mg/m².

In some embodiments, the docetaxel is administered at an amount of about 145 mg/m² to about 225 mg/m².

In some embodiments, the docetaxel is administered at an amount of about 145 mg/m² to about 200 mg/m².

In some embodiments, the docetaxel is administered at an amount of about 145 mg/m² to about 175 mg/m².

In some embodiments, the docetaxel is administered at an amount of about 145 mg/m² to about 150 mg/m².

In some embodiments, the docetaxel is administered at an amount of about 150 mg/m² to about 350 mg/m².

In some embodiments, the docetaxel is administered at an amount of about 150 mg/m² to about 325 mg/m².

In some embodiments, the docetaxel is administered at an amount of about 150 mg/m² to about 300 mg/m².

In some embodiments, the docetaxel is administered at an amount of about 150 mg/m² to about 275 mg/m².

In some embodiments, the docetaxel is administered at an amount of about 150 mg/m² to about 250 mg/m².

In some embodiments, the docetaxel is administered at an amount of about 150 mg/m² to about 225 mg/m².

In some embodiments, the docetaxel is administered at an amount of about 200 mg/m² to about 300 mg/m².

In some embodiments, the docetaxel is administered at an amount of about 225 mg/m² to about 300 mg/m².

In some embodiments, the docetaxel is administered at an amount of about 250 mg/m² to about 350 mg/m².

In some embodiments, the docetaxel is administered at an amount of about 15 mg/m².

In some embodiments, the docetaxel is administered at an amount of about 20 mg/m².

In some embodiments, the docetaxel is administered at an amount of about 25 mg/m².

In some embodiments, the docetaxel is administered at an amount of about 30 mg/m².

In some embodiments, the docetaxel is administered at an amount of about 35 mg/m².

In some embodiments, the docetaxel is administered at an amount of about 40 mg/m².

In some embodiments, the docetaxel is administered at an amount of about 45 mg/m².

In some embodiments, the docetaxel is administered at an amount of about 50 mg/m².

In some embodiments, the docetaxel is administered at an amount of about 55 mg/m².

In some embodiments, the docetaxel is administered at an amount of about 60 mg/m².

In some embodiments, the docetaxel is administered at an amount of about 65 mg/m².

In some embodiments, the docetaxel is administered at an amount of about 70 mg/m².

In some embodiments, the docetaxel is administered at an amount of about 75 mg/m².

In some embodiments, the docetaxel is administered at an amount of about 80 mg/m².

In some embodiments, the docetaxel is administered at an amount of about 85 mg/m².

In some embodiments, the docetaxel is administered at an amount of about 90 mg/m².

In some embodiments, the docetaxel is administered at an amount of about 95 mg/m².

In some embodiments, the docetaxel is administered at an amount of about 100 mg/m².

In some embodiments, the docetaxel is administered at an amount of about 105 mg/m².

In some embodiments, the docetaxel is administered at an amount of about 110 mg/m².

In some embodiments, the docetaxel is administered at an amount of about 115 mg/m².

In some embodiments, the docetaxel is administered at an amount of about 120 mg/m².

In some embodiments, the docetaxel is administered at an amount of about 125 mg/m².

In some embodiments, the docetaxel is administered at an amount of about 130 mg/m².

In some embodiments, the docetaxel is administered at an amount of about 135 mg/m².

In some embodiments, the docetaxel is administered at an amount of about 140 mg/m².

In some embodiments, the docetaxel is administered at an amount of about 145 mg/m².

In some embodiments, the docetaxel is administered at an amount of about 150 mg/m².

In some embodiments, the docetaxel is administered at an amount of about 155 mg/m².

In some embodiments, the docetaxel is administered at an amount of about 160 mg/m².

In some embodiments, the docetaxel is administered at an amount of about 165 mg/m².

In some embodiments, the docetaxel is administered at an amount of about 170 mg/m².
In some embodiments, the docetaxel is administered at an amount of about 175 mg/m².
In some embodiments, the docetaxel is administered at an amount of about 180 mg/m².
In some embodiments, the docetaxel is administered at an amount of about 185 mg/m².
In some embodiments, the docetaxel is administered at an amount of about 190 mg/m².
In some embodiments, the docetaxel is administered at an amount of about 195 mg/m².
In some embodiments, the docetaxel is administered at an amount of about 200 mg/m².
In some embodiments, the docetaxel is administered at an amount of about 205 mg/m².
In some embodiments, the docetaxel is administered at an amount of about 210 mg/m².
In some embodiments, the docetaxel is administered at an amount of about 215 mg/m².
In some embodiments, the docetaxel is administered at an amount of about 220 mg/m².
In some embodiments, the docetaxel is administered at an amount of about 225 mg/m².
In some embodiments, the docetaxel is administered at an amount of about 230 mg/m².
In some embodiments, the docetaxel is administered at an amount of about 235 mg/m².
In some embodiments, the docetaxel is administered at an amount of about 240 mg/m².
In some embodiments, the docetaxel is administered at an amount of about 245 mg/m².
In some embodiments, the docetaxel is administered at an amount of about 250 mg/m².
In some embodiments, the docetaxel is administered at an amount of about 275 mg/m².
In some embodiments, the docetaxel is administered at an amount of about 300 mg/m².
In some embodiments, the docetaxel is administered at an amount of about 325 mg/m².
In some embodiments, the docetaxel is administered at an amount of about 350 mg/m².
In some embodiments, the docetaxel is administered at an amount of about 375 mg/m².
In some embodiments, the docetaxel is administered at an amount of about 400 mg/m².
In some embodiments, the docetaxel is administered at an amount of about 425 mg/m².
In some embodiments, the docetaxel is administered at an amount of about 450 mg/m².
In some embodiments, the docetaxel is administered as a single dose on a single day.
In some embodiments, the docetaxel is administered on consecutive days.
In some embodiments, the docetaxel is administered 1-7 times per week.
In some embodiments, the docetaxel is administered 1-6 times per week. In some embodiments, the docetaxel is administered 1-5 times per week. In some embodiments, the docetaxel is administered 1-4 times per week. In some embodiments, the docetaxel is administered 1-3 times per week. In some embodiments, the docetaxel is administered 1-2 times per week.
In some embodiments, the docetaxel is administered 2-7 times per week. In some embodiments, the docetaxel is administered 2-6 times per week. In some embodiments, the docetaxel is administered 2-5 times per week. In some embodiments, the docetaxel is administered 2-4 times per week. In some embodiments, the docetaxel is administered 2-3 times per week.

In some embodiments, the docetaxel is administered 3-6 times per week. In some embodiments, the docetaxel is administered 3-5 times per week. In some embodiments, the docetaxel is administered 3-4 times per week.

In some embodiments, the docetaxel is administered 4-6 times per week. In some embodiments, the docetaxel is administered 4-5 times per week.

In some embodiments, the docetaxel is administered 5-6 times per week. In some embodiments, the docetaxel is administered less than five times per week.

In some embodiments, the docetaxel is administered once per week. In some embodiments, the docetaxel is administered twice per week. In some embodiments, the docetaxel is administered three times per week. In some embodiments, the docetaxel is administered four times per week. In some embodiments, the docetaxel is administered five times per week. In some embodiments, the docetaxel is administered six times per week.

In some embodiments, the docetaxel is administered at a single dose twice per week. In some embodiments, the docetaxel is administered at a single dose three times per week. In some embodiments, the docetaxel is administered at a single dose four times per week. In some embodiments, the docetaxel is administered at a single dose five times per week. In some embodiments, the docetaxel is administered at a single dose six times per week.

In some embodiments, the docetaxel is administered at least once per week. In some embodiments, the docetaxel is administered at least once per week at an amount of any dosage described above. In some embodiments, the docetaxel is administered once over a three-week period. In some embodiments, the docetaxel is administered as one single dose over a three-week period.

In some embodiments, the docetaxel is administered at least once per week at an amount of about 25 mg/m², about 30 mg/m², about 35 mg/m², about 40 mg/m², about 45 mg/m², about 50 mg/m², about 55 mg/m², about 60 mg/m², about 65 mg/m², about 70 mg/m², about 75 mg/m², about 80 mg/m², about 85 mg/m², about 90 mg/m², about 95 mg/m², or about 100 mg/m². In some embodiments, the docetaxel is administered at least once per week at an amount of about 105 mg/m², about 110 mg/m², about 115 mg/m², about 120 mg/m², about 125 mg/m², about 130 mg/m², about 135 mg/m², about 140 mg/m², about 145 mg/m², or about 150 mg/m².

In some embodiments, the docetaxel is administered at least once per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², about 250 mg/m², about 255 mg/m², about 260 mg/m², about 265 mg/m², about 270 mg/m², about 275 mg/m², about 280 mg/m², about 285 mg/m², about 290 mg/m², about 295 mg/m², about 300 mg/m², about 305 mg/m², about 310 mg/m², about 315 mg/m², about 320 mg/m², about 325 mg/m², about 330 mg/m², about 335 mg/m², about 340 mg/m², about 345 mg/m², about 350 mg/m², about 355 mg/m², about 360 mg/m², about 365 mg/m², about 370 mg/m², about 375 mg/m², about 380 mg/m², about 385 mg/m², about 390 mg/m², about 395 mg/m², or about 400 mg/m². In some embodiments, the docetaxel is administered at least once per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², or about 250 mg/m². In some embodiments, the docetaxel is administered at least once per week at an amount of about 225 mg/m², about 250 mg/m², about 275 mg/m², about 300 mg/m², about 325 mg/m², or about 350 mg/m².

In some embodiments, the docetaxel is administered at about 225 mg/m², once over a three-week period. In some embodiments, the docetaxel is administered at a single dose at about 225 mg/m², once over a three-week period. In some embodiments, the docetaxel is administered at about 150 mg/m², once over a three-week period. In some embodiments, the docetaxel is administered at a single dose at about 150 mg/m², once over a three-week period. In some embodiments, the docetaxel is administered at about 75 mg/m², once over a three-week period. In some embodiments, the docetaxel is administered at a single dose at about 75 mg/m², once over a three-week period.

In some embodiments, the docetaxel is administered at least twice per week. In some embodiments, the docetaxel is administered at least twice per week at an amount of any dosage as described above. In some embodiments, the docetaxel is administered twice over a three-week period. In some embodiments, the docetaxel is administered twice on consecutive days over a three-week period. In some embodiments, the docetaxel is administered as two single doses over a three-week period.

In some embodiments, the docetaxel is administered at least twice per week at an amount of about 25 mg/m², about 30 mg/m², about 35 mg/m², about 40 mg/m², about 45 mg/m², about 50 mg/m², about 55 mg/m², about 60 mg/m², about 65 mg/m², about 70 mg/m², about 75 mg/m², about 80 mg/m², about 85 mg/m², about 90 mg/m², about 95 mg/m², or about 100 mg/m². In some embodiments, the docetaxel is administered at least twice per week at an amount of about 105 mg/m², about 110 mg/m², about 115 mg/m², about 120 mg/m², about 125 mg/m², about 130 mg/m², about 135 mg/m², about 140 mg/m², about 145 mg/m², or about 150 mg/m².

In some embodiments, the docetaxel is administered at least twice per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², about 250 mg/m², about 255 mg/m², about 260 mg/m², about 265 mg/m², about 270 mg/m², about 275 mg/m², about 280 mg/m², about 285 mg/m², about 290 mg/m², about 295 mg/m², about 300 mg/m², about 305 mg/m², about 310 mg/m², about 315 mg/m², about 320 mg/m², about 325 mg/m², about 330 mg/m², about 335 mg/m², about 340 mg/m², about 345 mg/m², about 350 mg/m², about 355 mg/m², about 360 mg/m², about 365 mg/m², about 370 mg/m², about 375 mg/m², about 380 mg/m², about 385 mg/m², about 390 mg/m², about 395 mg/m², or about 400 mg/m². In some embodiments, the docetaxel is administered at least twice per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², or about 250 mg/m². In some embodiments, the docetaxel is administered at least twice per week at an amount of about 225 mg/m², about 250 mg/m², about 275 mg/m², about 300 mg/m², about 325 mg/m², or about 350 mg/m².

In some embodiments, the docetaxel is administered at about 225 mg/m², twice on consecutive days over a three-week period. In some embodiments, the docetaxel is administered as a single dose at about 225 mg/m², twice on consecutive days over a three-week period. In some embodiments, the docetaxel is administered at about 150 mg/m², twice on consecutive days over a three-week period. In some embodiments, the docetaxel is administered as single doses at about 150 mg/m², twice on consecutive days over a three-week period. In some embodiments, the docetaxel is administered at about 75 mg/m², twice on consecutive days over a three-week period. In some embodiments, the docetaxel is administered as single doses at about 75 mg/m², twice on consecutive days over a three-week period.

In some embodiments, the docetaxel is administered at least three times per week. In some embodiments, the docetaxel is administered on consecutive days. In some embodiments, the docetaxel is administered at least three times per week at an amount of any dosage as described above. In some embodiments, the docetaxel is administered three times over a three-week period. In some embodiments, the docetaxel is administered three times on consecutive days over a three-week period. In some embodiments, the docetaxel is administered as three single doses over a three-week period.

In some embodiments, the docetaxel is administered at least three times per week at an amount of about 25 mg/m², about 30 mg/m², about 35 mg/m², about 40 mg/m², about 45 mg/m², about 50 mg/m², about 55 mg/m², about 60 mg/m², about 65 mg/m², about 70 mg/m², about 75 mg/m², about 80 mg/m², about 85 mg/m², about 90 mg/m², about 95 mg/m², or about 100 mg/m². In some embodiments, the docetaxel is administered at least three times per week at an amount of about 105 mg/m², about 110 mg/m², about 115 mg/m², about 120 mg/m², about 125 mg/m², about 130 mg/m², about 135 mg/m², about 140 mg/m², about 145 mg/m², or about 150 mg/m².

In some embodiments, the docetaxel is administered at least three times per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², about 250 mg/m², about 255 mg/m², about 260 mg/m², about 265 mg/m², about 270 mg/m², about 275 mg/m², about 280 mg/m², about 285 mg/m², about 290 mg/m², about 295 mg/m², about 300 mg/m², about 305 mg/m², about 310 mg/m², about 315 mg/m², about 320 mg/m², about 325 mg/m², about 330 mg/m², about 335 mg/m², about 340 mg/m², about 345 mg/m², about 350 mg/m², about 355 mg/m², about 360 mg/m², about 365 mg/m², about 370 mg/m², about 375 mg/m², about 380 mg/m², about 385 mg/m², about 390 mg/m², about 395 mg/m², or about 400 mg/m². In some embodiments, the docetaxel is administered at least three times per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², or about 250 mg/m². In some embodiments, the docetaxel is administered at least three times per week at an amount of about 225 mg/m², about 250 mg/m², about 275 mg/m², about 300 mg/m², about 325 mg/m², or about 350 mg/m².

In some embodiments, the docetaxel is administered at about 225 mg/m², three times on consecutive days over a three-week period. In some embodiments, the docetaxel is administered as single doses at about 225 mg/m², three times on consecutive days over a three-week period. In some embodiments, the docetaxel is administered at about 150 mg/m², three times on consecutive days over a three-week period. In some embodiments, the docetaxel is administered as single doses at about 150 mg/m², three times on consecutive days over a three-week period. In some embodiments, the docetaxel is administered at about 75 mg/m², three times on consecutive days over a three-week period. In some embodiments, the docetaxel is administered as single doses at about 75 mg/m², three times on consecutive days over a three-week period.

In some embodiments, the docetaxel is administered at least four times per week. In some embodiments, the docetaxel is administered on consecutive days. In some embodiments, the docetaxel is administered at least four times per week at an amount of any dosage as described above. In some embodiments, the docetaxel is administered four times over a three-week period. In some embodiments, the docetaxel is administered four times on consecutive days over a three-week period. In some embodiments, the docetaxel is administered as four single doses over a three-week period.

In some embodiments, the docetaxel is administered at least four times per week at an amount of about 25 mg/m2, about 30 mg/m2, about 35 mg/m2, about 40 mg/m2, about 45 mg/m2, about 50 mg/m2, about 55 mg/m², about 60 mg/m², about 65 mg/m², about 70 mg/m², about 75 mg/m², about 80 mg/m², about 85 mg/m², about 90 mg/m², about 95 mg/m², or about 100 mg/m². In some embodiments, the docetaxel is administered at least four times per week at an amount of about 105 mg/m², about 110 mg/m², about 115 mg/m², about 120 mg/m², about 125 mg/m², about 130 mg/m², about 135 mg/m², about 140 mg/m², about 145 mg/m², or about 150 mg/m².

In some embodiments, the docetaxel is administered at least four times per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², about 250 mg/m², about 255 mg/m², about 260 mg/m², about 265 mg/m², about 270 mg/m², about 275 mg/m², about 280 mg/m², about 285 mg/m², about 290 mg/m², about 295 mg/m², about 300 mg/m², about 305 mg/m², about 310 mg/m², about 315 mg/m², about 320 mg/m², about 325 mg/m², about 330 mg/m², about 335 mg/m², about 340 mg/m², about 345 mg/m², about 350 mg/m², about 355 mg/m², about 360 mg/m², about 365 mg/m², about 370 mg/m², about 375 mg/m², about 380 mg/m², about 385 mg/m², about 390 mg/m², about 395 mg/m², or about 400 mg/m². In some embodiments, the docetaxel is administered at least four times per week at an amount of about 125 mg/m², about 130 mg/m², about 135 mg/m², about 140 mg/m², about 145 mg/m², about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², or about 250 mg/m². In some embodiments, the docetaxel is administered at least four times per week at an amount of about 125 mg/m², about 130 mg/m², about 135 mg/m², about 140 mg/m², about 145 mg/m², about 150 mg/m², about 155 mg/m², about 160 mg/m², about 165 mg/m², about 170 mg/m², about 175 mg/m², about 200 mg/m², about 225 mg/m², or about 250 mg/m².

In some embodiments, the docetaxel is administered at about 225 mg/m², four times on consecutive days over a three-week period. In some embodiments, the docetaxel is administered as single doses at about 225 mg/m², four times on consecutive days over a three-week period. In some embodiments, the docetaxel is administered at about 150 mg/m², four times on consecutive days over a three-week period. In some embodiments, the docetaxel is administered as single doses at about 150 mg/m², four times on consecutive days over a three-week period. In some embodiments, the docetaxel is administered at about 75 mg/m², four times on consecutive days over a three-week period. In some embodiments, the docetaxel is administered as single doses at about 75 mg/m², four times on consecutive days over a three-week period.

In some embodiments, the docetaxel is administered at least five times per week. In some embodiments, the docetaxel is administered on consecutive days. In some embodiments, the docetaxel is administered at least five times per week at an amount of any dosage as described above. In some embodiments, the docetaxel is administered five times over a three-week period. In some embodiments, the docetaxel is administered five times on consecutive days over a three-week period. In some embodiments, the docetaxel is administered as five single doses over a three-week period.

In some embodiments, the docetaxel is administered at least five times per week at an amount of about 25 mg/m², about 30 mg/m², about 35 mg/m², about 40 mg/m², about 45 mg/m², about 50 mg/m², about 55 mg/m², about 60 mg/m², about 65 mg/m², about 70 mg/m², about 75 mg/m², about 80 mg/m², about 85 mg/m², about 90 mg/m², about 95 mg/m², or about 100 mg/m². In some embodiments, the docetaxel is administered at least 5 times per week at an amount of about 110 mg/m², about 120 mg/m², about 130 mg/m², about 140 mg/m², or about 150 mg/m².

In some embodiments, the docetaxel is administered at least five times per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², about 250 mg/m², about 255 mg/m², about 260 mg/m², about 265 mg/m², about 270 mg/m², about 275 mg/m², about 280 mg/m², about 285 mg/m², about 290 mg/m², about 295 mg/m², about 300 mg/m², about 305 mg/m², about 310 mg/m², about 315 mg/m², about 320 mg/m², about 325 mg/m², about 330 mg/m², about 335 mg/m², about 340 mg/m², about 345 mg/m², about 350 mg/m², about 355 mg/m², about 360 mg/m², about 365 mg/m², about 370 mg/m², about 375 mg/m², about 380 mg/m², about 385 mg/m², about 390 mg/m², about 395 mg/m², or about 400 mg/m². In some embodiments, the docetaxel is administered at least five times per week at an amount of about 250 mg/m², about 275 mg/m², about 300 mg/m², about 325 mg/m², or about 350 mg/m².

In some embodiments, the docetaxel is administered at about 225 mg/m², five times on consecutive days over a three-week period. In some embodiments, the docetaxel is administered as single doses at about 225 mg/m², five times on consecutive days over a three-week period. In some embodiments, the docetaxel is administered at about 150 mg/m², five times on consecutive days over a three-week period. In some embodiments, the docetaxel is administered as single doses at about 150 mg/m², five times on consecutive days over a three-week period. In some embodiments, the docetaxel is administered at about 75 mg/m², five times on consecutive days over a three-week period. In some embodiments, the docetaxel is administered as single doses at about 75 mg/m², five times on consecutive days over a three-week period.

In some embodiments, the docetaxel is administered at least six times per week. In some embodiments, the docetaxel is administered on consecutive days. In some embodiments, the docetaxel is administered at least six times per week at an amount of any dosage as described above. In some embodiments, the docetaxel is administered six times over a three-week period. In some embodiments, the docetaxel is administered six times on consecutive days over a three-week period. In some embodiments, the docetaxel is administered as six single doses over a three-week period.

In some embodiments, the docetaxel is administered at least six times per week at an amount of about 25 mg/m², about 30 mg/m², about 35 mg/m², about 40 mg/m², about 45 mg/m², about 50 mg/m², about 55 mg/m², about 60 mg/m², about 65 mg/m², about 70 mg/m², about 75 mg/m², about 80 mg/m², about 85 mg/m², about 90 mg/m², about 95 mg/m², or about 100 mg/m². In some embodiments, the docetaxel is administered at least six times per week at an amount of about 105 mg/m², about 110 mg/m², about 115 mg/m², about 120 mg/m², about 125 mg/m², about 130 mg/m², about 135 mg/m², about 140 mg/m², about 145 mg/m², or about 150 mg/m².

In some embodiments, the docetaxel is administered at least six times per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², about 250 mg/m², about 255 mg/m², about 260 mg/m², about 265 mg/m², about 270 mg/m², about 275 mg/m², about 280 mg/m², about 285 mg/m², about 290 mg/m², about 295 mg/m², about 300 mg/m², about 305 mg/m², about 310 mg/m², about 315 mg/m², about 320 mg/m², about 325 mg/m², about 330 mg/m², about 335 mg/m², about 340 mg/m², about 345 mg/m², about 350 mg/m², about 355 mg/m², about 360 mg/m², about 365 mg/m², about 370 mg/m², about 375 mg/m², about 380 mg/m², about 385 mg/m², about 390 mg/m², about 395 mg/m², or about 400 mg/m². In some embodiments, the docetaxel is administered at least six times per week at an amount of about 250 mg/m², about 275 mg/m², about 300 mg/m², about 325 mg/m², or about 350 mg/m².

In some embodiments, the docetaxel is administered at about 225 mg/m², six times on consecutive days over a three-week period. In some embodiments, the docetaxel is administered as single doses at about 225 mg/m², six times on consecutive days over a three-week period. In some embodiments, the docetaxel is administered at about 150 mg/m², six times on consecutive days over a three-week period. In some embodiments, the docetaxel is administered as single doses at about 150 mg/m², six times on consecutive days over a three-week period. In some embodiments, the docetaxel is administered at about 75 mg/m², six times on consecutive days over a three-week period. In some embodiments, the docetaxel is administered as single doses at about 75 mg/m², six times on consecutive days over a three-week period.

In some embodiments, the docetaxel is administered at least seven times per week. In some embodiments, the docetaxel is administered on consecutive days. In some embodiments, the docetaxel is administered at least seven times per week at an amount of any dosage as described above. In some embodiments, the docetaxel is administered seven times over a three-week period. In some embodiments, the docetaxel is administered seven times on consecutive days over a three-week period. In some embodiments, the docetaxel is administered as seven single doses over a three-week period.

In some embodiments, the docetaxel is administered at least seven times per week at an amount of about 25 mg/m², about 30 mg/m², about 35 mg/m², about 40 mg/m², about 45 mg/m², about 50 mg/m², about 55 mg/m², about 60 mg/m², about 65 mg/m², about 70 mg/m², about 75 mg/m², about 80 mg/m², about 85 mg/m², about 90 mg/m², about 95 mg/m², or about 100 mg/m². In some embodiments, the docetaxel is administered at least seven times per week at an amount of about 105 mg/m², about 110 mg/m², about 115 mg/m², about 120 mg/m², about 125 mg/m², about 130 mg/m², about 135 mg/m², about 140 mg/m², about 145 mg/m², or about 150 mg/m².

In some embodiments, the docetaxel is administered at least seven times per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², about 250 mg/m², about 255 mg/m², about 260 mg/m², about 265 mg/m², about 270 mg/m², about 275 mg/m², about 280 mg/m², about 285 mg/m², about 290 mg/m², about 295 mg/m², about 300 mg/m², about 305 mg/m², about 310 mg/m², about 315 mg/m², about 320 mg/m², about 325 mg/m², about 330 mg/m², about 335 mg/m², about 340 mg/m², about 345 mg/m², about 350 mg/m², about 355 mg/m², about 360 mg/m², about 365 mg/m², about 370 mg/m², about 375 mg/m², about 380 mg/m², about 385 mg/m², about 390 mg/m², about 395 mg/m², or about 400 mg/m². In some embodiments, the docetaxel is administered at least seven times per week at an amount of about 250 mg/m², about 275 mg/m², about 300 mg/m², about 325 mg/m², or about 350 mg/m².

In some embodiments, the docetaxel is administered at about 225 mg/m², seven times on consecutive days over a three-week period. In some embodiments, the docetaxel is administered as single doses at about 225 mg/m², seven times on consecutive days over a three-week period. In some embodiments, the docetaxel is administered at about 150 mg/m², seven times on consecutive days over a three-week period. In some embodiments, the docetaxel is administered as single doses at about 150 mg/m², seven times on consecutive days over a three-week period. In some embodiments, the docetaxel is administered at about 75 mg/m², seven times on consecutive days over a three-week period. In some embodiments, the docetaxel is administered as single doses at about 75 mg/m², seven times on consecutive days over a three-week period.

In some embodiments, oral administration of docetaxel (i.e., administration of an oral formulation of docetaxel) is preceded by IV administration of docetaxel. In some embodiments, the docetaxel is administered intravenously according to the dosage amount and dosage regimen described herein, followed by administration of an oral formulation of docetaxel as described herein. In some embodiments, the docetaxel is administered intravenously according to the dosage amount once on the first day of the first week, and the administration of an oral formulation of docetaxel starts on the first day of the fourth week, according to the dosage amount and dosage regimen described herein.

In some embodiments, oral administration of docetaxel (i.e., administration of an oral formulation of docetaxel) is preceded by a premedication regimen. In some embodiments, the premedication comprises an antiemetic (e.g., dexamethasone), an oral corticosteroid, or an anti-histamine. In some embodiments, the premedication comprises an antiemetic. In some embodiments, the premedication comprises dexamethasone. In some embodiments, the premedication comprises an oral corticosteroid. In some embodiments, the premedication comprises an anti-histamine.

In some embodiments, the present disclosure includes examples wherein Compound A is administered orally.

In some embodiments, Compound A is administered at an amount of about 1 mg to about 500 mg.

In some embodiments, Compound A is administered at about 1 mg to 400 mg.

In some embodiments, Compound A is administered at about 1 mg to 300 mg.

In some embodiments, Compound A is administered at about 5 mg to 200 mg.

In some embodiments, Compound A is administered at about 10 mg to 100 mg.

In some embodiments, Compound A is administered at about 15 mg to 50 mg.

In some embodiments, Compound A is administered at about 5 mg.

In some embodiments, Compound A is administered at about 10 mg.

In some embodiments, Compound A is administered at about 15 mg.

In some embodiments, Compound A is administered at about 20 mg.

In some embodiments, Compound A is administered at about 25 mg.

In some embodiments, Compound A is administered at about 30 mg.

In some embodiments, Compound A is administered at about 35 mg.

In some embodiments, Compound A is administered at about 45 mg.

In some embodiments, Compound A is administered at about 50 mg.

In some embodiments, Compound A and the docetaxel are administered on the same day.

In some embodiments, Compound A and the docetaxel are administered on the same day as a single dose.

In some embodiments, Compound A and the docetaxel are administered on the same day as a single dose once a week.

In some embodiments, Compound A and the docetaxel are administered on the same day as a single dose once every three weeks.

In some embodiments, Compound A and the docetaxel are administered on the same day as two single daily doses.

In some embodiments, Compound A and the docetaxel are administered on the same day as two single daily doses once a week.

In some embodiments, Compound A and the docetaxel are administered on the same day as two single daily doses once every three weeks.

In some embodiments, Compound A is administered simultaneously with docetaxel.

In some embodiments, Compound A is administered before the docetaxel is administered.

In some embodiments, Compound A is administered about 5 minutes before the docetaxel is administered.

In some embodiments, Compound A is administered about 10 minutes before the docetaxel is administered.

In some embodiments, Compound A is administered about 15 minutes before the docetaxel is administered.

In some embodiments, Compound A is administered about 30 minutes before the docetaxel is administered.

In some embodiments, Compound A is administered about 45 minutes before the docetaxel is administered.

In some embodiments, Compound A is administered about 60 minutes before the docetaxel is administered.

In some embodiments, Compound A is administered about 2 hours before the docetaxel is administered.

In some embodiments, Compound A is administered about 3 hours before the docetaxel is administered.

In some embodiments, Compound A is administered about 4 hours before the docetaxel is administered.

In some embodiments, Compound A is administered about 6 hours before the docetaxel is administered.

In some embodiments, Compound A is administered about 8 hours before the docetaxel is administered.

In some embodiments of the present disclosure, the plasma exposure of the orally administered docetaxel, as measured by $AUC(0\rightarrow\infty)$, is equal to or greater than the plasma exposure of intravenously administered docetaxel (e.g., Taxotere® or docetaxel formulated with polysorbate 80) at an amount of about 60-100 mg/m² (e.g., 75 mg/m²) over a period of about 1-24 hours once every three weeks, or at an amount of about 30-100 mg/m² (e.g., 50 mg/m²) over a period of about 1-24 hours once every two weeks, or at an amount of about 30-75 mg/m² (e.g., 30 mg/m²) over a period of about 1-24 hours once every week, as measured by $AUC(0\rightarrow\infty)$.

In some embodiments of the present disclosure, the plasma exposure of the orally administered docetaxel, as measured by $AUC(0\rightarrow\infty)$, is equal to or greater than the plasma exposure of intravenously administered docetaxel (e.g., Taxotere® or docetaxel formulated with polysorbate 80) at an amount of about 60-100 mg/m² (e.g., 75 mg/m²) over a period of about 1-20 hours once every three weeks, or at an amount of about 30-100 mg/m² (e.g., 50 mg/m²) over a period of about 1-20 hours once every two weeks, or at an amount of about 30-75 mg/m² (e.g., 30 mg/m²) over a period of about 1-20 hours once every week, as measured by $AUC(0\rightarrow\infty)$.

In some embodiments of the present disclosure, the plasma exposure of the orally administered docetaxel, as measured by $AUC(0\rightarrow\infty)$, is equal to or greater than the plasma exposure of intravenously administered docetaxel (e.g., Taxotere® or docetaxel formulated with polysorbate 80) at an amount of about 60-100 mg/m² (e.g., 75 mg/m²)

over a period of about 1-16 hours once every three weeks, or at an amount of about 30-100 mg/m² (e.g., 50 mg/m²) over a period of about 1-16 hours once every two weeks, or at an amount of about 30-75 mg/m² (e.g., 30 mg/m²) over a period of about 1-16 hours once every week, as measured by AUC(0→∞).

In some embodiments of the present disclosure, the plasma exposure of the orally administered docetaxel, as measured by AUC(0→∞), is equal to or greater than the plasma exposure of intravenously administered docetaxel (e.g., Taxotere® or docetaxel formulated with polysorbate 80) at an amount of about 60-100 mg/m² (e.g., 75 mg/m²) over a period of about 2-12 hours once every three weeks, or at an amount of about 30-100 mg/m² (e.g., 50 mg/m²) over a period of about 2-12 hours once every two weeks, or at an amount of about 30-75 mg/m² (e.g., 30 mg/m²) over a period of about 2-12 hours once every week, as measured by AUC(0→∞).

In some embodiments of the present disclosure, the plasma exposure of the orally administered docetaxel, as measured by AUC(0→∞), is equal to or greater than the plasma exposure of intravenously administered docetaxel (e.g., Taxotere® or docetaxel formulated with polysorbate 80) at an amount of about 60-100 mg/m² (e.g., 75 mg/m²) over a period of about 2-10 hours once every three weeks, or at an amount of about 30-100 mg/m² (e.g., 50 mg/m²) over a period of about 2-10 hours once every two weeks, or at an amount of about 30-75 mg/m² (e.g., 30 mg/m²) over a period of about 2-10 hours once every week, as measured by AUC(0→∞).

In some embodiments of the present disclosure, the plasma exposure of the orally administered docetaxel, as measured by AUC(0→∞), is equal to or greater than the plasma exposure of intravenously administered docetaxel (e.g., Taxotere® or docetaxel formulated with polysorbate 80) at an amount of about 60-100 mg/m² (e.g., 75 mg/m²) over a period of about 3-8 hours once every three weeks, or at an amount of about 30-100 mg/m² (e.g., 50 mg/m²) over a period of about 3-8 hours once every two weeks, or at an amount of about 30-75 mg/m² (e.g., 30 mg/m²) over a period of about 3-8 hours once every week, as measured by AUC(0→∞).

In some embodiments of the present disclosure, the plasma exposure of the orally administered docetaxel, as measured by AUC(0→∞), is equal to or greater than the plasma exposure of intravenously administered docetaxel (e.g., Taxotere® or docetaxel formulated with polysorbate 80) at an amount of about 60-100 mg/m² (e.g., 75 mg/m²) over a period of about 60 minutes once every three weeks, or at an amount of about 30-100 mg/m² (e.g., 50 mg/m²) over a period of about 60 minutes once every two weeks, or at an amount of about 30-75 mg/m² (e.g., 30 mg/m²) over a period of about 60 minutes once every week, as measured by AUC(0→∞).

In some embodiments of the present disclosure, the plasma exposure of the orally administered docetaxel, as measured by AUC(0→∞), is equal to or greater than the plasma exposure of intravenously administered docetaxel (e.g., Taxotere® or docetaxel formulated with polysorbate 80) at an amount of about 70-90 mg/m² over a period of about 60 minutes once every three weeks, as measured by AUC(0→∞).

In some embodiments of the present disclosure, the plasma exposure of the orally administered docetaxel, as measured by AUC(0→∞), is equal to or greater than the plasma exposure of intravenously administered docetaxel (e.g., Taxotere® or docetaxel formulated with polysorbate 80) at an amount of about 75-85 mg/m² over a period of about 60 minutes once every three weeks, as measured by $AUC_{(0\to\infty)}$.

In some embodiments of the present disclosure, the plasma exposure of the orally administered docetaxel, as measured by AUC(0→∞), is equal to or greater than the plasma exposure of intravenously administered docetaxel (e.g., Taxotere® or docetaxel formulated with polysorbate 80) at an amount of about 80 mg/m² over a period of about 60 minutes once every three weeks, as measured by AUC (0→∞).

In some embodiments of the present disclosure, the plasma exposure of the orally administered docetaxel, as measured by AUC(0→∞), is equal to or greater than the plasma exposure of intravenously administered docetaxel (e.g., Taxotere® or docetaxel formulated with polysorbate 80) at an amount of about 75 mg/m² over a period of about 60 minutes once every three weeks, as measured by AUC (0→∞).

In some embodiments, the AUC(0→∞) of the orally administered docetaxel is equal to the AUC(0→∞) of intravenously administered docetaxel e.g., Taxotere® or docetaxel formulated with polysorbate 80) at an amount of about 60-100 mg/m² (e.g., 75 mg/m²) over a period of about 60 minutes once every three weeks, or at an amount of about 30-100 mg/m² (e.g., 50 mg/m²) over a period of about 60 minutes once every two weeks, or at an amount of about 30-75 mg/m² (e.g., 30 mg/m²) over a period of about 60 minutes once every week, as measured by AUC(0→∞).

In some embodiments, the AUC(0→∞) of the orally administered docetaxel is equal to the AUC(0→∞) of intravenously administered docetaxel e.g., Taxotere® or docetaxel formulated with polysorbate 80) at an amount of about 70-90 mg/m² over a period of about 60 minutes once every three weeks, as measured by AUC(0→∞).

In some embodiments, the AUC(0→∞) of the orally administered docetaxel is equal to the AUC(0→∞) of intravenously administered docetaxel e.g., Taxotere® or docetaxel formulated with polysorbate 80) at an amount of about 75-85 mg/m² over a period of about 60 minutes once every three weeks, as measured by AUC(0→∞).

In some embodiments, the AUC(0→∞) of the orally administered docetaxel is equal to the AUC(0→∞) of intravenously administered docetaxel e.g., Taxotere® or docetaxel formulated with polysorbate 80) at an amount of about 80 mg/m² over a period of about 60 minutes once every three weeks, as measured by AUC(0→∞).

In some embodiments, the AUC(0→∞) of the orally administered docetaxel is equal to the AUC(0→∞) of intravenously administered docetaxel e.g., Taxotere® or docetaxel formulated with polysorbate 80) at an amount of about 75 mg/m² over a period of about 60 minutes once every three weeks, as measured by AUC(0→∞).

In some embodiments, the AUC(0→∞) of the orally administered docetaxel is greater than the AUC(0→∞) of intravenously administered docetaxel (e.g., Taxotere® or docetaxel formulated with polysorbate 80) at an amount of about 60-100 mg/m² (e.g., 75 mg/m²) over a period of about 60 minutes once every three weeks, or at an amount of about 30-100 mg/m² (e.g., 50 mg/m²) over a period of about 60 minutes once every two weeks, or at an amount of about 30-75 mg/m² (e.g., 30 mg/m²) over a period of about 60 minutes once every week, as measured by AUC(0→∞).

In some embodiments, the AUC(0→∞) of the orally administered docetaxel is greater than the AUC(0→∞) of intravenously administered docetaxel (e.g., Taxotere® or docetaxel formulated with polysorbate 80) at an amount of about 70-90 mg/m$^2$ over a period of about 60 minutes once every three weeks, as measured by AUC(0→∞).

In some embodiments, the AUC(0→∞) of the orally administered docetaxel is greater than the AUC(0→∞) of intravenously administered docetaxel (e.g., Taxotere® or docetaxel formulated with polysorbate 80) at an amount of about 75-85 mg/m$^2$ over a period of about 60 minutes once every three weeks, as measured by AUC(0→∞).

In some embodiments, the AUC(0→∞) of the orally administered docetaxel is greater than the AUC(0→∞) of intravenously administered docetaxel (e.g., Taxotere® or docetaxel formulated with polysorbate 80) at an amount of about 80 mg/m$^2$ over a period of about 60 minutes once every three weeks, as measured by AUC(0→∞).

In some embodiments, the AUC(0→∞) of the orally administered docetaxel is greater than the AUC(0→∞) of intravenously administered docetaxel (e.g., Taxotere® or docetaxel formulated with polysorbate 80) at an amount of about 75 mg/m$^2$ over a period of about 60 minutes once every three weeks, as measured by AUC(0→∞).

In some embodiments, the AUC(0→∞) of the orally administered docetaxel is about 10, 15, 20, 25, 30, 35, 40, 45, 50, 55, 60, 65, 70, 75, 80, 85, 90, 95, or 100% greater than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is at least about 10% greater (e.g., at least 10% greater) than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is at least about 20% greater (e.g., at least 20% greater) than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is at least about 30% greater (e.g., at least 30% greater) than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is at least about 40% greater (e.g., at least 40% greater) than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is at least about 50% greater (e.g., at least 50% greater) than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is at least about 60% greater (e.g., at least 60% greater) than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is at least about 70% greater (e.g., at least 70% greater) than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is at least about 80% greater (e.g., at least 80% greater) than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is at least about 90% greater (e.g., at least 90% greater) than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is at least about 100% greater (e.g., at least 100% greater) than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 10% greater to about 100% greater than the AUC(0→∞) of intravenously administered docetaxel (e.g., Taxotere® or docetaxel formulated with polysorbate 80) at an amount of 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 10% greater to about 90% greater than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 10% greater to about 80% greater than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 10% greater to about 70% greater than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 10% greater to about 60% greater than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 10% greater to about 50% greater than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 10% greater to about 40% greater than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 10% greater to about 35% greater than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 10% greater to about 30% greater than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 10% greater to about 25% greater than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 10% greater to about 20% greater than the AUC(0→∞) of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$), as measured by AUC(0→∞).

In some embodiments, the AUC(0→∞) of the orally administered docetaxel is about 15% greater to about 25% greater than the AUC(0→∞) of intravenously administered docetaxel (e.g., Taxotere® or docetaxel formulated with polysorbate 80) at an amount of about 60-100 mg/m$^2$, about 70-90 mg/m², about 75-85 mg/m², about 80 mg/m², or about 75 mg/m² over a period of about 60 minutes once every three weeks, or at an amount of about 30-100 mg/m² (e.g., 50 mg/m²) over a period of about 60 minutes once every two weeks, or at an amount of about 30-75 mg/m² (e.g., 30 mg/m²), as measured by AUC(0→∞).

In some embodiments, the AUC(0→∞) of the orally administered docetaxel is about 500 ng·h/mL to about 15,000 ng·h/mL.

In some embodiments, the AUC(0→∞) of the orally administered docetaxel is about 1,000 ng·h/mL to about 15,000 ng·h/mL.

In some embodiments, the AUC(0→∞) of the orally administered docetaxel is about 1,500 ng·h/mL to about 10,000 ng·h/mL.

In some embodiments, the AUC(0→∞) of the orally administered docetaxel is about 2,000 ng·h/mL to about 10,000 ng·h/mL.

In some embodiments, the AUC(0→∞) of the orally administered docetaxel is about 2,000 ng·h/mL to about 9,000 ng·h/mL.

In some embodiments, the AUC(0→∞) of the orally administered docetaxel is about 3,000 ng·h/mL to about 9,000 ng·h/mL.

In some embodiments, the AUC(0→∞) of the orally administered docetaxel is about 3,000 ng·h/mL to about 8,000 ng·h/mL.

In some embodiments, the AUC(0→∞) of the orally administered docetaxel is about 3,000 ng·h/mL to about 7,000 ng·h/mL.

In some embodiments, the AUC(0→∞) of the orally administered docetaxel is about 4,000 ng·h/mL to about 7,000 ng·h/mL.

In some embodiments, the AUC(0→∞) of the orally administered docetaxel is about 5,000 ng·h/mL to about 7,000 ng·h/mL.

In some embodiments, the AUC(0→∞) of the orally administered docetaxel is about 2,000 ng·h/mL.

In some embodiments, the AUC(0→∞) of the orally administered docetaxel is about 3,000 ng·h/mL.

In some embodiments, the AUC(0→∞) of the orally administered docetaxel is about 4,000 ng·h/mL.

In some embodiments, the AUC(0→∞) of the orally administered docetaxel is about 5,000 ng·h/mL.

In some embodiments, the AUC(0→∞) of the orally administered docetaxel is about 6,000 ng·h/mL.

In some embodiments, the AUC(0→∞) of the orally administered docetaxel is about 7,000 ng·h/mL.

In some embodiments, the AUC(0→∞) of the orally administered docetaxel is about 8,000 ng·h/mL.

In some embodiments, the AUC(0→∞) of the orally administered docetaxel is about 9,000 ng·h/mL.

In some embodiments, the AUC(0→∞) of the orally administered docetaxel is about 10,000 ng·h/mL.

In some embodiments, the total amount of the docetaxel orally administered per week is about 15 mg/m² to about 3,000 mg/m².

In some embodiments, the total amount of the docetaxel orally administered per week is about 25 mg/m² to about 2,500 mg/m².

In some embodiments, the total amount of the docetaxel orally administered per week is about 50 mg/m² to about 2,500 mg/m².

In some embodiments, the total amount of the docetaxel orally administered per week is about 75 mg/m² to about 2,500 mg/m².

In some embodiments, the total amount of the docetaxel orally administered per week is about 100 mg/m² to about 2,000 mg/m².

In some embodiments, the total amount of the docetaxel orally administered per week is about 150 mg/m² to about 2,000 mg/m².

In some embodiments, the total amount of the docetaxel orally administered per week is about 200 mg/m² to about 2,000 mg/m².

In some embodiments, the total amount of the docetaxel orally administered per week is about 250 mg/m² to about 2,000 mg/m².

In some embodiments, the total amount of the docetaxel orally administered per week is about 300 mg/m² to about 2,000 mg/m².

In some embodiments, the total amount of the docetaxel orally administered per week is about 300 mg/m² to about 1,900 mg/m².

In some embodiments, the total amount of the docetaxel orally administered per week is about 300 mg/m² to about 1,800 mg/m².

In some embodiments, the total amount of the docetaxel orally administered per week is about 300 mg/m² to about 1,700 mg/m².

In some embodiments, the total amount of the docetaxel orally administered per week is about 300 mg/m² to about 1,600 mg/m².

In some embodiments, the total amount of the docetaxel orally administered per week is about 300 mg/m² to about 1,500 mg/m².

In some embodiments, the total amount of the docetaxel orally administered per week is about 300 mg/m² to about 1,400 mg/m².

In some embodiments, the total amount of the docetaxel orally administered per week is about 300 mg/m² to about 1,300 mg/m².

In some embodiments, the total amount of the docetaxel orally administered per week is about 300 mg/m² to about 1,200 mg/m².

In some embodiments, the total amount of the docetaxel orally administered per week is about 300 mg/m² to about 1,100 mg/m².

In some embodiments, the total amount of the docetaxel orally administered per week is about 300 mg/m² to about 1,000 mg/m².

In some embodiments, the total amount of the docetaxel orally administered per week is about 300 mg/m² to about 900 mg/m².

In some embodiments, the total amount of the docetaxel orally administered per week is about 350 mg/m² to about 850 mg/m².

In some embodiments, the total amount of the docetaxel orally administered per week is about 400 mg/m² to about 800 mg/m².

In some embodiments, the total amount of the docetaxel orally administered per week is about 450 mg/m² to about 750 mg/m².

In some embodiments, the total amount of the docetaxel orally administered per week is about 500 mg/m² to about 700 mg/m².

In some embodiments, the total amount of the docetaxel orally administered per week is about 550 mg/m² to about 650 mg/m².

In some embodiments, the total amount of the docetaxel orally administered per week is about 15, 25, 50, 75, 100, 150, 200, 250, 300, 325, 350, 375, 400, 425, 450, 475, 500, 525, 550, 575, 600, 605, 610, 615, 620, 625, 630, 635, 640, 645, 650, 655, 660, 665, 670, 675, 680, 685, 690, 695, 700, 725, 750, 775, 800, 825, 850, 875, 900, 925, 950, 975, 1,000, 1,025, 1,050, 1,075, 1,100, 1,125, 1,150, 1,175, 1,200, 1,225, 1,250, 1,275, 1,300, 1,325, 1,350, 1,375, 1,400, 1,425, 1,450, 1,475, 1,500, 1,525, 1,550, 1,575, 1,600, 1,625, 1,650, 1,675, 1,700, 1,725, 1,750, 1,775, or 1,800 mg/m$^2$.

In some embodiments, the total amount of the docetaxel orally administered per week is at least about 25 mg/m$^2$ (e.g., at least 25 mg/m$^2$).

In some embodiments, the total amount of the docetaxel orally administered per week is at least about 50 mg/m$^2$ (e.g., at least 50 mg/m$^2$).

In some embodiments, the total amount of the docetaxel orally administered per week is at least about 75 mg/m$^2$ (e.g., at least 75 mg/m$^2$).

In some embodiments, the total amount of the docetaxel orally administered per week is at least about 100 mg/m$^2$ (e.g., at least 100 mg/m$^2$).

In some embodiments, the total amount of the docetaxel orally administered per week is at least about 125 mg/m$^2$ (e.g., at least 125 mg/m$^2$).

In some embodiments, the total amount of the docetaxel orally administered per week is at least about 150 mg/m$^2$ (e.g., at least 150 mg/m$^2$).

In some embodiments, the total amount of the docetaxel orally administered per week is at least about 175 mg/m$^2$ (e.g., at least 175 mg/m$^2$).

In some embodiments, the total amount of the docetaxel orally administered per week is at least about 200 mg/m$^2$ (e.g., at least 200 mg/m$^2$).

In some embodiments, the total amount of the docetaxel orally administered per week is at least about 225 mg/m$^2$ (e.g., at least 225 mg/m$^2$).

In some embodiments, the total amount of the docetaxel orally administered per week is at least about 250 mg/m$^2$ (e.g., at least 250 mg/m$^2$).

In some embodiments, the total amount of the docetaxel orally administered per week is at least about 275 mg/m$^2$ (e.g., at least 275 mg/m$^2$).

In some embodiments, the total amount of the docetaxel orally administered per week is at least about 300 mg/m$^2$ (e.g., at least 300 mg/m$^2$).

In some embodiments, the total amount of the docetaxel orally administered per week is at least about 325 mg/m$^2$ (e.g., at least 325 mg/m$^2$).

In some embodiments, the total amount of the docetaxel orally administered per week is at least about 350 mg/m$^2$ (e.g., at least 350 mg/m$^2$).

In some embodiments, the total amount of the docetaxel orally administered per week is at least about 375 mg/m$^2$ (e.g., at least 375 mg/m$^2$).

In some embodiments, the total amount of the docetaxel orally administered per week is at least about 400 mg/m$^2$ (e.g., at least 400 mg/m$^2$).

In some embodiments, the total amount of the docetaxel orally administered per week is at least about 425 mg/m$^2$ (e.g., at least 425 mg/m$^2$).

In some embodiments, the total amount of the docetaxel orally administered per week is at least about 450 mg/m$^2$ (e.g., at least 450 mg/m$^2$).

In some embodiments, the total amount of the docetaxel orally administered per week is at least about 475 mg/m$^2$ (e.g., at least 475 mg/m$^2$).

In some embodiments, the total amount of the docetaxel orally administered per week is at least about 500 mg/m$^2$ (e.g., at least 500 mg/m$^2$).

In some embodiments, the total amount of the docetaxel orally administered per week is at least about 525 mg/m$^2$ (e.g., at least 525 mg/m$^2$).

In some embodiments, the total amount of the docetaxel orally administered per week is at least about 550 mg/m$^2$ (e.g., at least 550 mg/m$^2$).

In some embodiments, the total amount of the docetaxel orally administered per week is at least about 575 mg/m$^2$ (e.g., at least 575 mg/m$^2$).

In some embodiments, the total amount of the docetaxel orally administered per week is at least about 600 mg/m$^2$ (e.g., at least 600 mg/m$^2$).

In some embodiments, the total amount of the docetaxel orally administered per week is at least about 615 mg/m$^2$ (e.g., at least 615 mg/m$^2$).

In some embodiments, the total amount of the docetaxel orally administered per week is at least about 625 mg/m$^2$ (e.g., at least 625 mg/m$^2$).

In some embodiments, the total amount of the docetaxel orally administered per week is at least about 630 mg/m$^2$ (e.g., at least 630 mg/m$^2$).

In some embodiments, the total amount of the docetaxel orally administered per week is at least about 645 mg/m$^2$ (e.g., at least 645 mg/m$^2$).

In some embodiments, the total amount of the docetaxel orally administered per week is at least about 650 mg/m$^2$ (e.g., at least 650 mg/m$^2$).

In some embodiments, the total amount of the docetaxel orally administered per week is at least about 660 mg/m$^2$ (e.g., at least 660 mg/m$^2$).

In some embodiments, the total amount of the docetaxel orally administered per week is at least about 675 mg/m$^2$ (e.g., at least 675 mg/m$^2$).

In some embodiments, the total amount of the docetaxel orally administered per week is at least about 700 mg/m$^2$ (e.g., at least 700 mg/m$^2$).

In some embodiments, the total amount of the docetaxel orally administered per week is at least about 725 mg/m$^2$ (e.g., at least 725 mg/m$^2$).

In some embodiments, the total amount of the docetaxel orally administered per week is at least about 750 mg/m$^2$ (e.g., at least 750 mg/m$^2$).

In some embodiments, the total amount of the docetaxel orally administered per week is at least about 775 mg/m$^2$ (e.g., at least 775 mg/m$^2$).

In some embodiments, the total amount of the docetaxel orally administered per week is at least about 800 mg/m$^2$ (e.g., at least 800 mg/m$^2$).

In some embodiments, the total amount of the docetaxel orally administered per week is at least about 825 mg/m$^2$ (e.g., at least 825 mg/m$^2$).

In some embodiments, the total amount of the docetaxel orally administered per week is at least about 850 mg/m$^2$ (e.g., at least 850 mg/m$^2$).

In some embodiments, the total amount of the docetaxel orally administered per week is at least about 875 mg/m$^2$ (e.g., at least 875 mg/m$^2$).

In some embodiments, the total amount of the docetaxel orally administered per week is at least about 900 mg/m$^2$ (e.g., at least 900 mg/m$^2$).

In some embodiments, the total amount of the docetaxel orally administered per week is at least about 975 mg/m$^2$ (e.g., at least 975 mg/m$^2$).

In some embodiments, the total amount of the docetaxel orally administered per week is at least about 1,000 mg/m$^2$ (e.g., at least 1,000 mg/m$^2$).

In some embodiments, the total amount of the docetaxel orally administered per week is at least about 1,050 mg/m$^2$ (e.g., at least 1,050 mg/m$^2$).

In some embodiments, the total amount of the docetaxel orally administered per week is at least about 1,100 mg/m$^2$ (e.g., at least 1,100 mg/m$^2$).

In some embodiments, the total amount of the docetaxel orally administered per week is at least about 1,125 mg/m$^2$ (e.g., at least 1,125 mg/m$^2$).

In some embodiments, the total amount of the docetaxel orally administered per week is at least about 1,200 mg/m$^2$ (e.g., at least 1,200 mg/m$^2$).

In some embodiments, the total amount of the docetaxel orally administered per week is at least about 1,250 mg/m$^2$ (e.g., at least 1,250 mg/m$^2$).

In some embodiments, the total amount of the docetaxel orally administered per week is at least about 1,300 mg/m$^2$ (e.g., at least 1,300 mg/m$^2$).

In some embodiments, the total amount of the docetaxel orally administered per week is at least about 1,350 mg/m$^2$ (e.g., at least 1,350 mg/m$^2$).

In some embodiments, the total amount of the docetaxel orally administered per week is at least about 1,375 mg/m$^2$ (e.g., at least 1,375 mg/m$^2$).

In some embodiments, the total amount of the docetaxel orally administered per week is at least about 1,400 mg/m$^2$ (e.g., at least 1,400 mg/m$^2$).

In some embodiments, the total amount of the docetaxel orally administered per week is at least about 1,500 mg/m$^2$ (e.g., at least 1,500 mg/m$^2$).

In some embodiments, the total amount of the docetaxel orally administered per week is at least about 1,625 mg/m$^2$ (e.g., at least 1,625 mg/m$^2$).

In some embodiments, the total amount of the docetaxel orally administered per week is at least about 1,650 mg/m$^2$ (e.g., at least 1,650 mg/m$^2$).

In some embodiments, the total amount of the docetaxel orally administered per week is at least about 1,750 mg/m$^2$ (e.g., at least 1,750 mg/m$^2$).

In some embodiments, the total amount of the docetaxel orally administered per week is at least about 1,800 mg/m$^2$ (e.g., at least 1,800 mg/m$^2$).

In some embodiments, the AUC(0→∞) of the orally administered docetaxel is equal to or greater than the AUC (0→∞) of intravenously administered docetaxel (e.g., Taxotere® or docetaxel formulated with polysorbate 80) at an amount of about 60-100 mg/m$^2$ (e.g., 75 mg/m$^2$) over a period of about 60 minutes once every three weeks, or at an amount of about 30-100 mg/m$^2$ (e.g., 50 mg/m$^2$) over a period of about 60 minutes once every two weeks, or at an amount of about 30-75 mg/m$^2$ (e.g., 30 mg/m$^2$) in treating cancer.

In some embodiments, the AUC(0→∞) of the orally administered docetaxel is equal to or greater than the AUC (0→∞) of intravenously administered docetaxel (e.g., Taxotere® or docetaxel formulated with polysorbate 80) at an amount of about 70-90 mg/m$^2$ over a period of about 60 minutes once every three weeks in treating cancer.

In some embodiments, the AUC(0→∞) of the orally administered docetaxel is equal to or greater than the AUC (0→∞) of intravenously administered docetaxel (e.g., Taxotere® or docetaxel formulated with polysorbate 80) at an amount of about 75-85 mg/m$^2$ over a period of about 60 minutes once every three weeks in treating cancer.

In some embodiments, the AUC(0→∞) of the orally administered docetaxel is equal to or greater than the AUC (0→∞) of intravenously administered docetaxel (e.g., Taxotere® or docetaxel formulated with polysorbate 80) at an amount of about 80 mg/m$^2$ over a period of about 60 minutes once every three weeks in treating cancer.

In some embodiments, the AUC(0→∞) of the orally administered docetaxel is equal to or greater than the AUC (0→∞) of intravenously administered docetaxel (e.g., Taxotere® or docetaxel formulated with polysorbate 80) at an amount of about 75 mg/m$^2$ over a period of about 60 minutes once every three weeks in treating cancer.

In some embodiments, the disclosure provides methods of treating cancer in a subject, and/or to methods for reducing or preventing toxicity, hypersensitivity-type infusion reactions and other negative outcomes resulting from or associated with intravenously administered docetaxel (e.g., Taxotere® or docetaxel formulated with polysorbate 80) therapy in a subject suffering from cancer.

In some embodiments, the present disclosure provides Compound A for use in the treatment of cancer in a subject, and/or to Compound A for use in the reducing or preventing toxicity, hypersensitivity-type infusion reactions and other negative outcomes resulting from or associated with intravenously administered docetaxel (e.g., Taxotere® or docetaxel formulated with polysorbate 80) therapy in a subject suffering from cancer.

In some embodiments, the present disclosure provides use of Compound A in the manufacture of a medicament for use with docetaxel in the treatment of cancer in a subject, and/or to use of Compound A in the manufacture of a medicament for use with docetaxel in reducing or preventing toxicity, hypersensitivity-type infusion reactions and other negative outcomes resulting from or associated with intravenously administered docetaxel (e.g., Taxotere® or docetaxel formulated with polysorbate 80) therapy in a subject suffering from cancer.

In some embodiments, the present disclosure provides use of Compound A with docetaxel for the treatment of cancer in a subject, and/or to use of Compound A with docetaxel for reducing or preventing toxicity, hypersensitivity-type infusion reactions and other negative outcomes resulting from or associated with intravenously administered docetaxel (e.g., Taxotere® or docetaxel formulated with polysorbate 80) therapy in a subject suffering from cancer.

In some embodiments, the present disclosure provides use of Compound A in a combination therapy with docetaxel for treatment of cancer in a subject, and/or to use of Compound A in a combination therapy with docetaxel for reducing or preventing toxicity, hypersensitivity-type infusion reactions and other negative outcomes resulting from or associated with intravenously administered docetaxel (e.g., Taxotere® or docetaxel formulated with polysorbate 80) therapy in a subject suffering from cancer.

In some embodiments, the present disclosure provides use of a medicament in a combination therapy with docetaxel for the treatment of cancer in a subject, and/or use of a medicament in a combination therapy with docetaxel for the reducing or preventing toxicity, hypersensitivity-type infusion reactions and other negative outcomes resulting from or associated with intravenously administered docetaxel (e.g., Taxotere® or docetaxel formulated with polysorbate 80) therapy in a subject suffering from cancer, wherein the medicament comprises Compound A.

In some embodiments, the intravenously administered docetaxel is formulated in compositions that comprise docetaxel and a pharmaceutical excipient or carrier that facilitates the intravenous administration of docetaxel. In some embodiments, the intravenously administered docetaxel is formulated with polysorbate 80, e.g., Tween 80®. In some embodiments, the intravenously administered docetaxel is Taxol®, or a generic version thereof. In some embodiments, the intravenously administered docetaxel is formulated with a protein carrier. In some embodiments, the intravenously administered docetaxel is formulated in a composition comprising protein-bound docetaxel, (i.e., nab-docetaxel or ABI-008).

In some embodiments, the cancer is a disease that involves abnormal cell growth with the potential to invade or spread to other parts of the body.

In some embodiments, the cancer is a malignant tumor or neoplasm.

In some embodiments, the cancer is breast cancer, pancreatic cancer, non-small cell lung cancer, ovarian cancer, AIDS-related Kaposi sarcoma, soft tissue sarcoma, esophageal cancer, melanoma, lymphoma, uterine cancer, peritoneal cancer, fallopian tube cancer, endometrial cancer, cervical cancer, thyroid cancer, gastric cancer, gastroesophageal junction cancer, urothelial cancer, bladder cancer, oropharynx cancer, hypopharynx cancer, larynx cancer, head and neck cancer, germ cell cancer/tumors, prostate cancer, colon cancer, rectal cancer, kidney cancer, squamous cell carcinoma, leukemia, or non-Hodgkin lymphoma.

In some embodiments, the cancer is breast cancer, pancreatic cancer, non-small cell lung cancer, ovarian cancer, AIDS-related Kaposi sarcoma, esophageal cancer, melanoma, lymphoma, uterine cancer, peritoneal cancer, fallopian tube cancer, endometrial cancer, cervical cancer, thyroid cancer, gastric cancer, gastroesophageal junction cancer, urothelial cancer, bladder cancer, oropharynx cancer, hypopharynx cancer, larynx cancer, head and neck cancer, or germ cell cancer/tumors.

In some embodiments, the cancer is breast cancer, non-small cell lung cancer, ovarian cancer, AIDS-related Kaposi sarcoma, esophageal cancer, bladder cancer, prostate cancer, or melanoma.

In some embodiments, the cancer is breast cancer, non-small cell lung cancer, ovarian cancer, or AIDS-related Kaposi sarcoma.

In some embodiments, the cancer is breast cancer. In some embodiments, the breast cancer is metastatic breast cancer. In some embodiments, the breast cancer is carcinoma of the breast.

In some embodiments, the cancer is lung cancer. In some embodiments, the lung cancer is non-small cell lung cancer.

In some embodiments, the cancer is prostate cancer. In some embodiments, the prostate cancer is metastatic hormone resistant prostate cancer, castration naïve prostate cancer, or castration resistant prostate cancer. In some embodiments, the prostate cancer is metastatic hormone resistant prostate cancer. In some embodiments, the prostate cancer is carcinoma of the prostate.

In some embodiments, the cancer is ovarian cancer. In some embodiments, the cancer is carcinoma of the ovary.

In some embodiments, the cancer is AIDS-related Kaposi sarcoma.

In some embodiments, the cancer is pancreatic cancer. In some embodiments, the pancreatic cancer is adenocarcinoma of the pancreas.

In some embodiments, the cancer is bladder cancer, breast cancer, cervical cancer, esophageal cancer, gastric cancer, epithelial ovarian cancer, fallopian tube cancer, primary peritoneal cancer, head and neck cancer, squamous cell carcinoma of the head and neck (SCCHN), non-small cell lung cancer (NSCLC), castration naïve prostate cancer, castration resistant prostate cancer, metastatic hormone resistant prostate cancer (mHRPC), small cell lung cancer, soft tissue sarcoma, or uterine cancer.

In some embodiments, the cancer is breast cancer, non-small cell lung cancer, prostate cancer (including metastatic hormone resistant prostate cancer, castration naïve prostate cancer, or castration resistant prostate cancer), squamous cell carcinoma of the head and neck, or gastric cancer.

In some embodiments, the cancer is bladder cancer, cervical cancer, ovarian cancer, epithelial ovarian cancer, fallopian tube cancer, peritoneal cancer, esophageal cancer, soft tissue sarcoma, leiomyosarcoma, uterine cancer, pancreatic cancer, or endometrial cancer.

In some embodiments, the cancer is an advanced malignancy. In some embodiments, the cancer is a primary or secondary cancer.

In some embodiments, the methods of the disclosure include a method for treating metastatic breast cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the methods of the present disclosure include a method for treating metastatic breast cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the methods of the present disclosure include a method for treating non-small cell lung cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the methods of the present disclosure include a method for treating non-small cell lung cancer in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the methods of the present disclosure include a method for treating prostate cancer (e.g., metastatic hormone resistant prostate cancer, castration naïve prostate cancer, or castration resistant prostate cancer) in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the methods of the present disclosure include a method for treating prostate cancer (e.g., metastatic hormone resistant prostate cancer, castration naïve prostate cancer, or castration resistant prostate cancer) in a subject in need thereof, wherein the plasma exposure of the orally administered docetaxel, as measured by AUC (0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the methods of the present disclosure include a method for treating adenocarcinoma of the pancreas in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the methods of the present disclosure include a method for treating adenocarcinoma of the pancreas in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the methods of the present disclosure include a method for treating carcinoma of the ovary in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the methods of the present disclosure include a method for treating carcinoma of the ovary in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the methods of the present disclosure include a method for treating carcinoma of the breast in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the methods of the present disclosure include a method for treating carcinoma of the breast in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the methods of the present disclosure include a method for treating AIDS-related Kaposi's Sarcoma in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the methods of the present disclosure include a method for treating AIDS-related Kaposi's Sarcoma in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in treating metastatic breast cancer in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the present disclosure pertains to Compound A for use with docetaxel in treating metastatic breast cancer in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in treating non-small cell lung cancer in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the present disclosure pertains to Compound A for use with docetaxel in treating non-small cell lung cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in treating adenocarcinoma of the pancreas in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the present disclosure pertains to Compound A for use with docetaxel in treating adenocarcinoma of the pancreas in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in treating carcinoma of the ovary in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the present disclosure pertains to Compound A for use with docetaxel in treating carcinoma of the ovary in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in treating carcinoma of the breast in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the present disclosure pertains to Compound A for use with docetaxel in treating carcinoma of the breast in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in treating AIDS-related Kaposi's Sarcoma in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the present disclosure pertains to Compound A for use with docetaxel in treating AIDS-related Kaposi's Sarcoma in a subject in need thereof, wherein the plasma exposure of the orally administered docetaxel, as measured by AUC$_{(0→∞)}$, is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the present disclosure pertains to use of Compound A in the manufacture of a medicament for use with docetaxel for treating metastatic breast cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m$^2$ (e.g., 75 mg/m$^2$) over a period of about 1 to 24 hours once every three weeks.

In some embodiments, the present disclosure pertains to use of Compound A in the manufacture of a medicament for use with docetaxel for treating metastatic breast cancer in a subject in need thereof, wherein the plasma exposure of the orally administered docetaxel, as measured by AUC$_{(0→∞)}$, is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m$^2$, about 70-90 mg/m$^2$, about 75-85 mg/m$^2$, about 80 mg/m$^2$, or about 75 mg/m$^2$ over a period of about 1 to 24 hours, about 1 to 20 hours, about 1-16 hours, about 2-12 hours, or about 3-8 hours once every three weeks.

In some embodiments, the present disclosure pertains to use of Compound A in the manufacture of a medicament for use with docetaxel for treating non-small cell lung cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to use of Compound A in the manufacture of a medicament for use with docetaxel for treating non-small cell lung cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to use of Compound A in the manufacture of a medicament for use with docetaxel for treating adenocarcinoma of the pancreas in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to use of Compound A in the manufacture of a medicament for use with docetaxel for treating adenocarcinoma of the pancreas in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to use of Compound A in the manufacture of a medicament for use with docetaxel for treating carcinoma of the ovary in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to use of Compound A in the manufacture of a medicament for use with docetaxel for treating carcinoma of the ovary in a subject in need thereof, wherein the plasma exposure of the orally administered docetaxel, as measured by $AUC_{(0 \to \infty)}$, is equal to or greater than the plasma exposure, as measured by $AUC_{(0 \to \infty)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to use of Compound A in the manufacture of a medicament for use with docetaxel for treating carcinoma of the breast in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to use of Compound A in the manufacture of a medicament for use with docetaxel for treating carcinoma of the breast in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to use of Compound A in the manufacture of a medicament for use with docetaxel for treating AIDS-related Kaposi's Sarcoma in a subject in need thereof, wherein the plasma exposure of the orally administered docetaxel, as measured by $AUC_{(0 \to \infty)}$, is equal to or greater than the plasma exposure, as measured by $AUC_{(0 \to \infty)}$, of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to use of Compound A in the manufacture of a medicament for use with docetaxel for treating AIDS-related Kaposi's Sarcoma in a subject in need thereof, wherein the plasma exposure of the orally administered docetaxel, as measured by $AUC_{(0 \to \infty)}$, is equal to or greater than the plasma exposure, as measured by $AUC_{(0 \to \infty)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in the treatment of metastatic breast cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to Compound A for use with docetaxel in the treatment of metastatic breast cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in the treatment of non-small cell lung cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to Compound A for use with docetaxel in the treatment of non-small cell lung cancer in a subject in need thereof, wherein the plasma exposure of the orally administered docetaxel, as measured by AUC(0→∞), is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in the treatment of adenocarcinoma of the pancreas in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to Compound A for use with docetaxel in the treatment of adenocarcinoma of the pancreas in a subject in need thereof, wherein the plasma exposure of the orally administered docetaxel, as measured by $AUC_{(0\to\infty)}$, is equal to or greater than the plasma exposure, as measured by AUC(0→∞), of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in the treatment of g carcinoma of the ovary in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to Compound A for use with docetaxel in the treatment of carcinoma of the ovary in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in the treatment of carcinoma of the breast in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to Compound A for use with docetaxel in the treatment of carcinoma of the breast in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use with docetaxel in the treatment of AIDS-related Kaposi's Sarcoma in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to Compound A for use with docetaxel in the treatment of AIDS-related Kaposi's Sarcoma in a subject in need thereof, wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use in a combination therapy with docetaxel in the treatment of metastatic breast cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to Compound A for use in a combination therapy with docetaxel in the treatment of metastatic breast cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use in a combination therapy with docetaxel in the treatment of non-small cell lung cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains Compound A for use in a combination therapy with docetaxel in the treatment of non-small cell lung cancer in a subject in need thereof, wherein the plasma exposure of the orally administered docetaxel, as measured by AUC(0→∞), is equal to or greater than the plasma exposure, as measured by $AUC_{(0→∞)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use in a combination therapy with docetaxel in the treatment of adenocarcinoma of the pancreas in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to Compound A for use in a combination therapy with docetaxel in the treatment of adenocarcinoma of the pancreas in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use in a combination therapy with docetaxel in the treatment of g carcinoma of the ovary in a subject in need thereof, wherein the plasma exposure of the orally administered docetaxel, as measured by AUC(0→∞), is equal to or greater than the plasma exposure, as measured by $AUC_{(0→∞)}$, of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to Compound A for use in a combination therapy with docetaxel in the treatment of carcinoma of the ovary in a subject in need thereof, wherein the plasma exposure of the orally administered docetaxel, as measured by AUC(0→∞), is equal to or greater than the plasma exposure, as measured by $AUC_{(0→∞)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use in a combination therapy with docetaxel in the treatment of carcinoma of the breast in a subject in need thereof, wherein the plasma exposure of the orally administered docetaxel, as measured by $AUC_{(0→∞)}$, is equal to or greater than the plasma exposure, as measured by $AUC_{(0→∞)}$, of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to Compound A for use in a combination therapy with docetaxel in the treatment of carcinoma of the breast in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to Compound A for use in a combination therapy with docetaxel in the treatment of AIDS-related Kaposi's Sarcoma in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to Compound A for use in a combination therapy with docetaxel in the treatment of AIDS-related Kaposi's Sarcoma in a subject in need thereof, wherein the plasma exposure of the orally administered docetaxel, as measured by $AUC_{(0→∞)}$, is equal to or greater than the plasma exposure, as measured by $AUC_{(0→∞)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to a medicament comprising Compound A for use in a combination therapy with docetaxel in the treatment of metastatic breast cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to a medicament comprising Compound A for use in a combination therapy with docetaxel in the treatment of metastatic breast cancer in a subject in need thereof, wherein the plasma exposure of the orally administered docetaxel, as measured by AUC(0→∞), is equal to or greater than the plasma exposure, as measured by AUC(0→∞), of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to a medicament comprising Compound A for use in a combination therapy with docetaxel in the treatment of non-small cell lung cancer in a subject in need thereof, wherein the plasma exposure of the orally administered docetaxel, as measured by AUC(0→∞), is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to a medicament comprising Compound A for use in a combination therapy with docetaxel in the treatment of non-small cell lung cancer in a subject in need thereof, wherein the plasma exposure of the orally administered docetaxel, as measured by AUC$_{(0→∞)}$, is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to a medicament comprising Compound A for use in a combination therapy with docetaxel in the treatment of adenocarcinoma of the pancreas in a subject in need thereof, wherein the plasma exposure of the orally administered docetaxel, as measured by AUC$_{(0→∞)}$, is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to a medicament comprising Compound A for use in a combination therapy with docetaxel in the treatment of adenocarcinoma of the pancreas in a subject in need thereof, wherein the plasma exposure of the orally administered docetaxel, as measured by AUC$_{(0→∞)}$, is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to a medicament comprising Compound A for use in a combination therapy with docetaxel in the treatment of carcinoma of the ovary in a subject in need thereof, wherein the plasma exposure of the orally administered docetaxel, as measured by AUC$_{(0→∞)}$, is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to a medicament comprising Compound A for use in a combination therapy with docetaxel in the treatment of carcinoma of the ovary in a subject in need thereof, wherein the plasma exposure of the orally administered docetaxel, as measured by AUC$_{(0→∞)}$, is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to a medicament comprising Compound A for use in a combination therapy with docetaxel in the treatment of carcinoma of the breast in a subject in need thereof, wherein the plasma exposure of the orally administered docetaxel, as measured by AUC$_{(0→∞)}$, is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to a medicament comprising Compound A for use in a combination therapy with docetaxel in the treatment of carcinoma of the breast in a subject in need thereof, wherein the plasma exposure of the orally administered docetaxel, as measured by AUC$_{(0→∞)}$, is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the present disclosure pertains to a medicament comprising Compound A for use in a combination therapy with docetaxel in the treatment of AIDS-related Kaposi's Sarcoma in a subject in need thereof, wherein the plasma exposure of the orally administered docetaxel, as measured by AUC$_{(0→∞)}$, is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m² (e.g., 75 mg/m²) over a period of about 1 to 24 hours once every three weeks.

In some embodiments, the present disclosure pertains to a medicament comprising Compound A for use in a combination therapy with docetaxel in the treatment of AIDS-related Kaposi's Sarcoma in a subject in need thereof, wherein the plasma exposure of the orally administered docetaxel, as measured by AUC$_{(0→∞)}$, is equal to or greater than the plasma exposure, as measured by AUC$_{(0→∞)}$, of intravenously administered docetaxel (e.g., Taxotere® or docetaxel formulated with polysorbate 80) at an amount of about 60-100 mg/m², about 70-90 mg/m², about 75-85 mg/m², about 80 mg/m², or about 75 mg/m² over a period of about 1 to 24 hours, about 1 to 20 hours, about 1-16 hours, about 2-12 hours, or about 3-8 hours once every three weeks.

In some embodiments, the subject is fasted before docetaxel and/or Compound A is orally administered. In some embodiments, the subject is fasted for at least 3 hours, at least 4 hours, at least 6 hours, at least 8 hours, at least 12 hours, at least 18 hours, or at least 24 hours. In some embodiments, the subject is fasted for at least 12 hours, at least 18 hours, or at least 24 hours before docetaxel and/or Compound A is orally administered.

Unless explicitly indicated otherwise, the terms "approximately" and "about" are synonymous. In some embodiments, "approximately" and "about" refer to the recited amount, dose, value (for example, $AUC_{(0\to\infty)}$), or duration ±20%, ±15%, ±10%, ±8%, ±6%, ±5%, ±4%, ±2%, ±1%, or ±0.5%. In another embodiment, "approximately" and "about" refer to the listed amount, value, or duration ±10%, ±8%, ±6%, ±5%, ±4%, or ±2%. In yet another embodiment, "approximately" and "about" refer to the listed amount, value, or duration ±5%. In yet another embodiment, "approximately" and "about" refer to the listed amount, value, or duration ±2%. In yet another embodiment, "approximately" and "about" refer to the listed amount, value, or duration ±1%. When the terms "approximately" and "about" are used when reciting temperature or temperature range, these terms refer to the recited temperature or temperature range ±5° C., ±2° C., or ±1° C. In another embodiment, the terms "approximately" and "about" refer to the recited temperature or temperature range ±2° C.

The term "docetaxel" refers to (2aR,4S,4aS,6R,9S,11S, 12S,12aR,12b S)-12b-acetoxy-9-(((2R,3S)-3-((tert-butoxycarbonyl)amino)-2-hydroxy-3-phenylpropanoyl)oxy)-4,6, 11-trihydroxy-4a,8,13,13-tetramethyl-5-oxo-2a,3,4,4a,5,6, 9,10,11,12,12a, 12b-dodecahydro-1H-7,11-methanocyclodeca[3,4]benzo[1,2-b]oxet-12-yl benzoate or N-debenzoyl-N-tert-butoxycarbonyl-10-deacetyltaxol, CAS Number 114977-28-5, $C_{43}H_{53}NO_{14}$, i.e., the compound with the following structure:

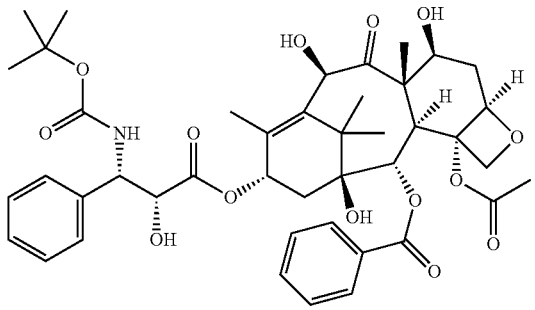

Unless otherwise indicated, the term "docetaxel" includes pharmaceutically acceptable salts and/or solvates thereof.

Docetaxel is of the chemotherapy drug class; taxane, and is a semi-synthetic analogue of paclitaxel (Taxol®), an extract from the bark of the rare Pacific yew tree, *Taxus brevifolia*. Docetaxel differs from paclitaxel at two positions in its chemical structure. It has a hydroxyl functional group on carbon 10, whereas paclitaxel has an acetate ester, and a tert-butyl carbamate ester exists on the phenylpropionate side chain instead of the benzamide in paclitaxel.

Docetaxel suitable for intravenous administration or intravenously administered docetaxel includes compositions that comprise docetaxel and a pharmaceutical excipient or carrier that facilitates the intravenous administration of docetaxel. Such pharmaceutical excipient or carrier includes polysorbate 80, e.g., Tween 80®. In some embodiments, the docetaxel suitable for intravenous administration or intravenously administered docetaxel includes the brand name product, TAXOTERE®, and generic versions thereof. In some embodiments, the docetaxel suitable for intravenous administration or intravenously administered docetaxel includes the brand name products, DOCEFREZ® or ZYTAX®, and generic versions thereof. In some embodiments, the docetaxel suitable for intravenous administration or intravenously administered docetaxel includes a composition comprising protein-bound docetaxel (i.e., nab-docetaxel or ABI-008).

Docetaxel suitable for oral administration or orally administered docetaxel refers to a formulation of docetaxel that is administered orally.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include microencapsulated active compound forms, optionally with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

In some embodiments, the orally administered docetaxel is in capsule form. In some embodiments, each capsule contains docetaxel and a surfactant, e.g., polysorbate 80. In some embodiments, each capsule contains 30 mg-200 mg of docetaxel. In some embodiments, each capsule contains 30 mg, 45 mg, 60 mg, 75 mg, 90 mg, 100 mg, 125 mg, 150 mg, 175 mg, or 200 mg of docetaxel. In some embodiments, each capsule contains 30 mg of docetaxel. In some embodiments, each capsule contains 500 mg of polysorbate 80. In some embodiments each capsule contains 30 mg of docetaxel and 500 mg of polysorbate 80. In some embodiments, the orally administered docetaxel is in tablet form. In some embodiments, each tablet contains 30 mg-200 mg of docetaxel. In some embodiments, each tablet contains 30 mg, 45 mg, 60 mg, 75 mg, 90 mg, 100 mg, 125 mg, 150 mg, 175 mg, or 200 mg of docetaxel. In some embodiments, each tablet contains 30 mg of docetaxel. In some embodiments, the orally administered docetaxel is in solution form. In some embodiments, each solution contains 30 mg-200 mg of docetaxel. In some embodiments, each solution contains 30 mg, 45 mg, 60 mg, 75 mg, 90 mg, 100 mg, 125 mg, 150 mg, 175 mg, or 200 mg of docetaxel. In some embodiments, each solution contains 30 mg of docetaxel.

Oral formulation of docetaxel (e.g., capsule, tablet, or solution) may be formulated by any suitable methods known in the art.

The term "Compound A" refers to a compound, or a pharmaceutically acceptable salt and/or solvate thereof, which is a P-gp pump inhibitor and has the following structure:

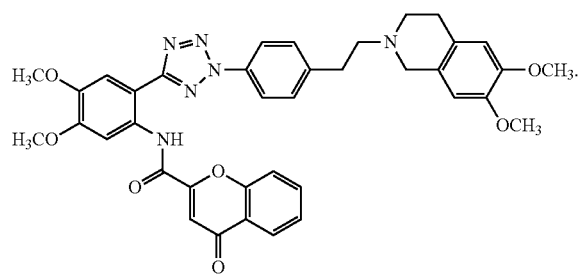 [SMILES: COc1cc2c(cc1OC)CN(CCc1ccc(-n3nnc(-c4cc(OC)c(OC)cc4NC(=O)c4cc(=O)c5ccccc5o4)n3)cc1)CC2]

Unless indicated otherwise, the terms "Compound A," "HM30181 methanesulfonate monohydrate," "HM30181A," "HM30181AK," and "HM30181AK-US" are all equivalent and are used interchangeably. In some embodiments, Compound A refers to a methanesulfonate salt monohydrate of Compound A:

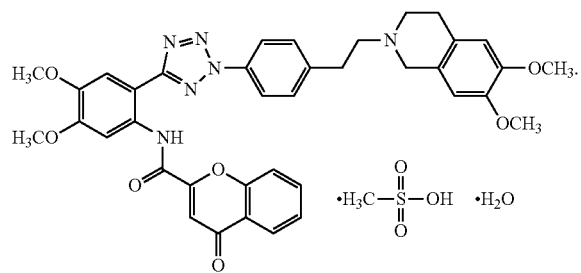

In some embodiments, Compound A refers to a methanesulfonate salt monohydrate of Compound A. Compound A is commercially available, e.g., in tablet form suitable for oral administration. In some embodiments, Compound A is administered in 15 mg tablets suitable for oral administration.

Compound A may be formulated by any suitable methods known in the art.

The term "subject" includes any living organism that has cancer or is at a risk of developing cancer. In some embodiments, the term "subject" refers to a mammal that has cancer or is at a risk of developing cancer. In some embodiments, the term subject refers to a human being that has cancer or is at a risk of developing cancer. In some embodiments, the term subject refers to a cancer patient, i.e., a patient.

The term "$AUC_{(0 \to \infty)}$" refers to the total exposure to a drug and is expressed in unit of concentration time. In some embodiments, it is the concentration of a drug over a time interval circulating in the body, e.g., in the plasma, blood, or serum. In some embodiments, $AUC_{(0 \to \infty)} = AUC_{(0 \to Tlast)} + (C_{Tlast}/K_{elim})$, where $C_{Tlast}$ is the last measureable measurable drug concentration and $K_{elim}$ is the terminal elimination rate constant, expressed in $time^{-1}$ units.

In some embodiments, $C_{Tlast}$ may be determined from about 1 day to about 21 days after oral administration of docetaxel.

In some embodiments, $C_{Tlast}$ may be determined from about 2 days to about 14 days after oral administration of docetaxel.

In some embodiments, $C_{Tlast}$ may be determined from about 3 days to about 7 days after oral administration of docetaxel.

In some embodiments, $C_{Tlast}$ may be determined at about 2 days after oral administration of docetaxel. In some embodiments, $C_{Tlast}$ may be determined at about 3 days after oral administration of docetaxel. In some embodiments, $C_{Tlast}$ may be determined at about 4 days after oral administration of docetaxel. In some embodiments, $C_{Tlast}$ may be determined at about 5 days after oral administration of docetaxel. In some embodiments, $C_{Tlast}$ may be determined at about 6 days after oral administration of docetaxel. In some embodiments, $C_{Tlast}$ may be determined at about 7 days after oral administration of docetaxel.

Hematologic toxicity associated with the intravenous administration of docetaxel in a subject suffering from cancer can be assessed by a medical professional or health care worker by analyzing blood samples in a subject, i.e., determining cell counts, including white blood cells, absolute neutrophils, platelets, and hemoglobin.

Hypersensitivity-type infusion reactions, and symptoms associated with hematologic toxicity and/or neurotoxicity associated with the intravenous administration of docetaxel in a subject suffering from cancer can be assessed by a medical professional or health care worker.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "QD" refers to every day, the term "Q1W" refers to every one week, the term "Q2W" refers to every two weeks, and the term "Q3W" refers to every three weeks.

The term "QD×2" refers to on day 1 and day 2 weekly, the term "QD×3" refers to on day 1-day 3 weekly, the term "QD×4" refers to on day 1-day 4 weekly, the term "QD×5" refers to on day 1-day 5 weekly, and the term "QD×6" refers to on day 1-day 6 weekly.

The term "oral docetaxel", as used herein, refers to docetaxel administered as oral formulations, as described herein, in combination with Compound A, as described herein.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active ingredient or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing docetaxel may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active ingredient into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating docetaxel in the required amount in an appropriate solvent with one or a combination of ingredients enumerated above, as required, followed by filtered sterilization. Generally, dispersions are prepared by incorporating form docetaxel into a sterile vehicle that contains a basic dispersion medium and the required other ingredients from those enumerated above. In the case of sterile powders for the preparation of sterile injectable solutions, methods of preparation are vacuum drying and freeze-drying that yields a powder of docetaxel plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, form can be incorporated with excipients and used in the form of tablets, troches, or capsules. Oral compositions can also be prepared using a fluid carrier for use as a mouthwash, wherein in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The pharmaceutical compositions described herein can be included in a container, pack, or dispenser together with instructions for administration.

All percentages and ratios used herein, unless otherwise indicated, are by weight.

Other features and advantages of the present disclosure are apparent from the different examples. The provided examples illustrate different components and methodology useful in practicing the present disclosure.

The examples do not limit the claimed disclosure. Based on the present disclosure the skilled artisan can identify and employ other components and methodology useful for practicing the present disclosure.

Examples

Example 1—Clinical Study of Orally Administered Docetaxel in Combination with Compound A in Comparison to IV Docetaxel A 2-part study was conducted in subjects with metastatic prostate cancer ("Study 1"). The initial stage included a 21-day cycle of IV administered docetaxel (at the dose prescribed for each participant as their prior final treatment with IV docetaxel). In the second part of this study, oral docetaxel, starting at 75 mg/m$^2$, 150 mg/m$^2$, or 225 mg/m$^2$ was administered as a single dose. A total of 5 (n=18) subjects enrolled in this study.

Figure 2:
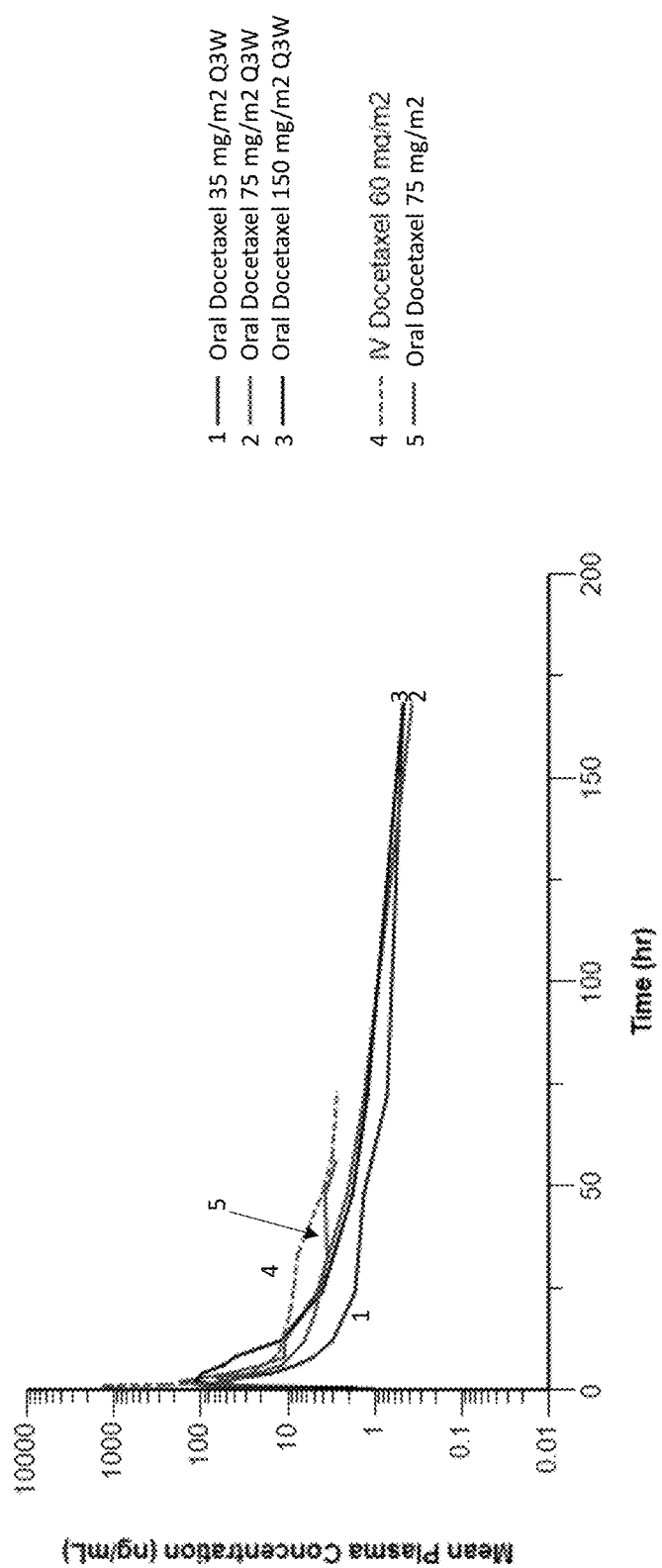
FIG. 2 is a graph showing the comparison of IV docetaxel and oral docetaxel (Mean Plasma Concentration (ng/mL) vs Time (hr)).
Figure 3A:
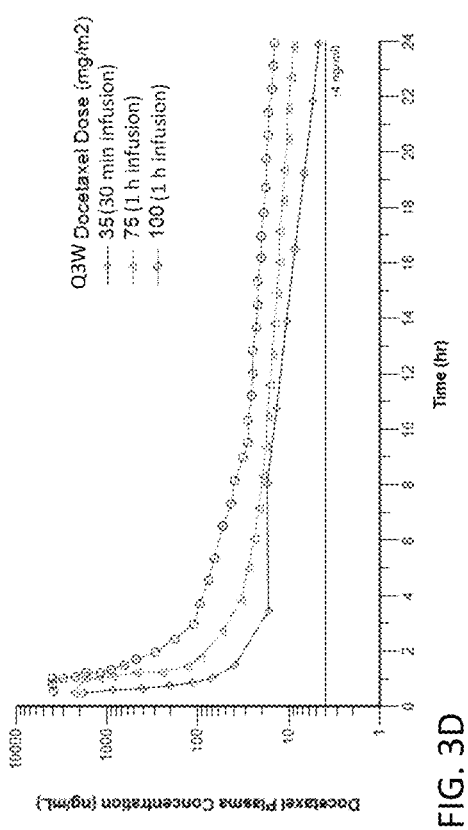
FIGS. 3A-3D are graphs showing the target concentration comparison for various IV docetaxel Regimens (35 mg/m$^2$, 75 mg/m$^2$, or 100 mg/m$^2$, each Q3W) for 0 to 25 hours (FIG. 3A and FIG. 3B) and for 0 to 500 hours (FIG. 3C and FIG. 3D).
Figure 3B:
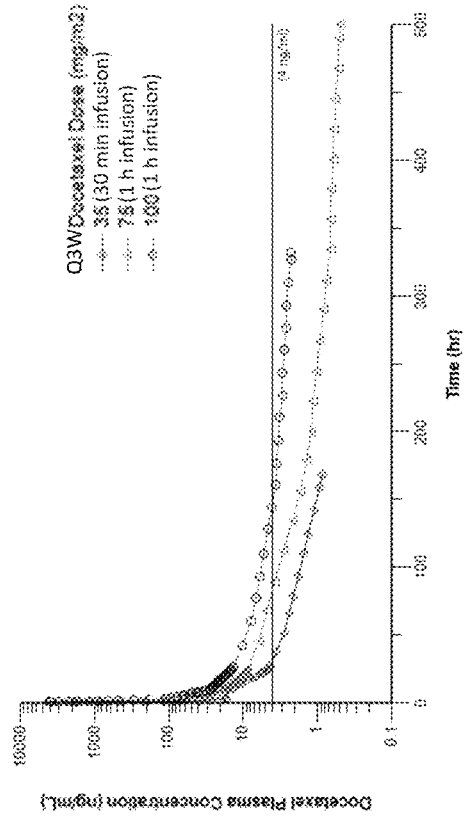
Figure 3C:
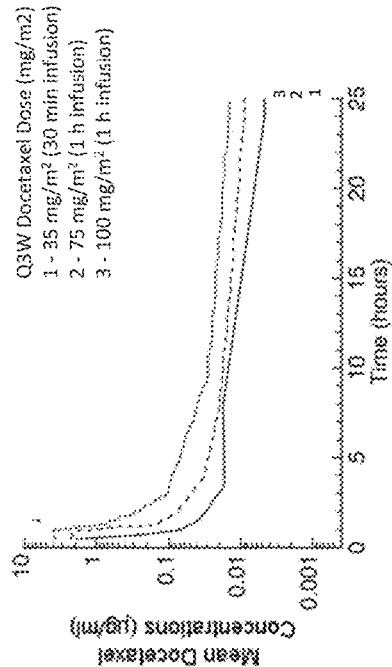
Figure 3D:
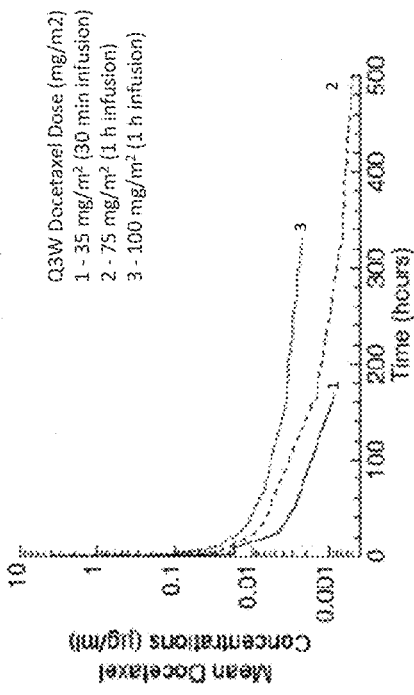
Figure 4:
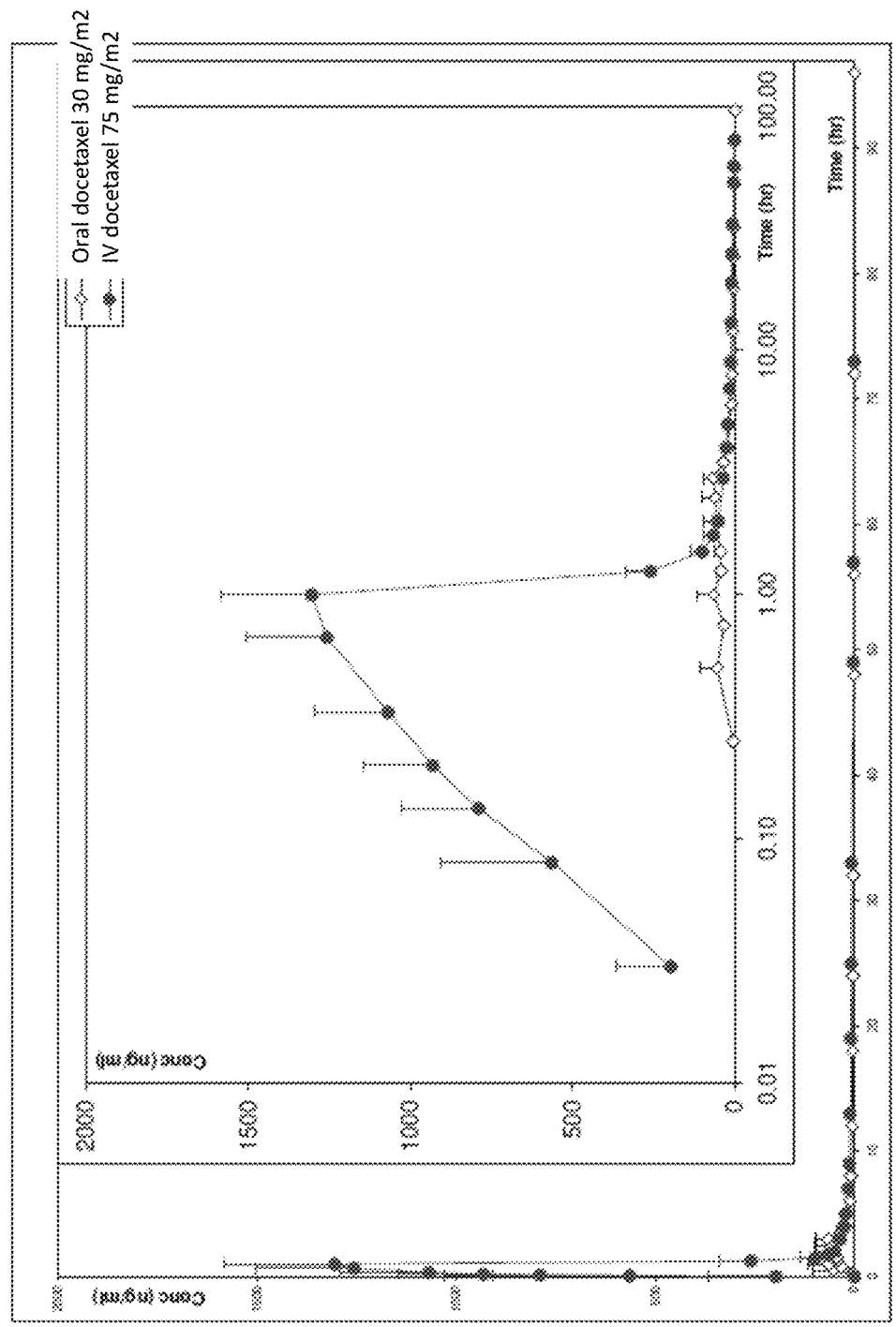
FIG. 4 is a graph showing the comparison of 30 mg oral docetaxel capsule study versus 75 mg IV docetaxel in Study 1.
Figure 5:
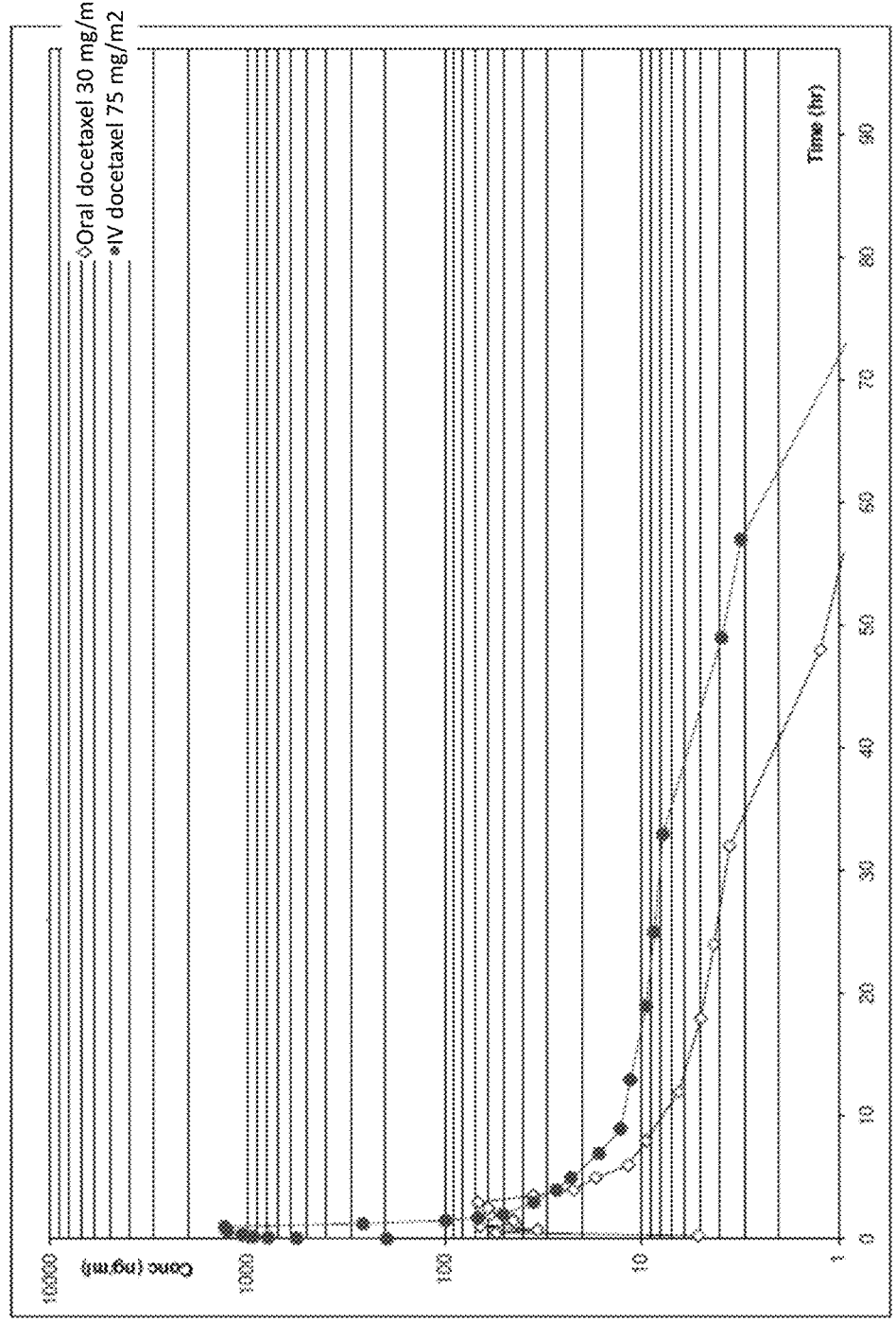
FIG. 5 is a graph showing the comparison of 30 mg oral docetaxel capsule study versus 75 mg IV Docetaxel in Study 1.
Figure 6A:
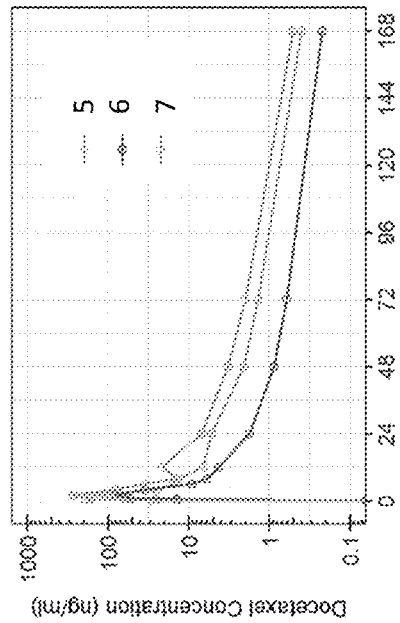
FIGS. 6A-6D are graphs showing the Study 2 oral docetaxel concentration (ng/mL) versus time (hours) by subject per cohort; A) 35 mg/m$^2$ oral docetaxel (cohort 1); B) 75 mg/m$^2$ oral docetaxel (cohort 2); C) 150 mg/m$^2$ oral docetaxel (cohort 3); D) 225 mg/m$^2$ oral docetaxel (cohort 4).
Figure 6B:
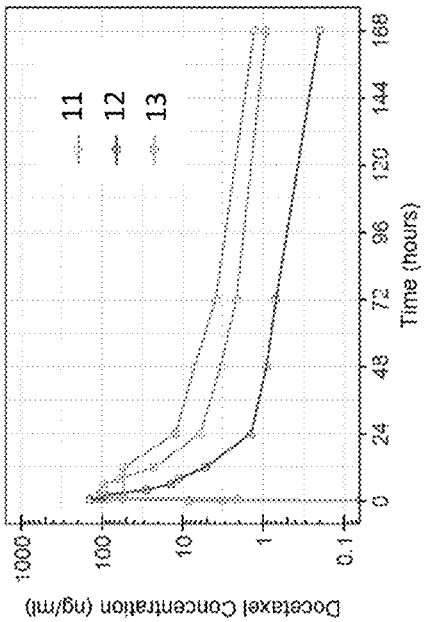
Figure 6C:
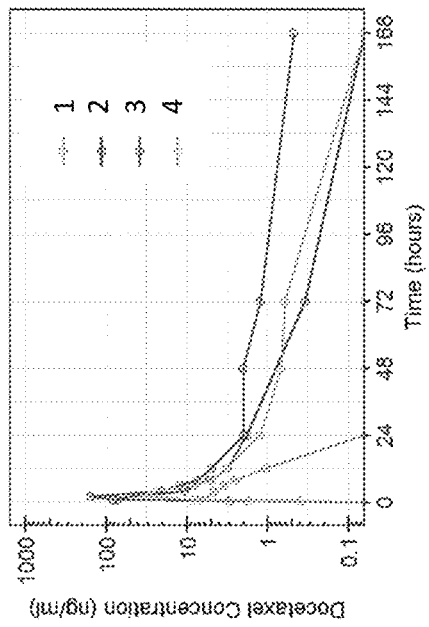
Figure 6D:
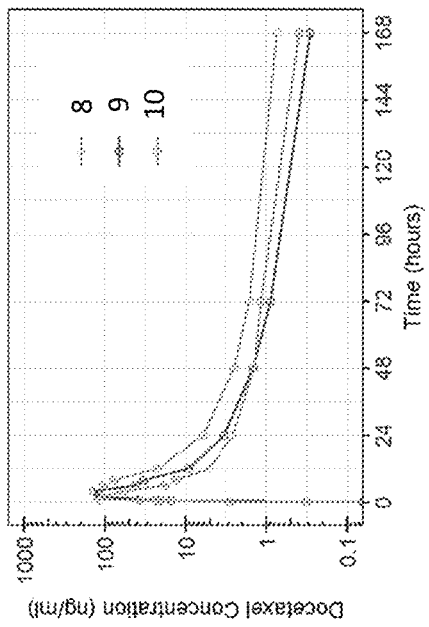
Figure 7:
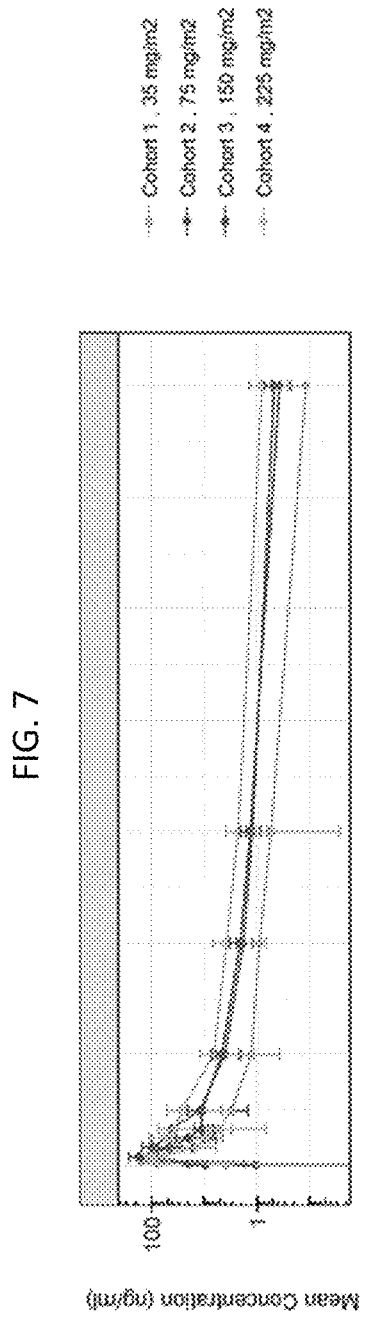
FIG. 7 is a graph showing the comparison of increasing oral docetaxel concentration with increasing dose by cohort (Study 2).
Figure 8:
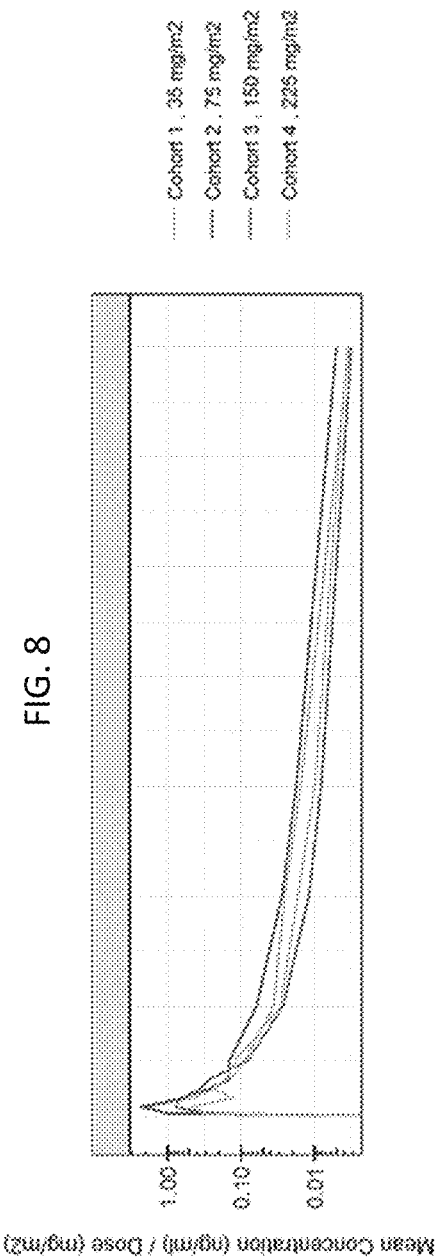
FIG. 8 is a graph showing the comparison of increasing docetaxel concentration with increasing dose (35 mg/m$^2$, 75 mg/m$^2$, 150 mg/m$^2$, 225 mg/m$^2$) by cohort, dose normalized (Study 2).
Figure 9:
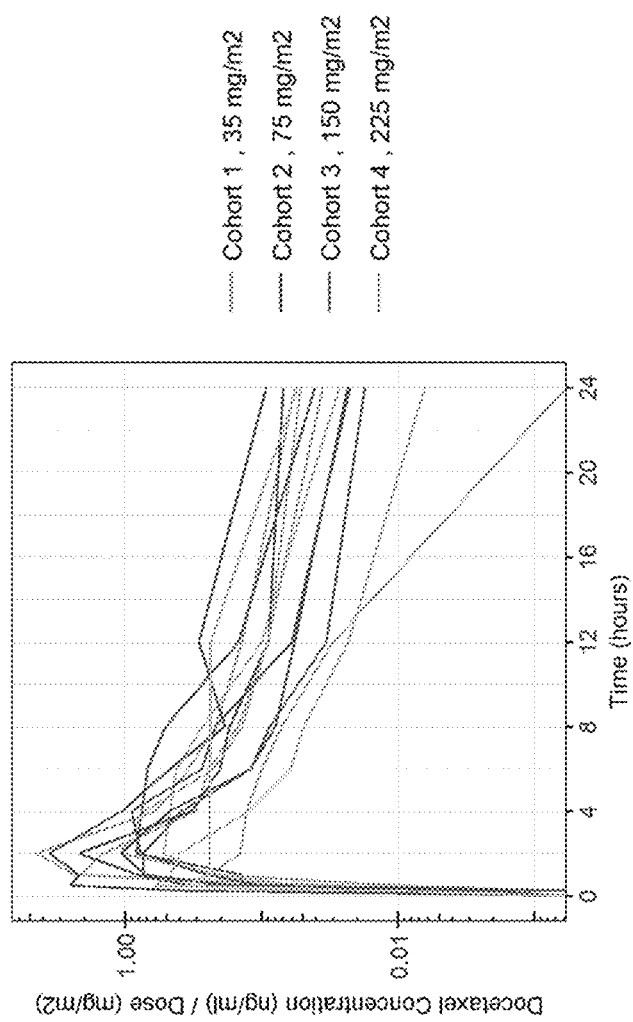
FIG. 9 is a graph showing the comparison of dose normalized docetaxel concentration (ng/mL)/dose (mg/m$^2$) versus time (hours), grouped by subject and cohort from 0-24 hours (Study 2).
Figure 10:
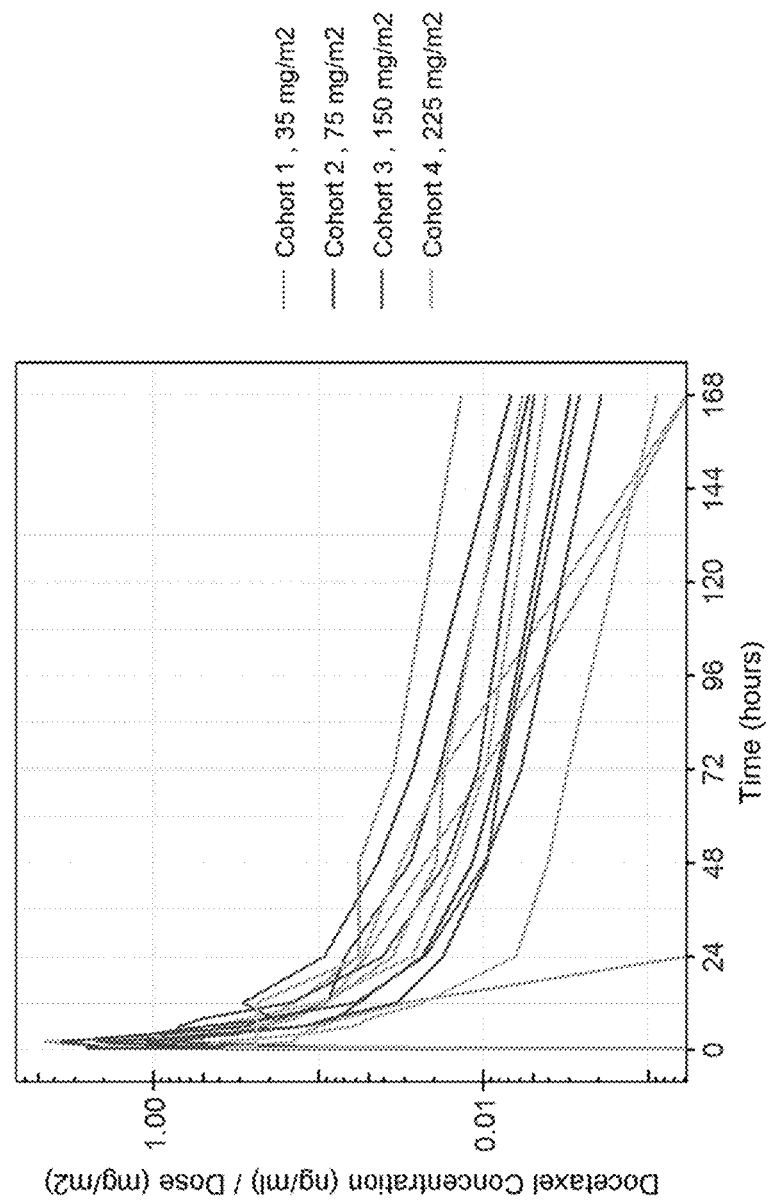
FIG. 10 is a graph showing the comparison of dose normalized docetaxel concentration (ng/mL)/dose (mg/m$^2$) versus time (hours), grouped by subject and cohort from 0-168 hours (Study 2).
Figure 11B:
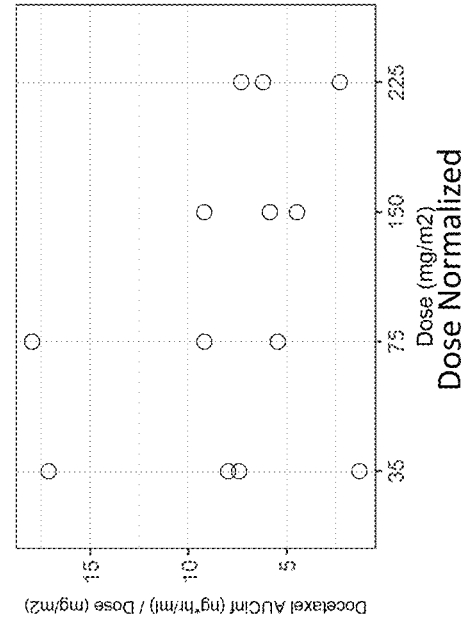
FIGS. 11A-11B are graphs showing the comparison of oral docetaxel AUC$_{inf}$ (ng*hr/mL) versus dose (mg/m$^2$); A) AUC$_{inf}$ versus dose and B) AUC$_{inf}$ versus dose, dose normalized (Study 2).
Figure 11A:
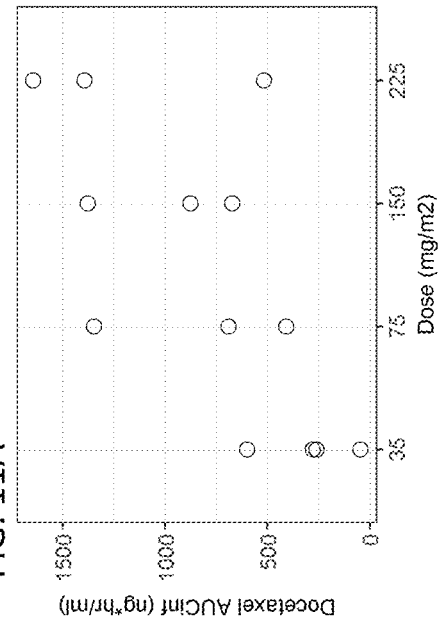
Figure 12B:
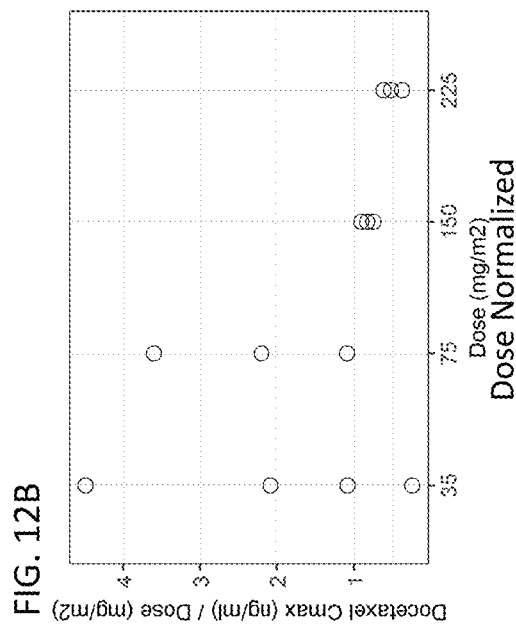
FIGS. 12A-12B are graphs showing the comparison of oral docetaxel C$_{max}$ (ng/mL) versus dose (mg/m$^2$); A) C$_{max}$ versus dose and B) C$_{max}$ versus dose, dose normalized (Study 2).
Figure 12A:
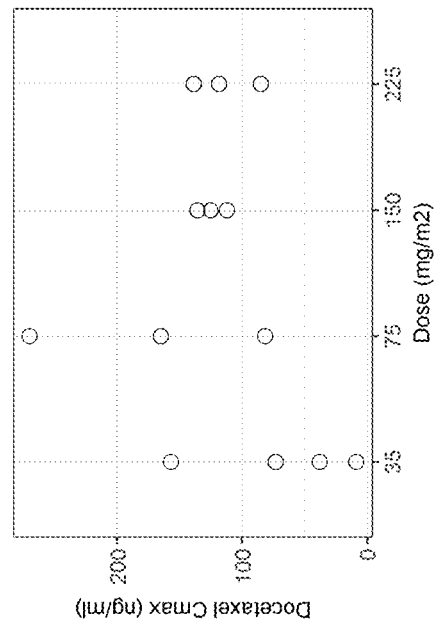

The area under the curve from 0 to 24 hours ($AUC_{0-24}$) was higher for IV administration in comparison to oral dosage. Docetaxel plasma concentrations showed an increase with IV dose (35, 75 mg/m$^2$). The dose normalized AUC for IV and oral dosage was 27.17 (ng*hr/mL) and 23.33 (ng*hr/mL), respectively. The half-life ($t_{1/2}$) for oral docetaxel was 21.3 h, comparable to that of IV docetaxel at 21.9 h. The results are shown in Table 1 and in FIGS. 1 and 2. Additional pharmacokinetic IV versus oral dosage comparison is shown in Tables 2 and 3 and FIGS. 4 and 5.

TABLE 1

Oral and IV docetaxel pharmacokinetics

| Dose (mg/m$^2$) | No. of patients | Length of infusion (h) | $C_{max}$ (ng/mL) | $AUC_{0-24}$ (ng*hr/mL) | Dose Normalized AUC | $t_{1/2}$ (h) |
|---|---|---|---|---|---|---|
| 60 mg/m$^2$ IV | 3 | 1 | 1310 (21.1%) (276) | 1630 (19.2%) (313) | 27.17 | 21.9 |
| 75 mg/m$^2$ Oral | 3 | NA | 103 (18.7%) (19.3) | 329 (4.0%) (13.1) | 23.33 | 21.3 |

TABLE 2

Pharmacokinetics summary of oral docetaxel ($C_{max}$, $T_{max}$, $t_{1/2}$)

| | $C_{max}$ (ng/mL) | | $T_{max}$ | | $t_{1/2}$ (hr$^{-1}$) | |
|---|---|---|---|---|---|---|
| Subject | Oral docetaxel | IV docetaxel | Oral docetaxel | IV docetaxel | Oral docetaxel | IV docetaxel |
| 1 | 85.60 | 1573.42 | 2.00 | 1.00 | 16.51 | 16.82 |
| 3 | 99.49 | 1324.69 | 2.50 | 0.98 | 20.99 | 21.65 |
| 4 | 123.64 | 1022.69 | 1.00 | 0.67 | 25.80 | 22.03 |
| Mean | 102.91 | 1306.93 | 1.83 | 0.88 | 21.10 | 20.17 |
| SD | 19.25 | 275.79 | 0.76 | 0.19 | 4.65 | 2.91 |
| CV % | 18.71 | 21.10 | 41.66 | 21.26 | 22.02 | 14.41 |
| Mean % | 7.87 | | 207.55 | | 104.60 | |
| Max | 123.64 | 1573.42 | 2.50 | 1.00 | 25.08 | 22.03 |
| Min | 85.60 | 1022.69 | 1.00 | 0.67 | 16.51 | 16.82 |

The mean $C_{max}$ for oral and IV docetaxel showed 102.91 and 1306.93 ng/mL, respectively. Oral docetaxel showed a maximum $C_{max}$ of 123.64 and a minimum of 85.60 ng/mL. IV docetaxel showed a maximum $C_{max}$ of 1573.42 and a minimum of 1022.69 ng/mL. The mean $T_{max}$ for oral and IV docetaxel showed 1.83 and 0.88 hr, respectively. Oral docetaxel showed a maximum $T_{max}$ of 2.50 and a minimum of 1.00 hr. IV docetaxel showed a maximum $T_{max}$ of 1.00 and a minimum of 0.67 hr. The mean $t_{1/2}$ for oral and IV docetaxel showed 21.10 and 20.17 hr$^{-1}$, respectively. Oral docetaxel showed a maximum $t_{1/2}$ of 25.08 and a minimum of 16.51 hr$^{-1}$. IV docetaxel showed a maximum $t_{1/2}$ of 22.03 and a minimum of 16.82 hr$^{-1}$. The results are shown in Table 2.

TABLE 3

PK summary of oral docetaxel ($AUC_{0-t}$, $AUC_{0-inf}$, Absolute Bioavailability)

| | $AUC_{0-t}$ (ng*hr/mL) | | $AUC_{0-inf}$ (ng*hr/mL) | | Absolute Bioavailability (%) |
|---|---|---|---|---|---|
| Subject | Oral docetaxel | IV docetaxel | Oral docetaxel | IV docetaxel | |
| 1 | 339.37 | 2226.82 | 402.64 | 2291.49 | 12.30 |
| 3 | 361.10 | 1741.59 | 442.31 | 1822.04 | 17.80 |
| 4 | 484.69 | 1714.69 | 589.65 | 1801.79 | 25.09 |
| Mean | 395.05 | 1894.37 | 478.20 | 1971.77 | 18.40 |
| SD | 78.38 | 288.23 | 98.54 | 277.06 | 6.42 |
| CV % | 19.84 | 15.21 | 20.61 | 14.05 | 34.87 |
| Mean % | 20.85 | | 24.25 | | |
| Max | 484.69 | 2226.82 | 589.65 | 2291.49 | 25.09 |
| Min | 339.37 | 1714.69 | 402.64 | 1801.79 | 12.30 |

The mean $AUC_{0-t}$ for oral and IV docetaxel showed 395.02 and 1894.37 ng*hr/mL, respectively. Oral docetaxel showed a maximum $AUC_{0-t}$ of 484.69 and a minimum of 339.37 ng*hr/mL. IV docetaxel showed a maximum $AUC_{0-t}$ of 2226.82 and a minimum of 1714.69 ng*hr/mL. The mean $AUC_{0-inf}$ for oral and IV docetaxel showed 478.20 and 1971.77 ng*hr/mL, respectively. Oral docetaxel showed a maximum $AUC_{0-inf}$ of 589.65 and a minimum of 402.64 ng*hr/mL. IV docetaxel showed a maximum $AUC_{0-inf}$ of 2291.49 and a minimum of 1801.79 ng*hr/mL. The mean absolute bioavailability showed 18.40%, with a maximum of 25.09% and a minimum of 12.30%. The results are shown in Table 3.

Example 2—Clinical Study of Orally Administered Docetaxel in Combination with Compound A—Dosage Investigation of Solid Tumors A 2-part study was conducted in subjects with solid tumors ("Study 2"). The initial stage included a 21-day 3+3 dose escalation to maximum tolerated dose (MTD) of oral docetaxel, at a starting dose of 35 mg/m$^2$. The dose levels increased to 75 mg/m$^2$, 150 mg/m$^2$, 225 mg/m$^2$, 300 mg/m$^2$, 375 mg/m$^2$, and 400 mg/m$^2$. In the second part of this study, half of the group starting at a selected dose from stage 1, was given over two consecutive days every three weeks. A total of 15 (n=40) subjects enrolled in this study.

Pharmacokinetic results from the 2 studies showed that the maximum concentration $C_{max}$ value for 35 mg/m$^2$, 75 mg/m$^2$, and 150 mg/m$^2$ doses were 69.1 ng/mL, 172 ng/mL, and 124 ng/mL, respectively. The area under the curve from 0 to 24 hours ($AUC_{0-24}$) increased with dosage increase with 263 ng*hr/mL for 35 mg/m$^2$ oral docetaxel, 598 ng*hr/mL for 75 mg/m$^2$ oral docetaxel, and 753 ng*hr/mL for 150 mg/m$^2$ oral docetaxel. The dose normalized AUC decreased with increase of oral dosage of oral docetaxel from 39.97 to 26.70 from 35 mg/m$^2$ to 150 mg/m$^2$, respectively. The half-life ($t_{1/2}$) for oral dosed oral docetaxel increased with increased dosage from 29.2 h to 53.1 h to 62.8 h, respectively for 35 mg/m$^2$, 75 mg/m$^2$, and 150 mg/m$^2$. The differences in half-life for these studies can be attributed to different sampling schedules. The results are shown in Tables 4 and 5, as well as in FIGS. 1 and 2.

TABLE 4

Oral docetaxel pharmacokinetics across a dosage range

| Dose (mg/m²) | No. of patients | Length of infusion (h) | $C_{max}$ (ng/mL) | $AUC_{0-24}$ (ng*hr/mL) | Dose Normalized AUC | $t_{1/2}$ (h) |
|---|---|---|---|---|---|---|
| 35 mg/m² Oral | 4 | NA | 69.1 (92.9%) (64.2) | 263 (43.7%) (115) | 39.97 | 29.2 |
| 75 mg/m² Oral | 3 | NA | 172 (54.8%) (94.4) | 598 (63.9%) (382) | 38.23 | 53.1 |
| 150 mg/m² Oral | 5 | NA | 124 (9.66%) (12.0) | 753 (37.4%) (306) | 26.70 | 62.8 |

TABLE 5

Docetaxel pharmacokinetics summary

| Dose (mg) | | $C_{max}$ (ng/mL) | $T_{max}$ (hr) | $AUC_{0-24}$ (hr*ng/mL) | $AUC_{last}$ (hr*ng/mL) | $AUC_{inf\_obs}$ (hr*ng/mL) | $t_{1/2}$ (hr) | $AUC\ \%_{Extrap\_obs}$ (%) | $R_{sq\_adjusted}$ |
|---|---|---|---|---|---|---|---|---|---|
| 35 | N | 4 | 4 | 4 | 4 | 4 | 4 | 4 | 4 |
|    | Mean | 69.1 | 1.50 | 211 | 276 | 296 | 27.6 | 7.51 | 0.975 |
|    | CV % | 92.9 | 38.5 | 67.8 | 76.8 | 77.2 | 95.7 | 43.8 | 2.17 |
| 75 | N | 3 | 3 | 3 | 3 | 3 | 3 | 3 | . |
|    | Mean | 172 | 2.00 | 598 | 788 | 815 | 53.1 | 3.89 | 0.993 |
|    | CV % | 54.8 | 0.00 | 63.9 | 60.4 | 59.1 | 15.6 | 31.8 | 0.303 |
| 150 | N | 3 | 3 | 3 | 3 | 3 | 3 | 3 | 3 |
|    | Mean | 124 | 2.67 | 753 | 931 | 976 | 62.8 | 4.48 | 0.969 |
|    | CV % | 9.66 | 43.3 | 37.2 | 36.4 | 37.3 | 15.0 | 37.8 | 3.01 |
| 225 | N | 3 | 3 | 3 | 3 | 3 | 3 | 3 | 3 |
|    | Mean | 114 | 1.00 | 792 | 1120 | 1190 | 56.0 | 4.93 | 0.964 |
|    | CV % | 24.0 | 86.6 | 41.2 | 49.3 | 50.0 | 19.1 | 35.2 | 3.17 |

Docetaxel pharmacokinetics increase with dose. The area under the curve extrapolated to infinity ($AUC_{inf}$) shows an increase with the increase of dose. PK data indicates that oral docetaxel exposure increases with dose and that exposure similar to that achieved with IV dosing is feasible with 1 or 2 days of dosing every three week.

Individual and cohort pharmacokinetic data is shown in Tables 11 and 12, and FIGS. 6-12B.

Example 3—A Comparison of Pharmacokinetic Properties of Oral Administration of Docetaxel in Combination with Compound A Studies (Study 1 and Study 2)

IV docetaxel plasma concentrations increase with dose. Oral docetaxel has similar PK profiles across both studies. The results are shown in Tables 6 and 7.

TABLE 6

Summary of Docetaxel PK Parameters

| Study | Route | Dose (mg/m²) | $C_{max}$ (ng/ml) | $AUC_{0-inf}$ (ng*hr/mL) |
|---|---|---|---|---|
| Study 1 | IV | 60 N = 3 | 131 (21.1%) | 1920 (13.2%) |
|  | Oral | 75 N = 3 | 103 (18.7%) | 476 (20.8%) |
| Study 2 | Oral | 35 N = 4 | 69.1 (92.9%) | 308 (90.4%) (N = 3) |
|  |  | 75 N = 3 | 172 (54.8%) | 756 (50.9%) |
|  |  | 150 N = 3 | 124 (9.66%) | 976 (37.3%) |

TABLE 7

Study 1 and Study 2 Comparison Stratified by Cancer Diagnosis

| Study | Dose (mg/m²) | Screening # | Subject # | Cancer Diagnosis | $C_{max}$ (ng/mL) | $AUC_{0-24}$ (ng*hr/mL) |
|---|---|---|---|---|---|---|
| Study 2 | 35 | 001-S001 | 001-101 | Lung |  | ND |
|  | 35 | 001-S003 | 001-102 | Breast | 73.0 | 227 |
|  | 35 | 001-S004 | 001-103 | Esophagus | 157 | 392 |
|  |  | 001-S007 | N/A | Lung |  |  |
|  | 35 | 002-S001 | 002-104 | Urothelial | 38.0 | 170 |
|  |  | 002-S002 | N/A | Urothelial |  |  |
|  | 75 | 001-S006 | 001-201 | Pancreatic | 165 | 461 |
|  |  | 002-S003 | N/A | Cervix |  |  |
|  | 75 | 002-S004 | 002-203 | Ovarian | 81.6 | 304 |
|  | 75 | 002-S005 | 003-203 | Ovarian |  |  |
|  | 75 | 003-S001 | 003-202 | IVC high grade leiomyosarcoma | 190 | 1030 |

TABLE 7-continued

Study 1 and Study 2 Comparison Stratified by Cancer Diagnosis

| Study | Dose (mg/m²) | Screening # | Subject # | Cancer Diagnosis | $C_{max}$ (ng/mL) | $AUC_{0-24}$ (ng*hr/mL) |
|---|---|---|---|---|---|---|
| | 150 | 001-S008 | 001-302 | Pancreas | 125 | 1050 |
| | 150 | 002-S007 | 002-303 | Endometrium | 136 | 720 |
| | 150 | 003-S002 | 003-301 | Neck of Pancreas | 112 | 490 |
| Study 1 | 60 (IV) | | 1 | Prostate | 1570 | 1970 |
| | 60 (IV) | | 3 | | 1320 | 1570 |
| | 60 (IV) | | 4 | | 1020 | 1350 |
| | 75 | | 1 | | 85.6 | 313 |
| | 75 | | 3 | | 99.5 | 336 |
| | 75 | | 4 | | 124 | 336 |

In Study 1, all subjects had a diagnosis of prostate cancer. An oral dosage of 75 mg/m² showed a $C_{max}$ in the range of 85.6-124 ng/mL and an $AUC_{0-24}$ of 313-336 ng*hr/mL. An IV dosage of 60 mg/m² showed a $C_{max}$ in the range of 1020-1570 ng/mL and an $AUC_{0-24}$ of 1350-1970 ng*hr/mL.

In Study 2, the cancers diagnoses included lung, breast, esophagus, lung, urothelial, pancreatic, cervix, ovarian, and IVC high grade leiomyosarcoma. An oral dosage of 75 mg/m² showed a $C_{max}$ in the range of 81.6-190 ng/mL and an $AUC_{0-24}$ of 304-1030 ng*hr/mL, varied by cancer diagnosis. An oral dosage of 35 mg/m² showed a $C_{max}$ in the range of 38.0-157 ng/mL and an $AUC_{0-24}$ of 170-392 ng*hr/mL, varied by cancer diagnosis. An oral dosage of 150 mg/m² showed a $C_{max}$ in the range of 112-136 ng/mL and an $AUC_{0-24}$ of 490-1050 ng*hr/mL, varied by cancer diagnosis. The results are shown in Table 4.

Table 8 shows the half life comparison between Study 1 oral docetaxel and IV docetaxel. Additionally, Table 8 shows the comparison of half life for Study 2 across a range of doses. Both IV and oral docetaxel of study 1 show comparable reported half-lives.

TABLE 8

Half-life comparison of Study 1 and 2

| Study | LLOQ | Dose regimen | PK Sampling | Reported half-life |
|---|---|---|---|---|
| 1 | NA | 75 mg/m² (oral) | Predose, 0.25, 0.5, 0.75, 1, 1.25, 1.5, 2, 2.5, 3, 3.5, 4, 5, 6, 8, 12, 18, 24, 32, 48, 56, 72, 96 | 75 mg/m²: 16.4, 21.4, 26.0 h |
| | | 60 mg/m² (iv) | Predose, 2, 5, 8, 12, 20, 40, 60 min during infusion, 0.25, 0.5, 0.75, 1, 2, 3, 4, 6, 8, 12, 18, 24, 32, 48, 56, 72 hours post infusion | 60 mg/m²: 17.4, 18.4, 30.1 h |
| 2 | 0.2 ng/mL | 35 mg/m² | Predose docetaxel, 0.25, 0.5, 1, 2, 4, 6, 8, 12, 24, 48, 72, 168 (docetaxel sampling points) | 35 mg/m²: 3.4 h, 19.1 h, 65.3 h |
| | | 75 mg/m² | | 75 mg/m²: 51.4 h, 62.4 h, 45.8 h |
| | | 150 mg/m² | | 150 mg/m²: 72.0 h, 53.3 h, 63.3 h |

Table 9 outlines the clinical study protocols for both Study 1 and Study 2.

TABLE 9

Clinical Study Protocol

| | Study 1 | Study 2 |
|---|---|---|
| Inclusion Criteria | Men only | Men and Women (currently, mostly women are enrolled) |
| Cancer Diagnosis | Metastatic Prostate Cancer only | Any advanced solid malignancies |
| Permissible ConMeds | Steroids are allowed | Steroids are restricted to only specific cases |
| PK Sampling time points | Predose Docetaxel, 0.25, 0.5, 0.75, 1, 1.25, 1.5, 2, 2.5, 3, 3.5, 4, 5, 6, 8, 12, 18, 24, 32, 48, 56, 72, 96 | Predose HM30181A, Predose Docetaxel, 0.25, 0.5, 1, 2, 4, 6, 8, 12, 24, 48, 72, 168, 336 (HM only), 504 (HM only) |
| Pre-medication | Per PI discretion | Restricted to specific cases |
| Inclusion criteria for HGB | ≥90 g/L (9 g/dL) | ≥10 g/dL |
| Fasting requirements | 8 hours before and 4 hours after dosing | 6 hours before and 2 hours after dosing |

TABLE 9-continued

| | Clinical Study Protocol | |
|---|---|---|
| | Study 1 | Study 2 |
| Caffeine/Alcohol | Restricted for 3 days and 12 hours, respectively | Not restricted |
| Water intake with dosing | Not restricted | Restricted to less than 240 mL |

Example 4—Target Concentration of Orally Administered Docetaxel

A target concentration was determined based upon $GI_{50}$ from screening NCI-60 cell lines with docetaxel (NCI-60 cell line screen of Docetaxel; Braakhuis et al. *Anticancer Research* (1994) 14: 205-208; Engblom et al. *Anticancer Research* (1997) 17: 2475-2480; Kelland et al. *Cancer Chemother Pharmacol* (1992) 30: 444-450; Riccardi et al. *Eur J of Cancer* (1995) 31A: 494-499). The $IC_{50}$ range from 0.5 to 5 nM was targeted with corresponding docetaxel plasma concentrations from 0.4 to 4 ng/mL. Individuals administered 35 or 75 mg/m² oral docetaxel surpassed the in vitro target $IC_{50}$ of 5 nM (4 ng/mL), Table 10 shows the standard time above the targeted $IC_{50}$ for each study and dose regimen.

TABLE 10

Time above target $IC_{50}$: comparisons of Study 1 and Study 2

| Dose (mg/m²) | Regimen | Average Time above Target (h) (0 to last time point measured above 4 ng/ml) | Study |
|---|---|---|---|
| 60 | 1 h IV infusion Q3W | 40.9 | 1 |
| 35 | SD | 7.5 | 2 |
| 75 | SD | 20.5 | 1 |
| 75 | SD | 21.5 | 2 |
| 150 | SD | 15.5 | 2 |

The known efficacious monotherapy schedule for mHRPC, was utilized to determine the target AUC for 75 mg/m² over 28 days as 3410+/−980 h*ng/mL (Baker et al 2004, mixed solid tumours). The provided PK data is equivalent in mHRPC. Dosages were extrapolated from Baker et al through targeting desired concentrations from various IV docetaxel regimens, seen in FIG. 3.

Utilizing predicted mean AUC pre cycle from Study 2 to replicate the target AUC over three weeks the oral docetaxel dosage would accordingly be 150 mg/m² dosed for 4 days of a three week schedule or 75 mg/m² dosed for 5 days of a three week schedule. Additionally, the desired AUC may be matched by 225 mg/m² dosed for 2 to 3 days of a three week schedule, or 1 day every three weeks.

Example 5—Oral Docetaxel Exposure

Oral docetaxel was administered twice per week, on consecutive days over a 21 day period. Compound A was administered once before oral administration of docetaxel. Two models of data were presented to predict oral docetaxel AUC versus dose.

NCA Procedure

All subject PK data within the dataset were analyzed using Phoenix 8.0. NCA Model "Plasma (200-202)" with extravascular dose input selected within the software. Individual time points for the terminal slope were automatically selected by the software, and linear up—log down interpolation calculation method was used for the analysis. Individual BLQ samples were set to 0.00 ng/ml for noncompartmental analysis unless the PK sample occurred between two PK samples above the limit of quantification, in which case the PK sample was set to missing. For the calculation of summary statistics and mean concentration figures, all BLQ samples were set to 0.00 ng/ml. If the extrapolated portion of $AUC_{0 \to \infty}$ from time of last measurable plasma concentration to infinity (AUC % extrap) for a subject was greater than 20.0% or the adjusted $R^2$ was less than 0.85, the $AUC_{0 \to \infty}$ dependent parameters were not reported. If $R^2$ was less than 0.85, the $t_{1/2}$ was not reported.

TABLE 11

Study 2 docetaxel individual subject and summary PK parameter data

| Analyte | Dose (mg/m²) | ID | Cmax (ng/mL) | Tmax (hr) | $AUC_{0-12}$ (hr*ng/mL) | $AUC_{0-24}$ (hr*ng/mL) | $AUC_{0-48}$ (hr*ng/mL) | AUClast (hr*ng/mL) | $t_{1/2}$ (hr) | $AUC_{INF\_obs}$ (hr*ng/mL) | CL/F (L/hr/m²) | Vd/F (L/m²) | AUC % $Extrap_{obs}$ (%) | Rsq_adjusted |
|---|---|---|---|---|---|---|---|---|---|---|---|---|---|---|
| Docetaxel | 35 | 1 | 8.59 | 1.00 | 39.8 | 46.1 | 46.1 | 39.8 | 3.40 | 44.9 | 779 | 3820 | 11.4 | 0.992 |
| | | 2 | 73.0 | 1.00 | 198 | 227 | 257 | 270 | 19.1 | 279 | 125 | 3450 | 3.39 | 0.995 |
| | | 3 | 157 | 2.00 | 353 | 392 | 440 | 554 | 65.3 | 599 | 58.4 | 5500 | 7.45 | 0.954 |
| | | 4 | 38.0 | 2.00 | 145 | 178 | 218 | 239 | 22.8 | 259 | 135 | 4440 | 7.76 | 0.961 |
| N | | | 4 | 4 | 4 | 4 | 4 | 4 | 4 | 4 | 4 | 4 | 4 | 4 |
| Mean | | | 69.1 | 1.50 | 184 | 211 | 240 | 276 | 27.6 | 296 | 274 | 4300 | 7.51 | 0.975 |
| CV % | | | 92.9 | 38.5 | 70.8 | 67.8 | 67.2 | 76.8 | 95.7 | 77.2 | 123 | 20.9 | 43.8 | 2.17 |
| Docetaxel | 75 | 5 | 165 | 2.00 | 390 | 461 | 543 | 660 | 51.4 | 690 | 109 | 8060 | 4.31 | 0.996 |
| | | 6 | 81.6 | 2.00 | 270 | 304 | 334 | 389 | 62.1 | 409 | 183 | 16400 | 4.87 | 0.992 |
| | | 7 | 270 | 2.00 | 875 | 1030 | 1150 | 1310 | 45.8 | 1350 | 55.7 | 3680 | 2.50 | 0.990 |
| N | | | 3 | 3 | 3 | 3 | 3 | 3 | 3 | 3 | 3 | 3 | 3 | 3 |
| Mean | | | 172 | 2.00 | 512 | 598 | 675 | 788 | 53.1 | 815 | 116 | 9390 | 3.89 | 0.993 |
| CV % | | | 54.8 | 0.00 | 62.6 | 63.9 | 62.6 | 60.4 | 15.6 | 59.1 | 55.4 | 69.0 | 31.8 | 0.303 |
| Docetaxel | 150 | 8 | 125 | 2.00 | 898 | 1050 | 1150 | 1300 | 72.0 | 1380 | 109 | 11300 | 5.59 | 0.938 |
| | | 9 | 136 | 4.00 | 650 | 720 | 775 | 854 | 53.2 | 876 | 171 | 13100 | 2.53 | 0.973 |
| | | 10 | 112 | 2.00 | 446 | 490 | 538 | 637 | 63.3 | 673 | 223 | 20300 | 5.32 | 0.996 |

TABLE 11-continued

Study 2 docetaxel individual subject and summary PK parameter data

| Analyte | Dose (mg/m²) | ID | Cmax (ng/mL) | Tmax (hr) | AUC$_{0-12}$ (hr*ng/mL) | AUC$_{0-24}$ (hr*ng/mL) | AUC$_{0-48}$ (hr*ng/mL) | AUClast (hr*ng/mL) | $t_{1/2}$ (hr) | AUC$_{INF\_obs}$ (hr*ng/mL) | CL/F (L/hr/m²) | Vd/F (L/m²) | AUC % Extrap$_{obs}$ (%) | Rsq_adjusted |
|---|---|---|---|---|---|---|---|---|---|---|---|---|---|---|
| N | | | 3 | 3 | 3 | 3 | 3 | 3 | 3 | 3 | 3 | 3 | 3 | 3 |
| Mean | | | 124 | 2.67 | 665 | 753 | 819 | 931 | 62.8 | 976 | 168 | 14900 | 4.48 | 0.969 |
| CV % | | | 9.66 | 43.3 | 34.1 | 37.2 | 37.4 | 36.4 | 15.0 | 37.3 | 34.1 | 32.0 | 37.8 | 3.01 |
| Docetaxel | 225 | 11 | 118 | 2.00 | 835 | 986 | 1100 | 1300 | 67.3 | 1390 | 161 | 15700 | 6.48 | 0.950 |
| | | 12 | 139 | 0.500 | 380 | 416 | 443 | 501 | 54.4 | 517 | 436 | 34200 | 3.06 | 0.999 |
| | | 13 | 84.7 | 0.500 | 637 | 974 | 1200 | 1560 | 46.1 | 1650 | 137 | 9100 | 5.26 | 0.944 |
| N | | | 3 | 3 | 3 | 3 | 3 | 3 | 3 | 3 | 3 | 3 | 3 | 3 |
| Mean | | | 114 | 1.00 | 618 | 792 | 914 | 1120 | 56.0 | 1190 | 245 | 19700 | 4.93 | 0.964 |
| CV % | | | 24.0 | 86.6 | 36.9 | 41.2 | 45.0 | 49.3 | 19.1 | 50.0 | 67.8 | 66.2 | 35.2 | 3.17 |

TABLE 12

Study 2 docetaxel individual concentration vs time table

| Analyte | Dose (mg/m²) | Cohort | SUBJID | 0.00 | 0.250 | 0.500 | 1.00 | 2.00 | 4.00 | 6.00 | 8.00 | 12.0 | 24.0 | 48.0 | 72.0 | 168 |
|---|---|---|---|---|---|---|---|---|---|---|---|---|---|---|---|---|
| | | | | | | | | Analyte Concentration (ng/ml) | | | | | | | | |
| Docetaxel | 35 | 1 | 1 | BLQ | BLQ | 1.80 | 8.59 | 5.05 | 4.55 | 3.52 | 2.52 | 1.05 | BLQ | BLQ | BLQ | BLQ |
| | | | 2 | BLQ | | | 73.0 | 50.4 | 10.7 | 8.60 | 5.23 | 3.17 | 1.82 | | 0.344 | BLQ |
| | | | 3 | BLQ | BLQ | 2.94 | 82.8 | 157 | 20.8 | 12.1 | 7.66 | 4.92 | 2.00 | 2.02 | 1.23 | 0.474 |
| | | | 4 | BLQ | BLQ | 0.383 | 7.14 | 38.0 | 25.3 | 7.87 | 4.92 | 3.20 | 1.25 | 0.675 | 0.612 | BLQ |
| Docetaxel | 75 | 2 | 5 | BLQ | BLQ | 25.3 | 61.2 | 165 | 24.4 | 15.2 | 12.9 | 6.67 | 5.22 | 2.08 | 1.39 | 0.401 |
| | | | 6 | BLQ | BLQ | 13.7 | 52.8 | 81.6 | 35.3 | 9.07 | 5.99 | 4.32 | 1.75 | 0.872 | 0.612 | 0.222 |
| | | | 7 | BLQ | 28.0 | 190 | 164 | 270 | 79.5 | 35.7 | 14.0 | 21.7 | 6.94 | 3.28 | 1.99 | 0.510 |
| Docetaxel | 150 | 3 | 8 | BLQ | 0.319 | 21.3 | 20.6 | 125 | ALQ | 104 | 76.6 | 22.3 | 6.09 | 2.53 | 1.62 | 0.742 |
| | | | 9 | BLQ | BLQ | 15.1 | 37.6 | 116 | 136 | 41.3 | 32.8 | 9.07 | 3.38 | 1.47 | 0.890 | 0.289 |
| | | | 10 | BLQ | 2.90 | 23.6 | 111 | 112 | 57.9 | 18.0 | 13.1 | 5.05 | 2.63 | 1.43 | 1.17 | 0.392 |
| Docetaxel | 225 | 4 | 11 | BLQ | BLQ | 2.14 | 55.6 | 118 | ALQ | 95.1 | 61.4 | 22.6 | 6.06 | 3.43 | 2.18 | 0.931 |
| | | | 12 | BLQ | 8.40 | 139 | 105 | 90.4 | 28.0 | 13.9 | 11.1 | 5.22 | 1.43 | 0.917 | 0.696 | 0.201 |
| | | | 13 | BLQ | 3.19 | 84.7 | 54.4 | ALQ | ALQ | ALQ | ALQ | 53.2 | 12.4 | 7.17 | 3.90 | 1.30 |

TABLE 13

IV docetaxel pharmacokinetics

| Dose (mg/m²) | No. of patients | Length of infusion (h) | C$_{max}$ (ng/ml) | AUC$_{0-24}$ (ng*hr/mL) | Dose Normalized AUC | $t_{1/2}\gamma$ (h) |
|---|---|---|---|---|---|---|
| 20 (n = 1) | 1 | 1 | | 960 | 48 | 2.2 |
| 20 (n = 1) | 1 | 24 | | 920 | 46 | |
| 30 (n = 2) | 2 | 1.58 (0.80) | 640 (450) | 1260 (340) | 42 | 4.6 (2.8) |
| 40 (n = 1) | 1 | 1 | 420 | 670 | 16.75 | 3.8 |
| 40 (n = 3) | 3 | 24 | | 2190 (2140-2240)* | 54.75 | |
| 55 (n = 3) | 3 | 1.68 (0.75) | 820 (380) | 1420 | 25.82 | 2 |
| 55 (n = 4) | 4 | 24 | | 2560 (1190-3280)* | 46.55 | |
| 70 (n = 2) | 2 | 1.37 (0.53) | 1910 (320) | 2790 (850) | 39.86 | 2.5 (1.4) |
| 70 (n = 3) | 3 | 24 | | 3470 (2900-4510)* | 49.57 | |
| 85 (n = 6) | 6 | 1.61 (0.81) | 2420 (920) | 4100 (920) | 48.24 | 13.6 (6.1) |
| 90 (n = 5) | 5 | 24 | | 7810 (5950-9820)* | 86.78 | |
| 100 (n = 4) | 4 | 2.03 (0.09) | 2410 (250) | 5930 (530) | 59.30 | 18.5 (10.7) |
| 115 (n = 4) | 4 | 1.84 (0.28) | 2680 (930) | 5190 (160) | 45.13 | 9.6 (5.8) |

Example 6—Oral Dosing of Docetaxel Capsules in Combination with HM30181A

Two phase 1 studies were performed to investigate the pharmacokinetics and tolerability of docetaxel capsules administered orally in combination with HM30181A. In a first study, the absolute bioavailability and AUC of oral docetaxel 75 mg/m² (n=3) administered with 15 mg HM30181A was determined. In a second study, the pharmacokinetics of oral docetaxel was determined at doses of 35, 75, 150 and 225 mg/m² in combination with HM30181A 15 mg in groups of 3-6 patients with advanced cancer.

In combination with HM30181A, the docetaxel was rapidly absorbed with mean $T_{max}$ of 3-4 hours. The $C_{max}$ and AUC increased with dose from 35 to 225 mg/m². The AUC for IV (75 mg/m²) and oral (35, 75, 150, and 225 mg/m²)

were 2422, 248, 692, 888, and 1400 ng·hr/mL, respectively. Individual F % ranged between 20-31% at a dose of 75 mg/m$^2$. $C_{max}$ was at 9.5-13% of that observed after IV administration. The terminal phase half-life is approximately 56 hours. Based on non-linear regression analysis, oral administration at 75 mg/m$^2$ for three days or 150 mg/m$^2$ for two days is calculated to achieve similar AUC compared to IV docetaxel (75 mg/m$^2$). Thus, short-term oral administration of docetaxel and HM30181A can achieve a similar AUC with a lower $C_{max}$ compared with IV docetaxel (75 mg/m$^2$), showing promising activity and tolerability for this combination.

EQUIVALENTS

The details of one or more embodiments of the invention are set forth in the accompanying description above. Although any methods and materials similar or equivalent to those described herein can be used in the practice or testing of the present disclosure, the preferred methods and materials are now described. Other features, objects, and advantages of the present disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the invention to the precise form disclosed, but by the claims appended hereto.

The invention claimed is:

1. A method for treating cancer in a subject in need thereof, comprising:
   a. oral administration of docetaxel at an amount of about 15 mg/m$^2$ to about 450 mg/m$^2$ to the subject once a day and for 1-7 times a week; and
   b. oral administration of Compound A:

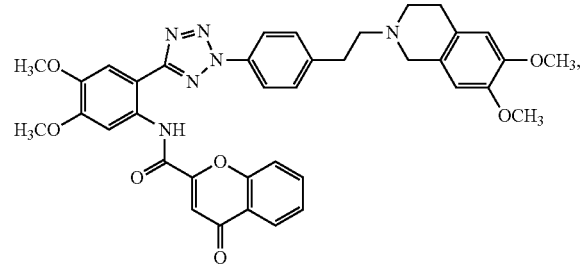 [SMILES: COc1cc2c(cc1OC)CN(CCc1ccc(-n3nnc(-c4cc(OC)c(OC)cc4NC(=O)c4cc(=O)c5ccccc5o4)n3)cc1)CC2]

or a pharmaceutically acceptable salt or solvate thereof, to the subject once a day and for 1-7 times a week, and
   wherein Compound A or a pharmaceutically acceptable salt or solvate thereof is administered simultaneously with or prior to the docetaxel, and wherein the cancer is selected from breast cancer, pancreatic cancer, non-small cell lung cancer, ovarian cancer, esophageal cancer, endometrial cancer, cervical cancer, urothelial cancer, and prostate cancer.

2. A method for reducing hematologic toxicity and/or neurotoxicity, and/or other toxicities or symptoms in a subject suffering from cancer and undergoing docetaxel therapy, comprising:
   a. oral administration of docetaxel at an amount of about 15 mg/m$^2$ to about 450 mg/m$^2$ to the subject once a day and for 1-7 times a week; and
   b. oral administration of Compound A:

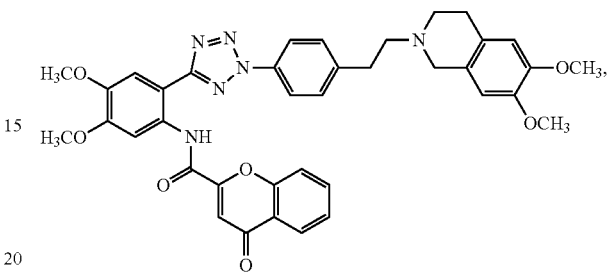

or a pharmaceutically acceptable salt or solvate thereof, to the subject once a day and for 1-7 times a week,
   wherein the plasma exposure of the orally administered docetaxel, as measured by $AUC_{(0\rightarrow\infty)}$, is equal to or greater than the plasma exposure, as measured by $AUC_{(0\rightarrow\infty)}$, of intravenously administered docetaxel at an amount of about 30 mg/m$^2$ to about 100 mg/m$^2$ over a period of about 1 to about 24 hours once every three weeks, once every two weeks, or once every week, and
   wherein Compound A or a pharmaceutically acceptable salt or solvate thereof is administered simultaneously with or prior to the docetaxel.

3. A method for reducing or preventing hypersensitivity-type infusion reactions associated with intravenously administered docetaxel therapy in a subject suffering from cancer, comprising:
   a. oral administration of docetaxel at an amount of about 15 mg/m$^2$ to about 450 mg/m$^2$ to the subject once a day and for 1-7 times a week; and
   b. oral administration of Compound A:

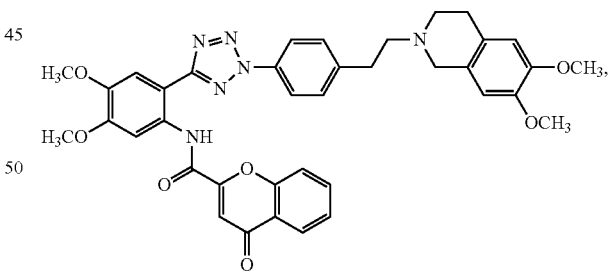

or a pharmaceutically acceptable salt or solvate thereof, to the subject once a day and for 1-7 times a week;
   wherein the orally administered docetaxel reaches therapeutic blood or plasma levels in the subject, and
   wherein Compound A or a pharmaceutically acceptable salt or solvate thereof is administered simultaneously with or prior to the docetaxel.

4. The method of claim 1, wherein the docetaxel is administered as a single dose.

5. The method of claim 1, wherein the docetaxel is administered at an amount of about 75 mg/m$^2$ to about 350 mg/m$^2$.

6. The method of claim 1, wherein the docetaxel is administered at an amount of about 25 mg/m², about 50 mg/m², about 75 mg/m², about 100 mg/m², about 125 mg/m², about 150 mg/m², about 175 mg/m², about 200 mg/m², about 225 mg/m², or about 250 mg/m².

7. The method of claim 1, wherein the docetaxel is administered at least twice per week.

8. The method of claim 1, wherein the plasma exposure of the orally administered docetaxel, as measured by $AUC_{(0\to\infty)}$, is equal to or greater than the plasma exposure of intravenously administered docetaxel at an amount of about 80 mg/m² over a period of about 60 minutes, as measured by $AUC_{(0\to\infty)}$.

9. The method of claim 1, wherein Compound A or a pharmaceutically acceptable salt or solvate thereof and the docetaxel are administered on the same day.

10. The method of claim 1, wherein the subject is suffering from metastatic breast cancer, and wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel at an amount of about 30 mg/m² to about 100 mg/m² over a period of about 1-24 hours once every 1-3 weeks.

11. The method of claim 1, wherein the subject is suffering from non-small cell lung cancer, and wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel at an amount of about 30 mg/m² to about 100 mg/m² over a period of about 1-24 hours once per week for 1-3 weeks.

12. The method of claim 1, wherein the subject is suffering from adenocarcinoma of the pancreas, and wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel at an amount of about 30 mg/m² to about 100 mg/m² over a period of about 1-24 hours once per week for 1-3 weeks.

13. The method of claim 1, wherein the subject is suffering from carcinoma of the ovary, and wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel at an amount of about 30 mg/m² to about 100 mg/m² over a period of about 1-24 hours once every 1-3 weeks.

14. The method of claim 1, wherein the subject is suffering from carcinoma of the breast, and wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel at an amount of about 30 mg/m² to about 100 mg/m² once every 1-3 weeks.

15. The method of claim 1, wherein the subject is suffering from non-small cell lung carcinoma, and wherein the plasma exposure of the orally administered docetaxel, as measured by $AUC_{(0\to\infty)}$, is equal to or greater than the plasma exposure, as measured by $AUC_{(0\to\infty)}$, of intravenously administered docetaxel at an amount of about 30 mg/m² to about 100 mg/m² over a period of about 24 hours once every 1-3 weeks.

16. The method of claim 1, wherein Compound A or a pharmaceutically acceptable salt or solvate thereof is administered orally at an amount of about 15 mg to about 50 mg.

17. The method of claim 1, wherein Compound A or a pharmaceutically acceptable salt or solvate thereof is administered orally at an amount of about 15 mg.

18. The method of claim 1, wherein Compound A or a pharmaceutically acceptable salt or solvate thereof is administered before the docetaxel is administered.

19. The method of claim 1, comprising oral administration of the methanesulfonate monohydrate of

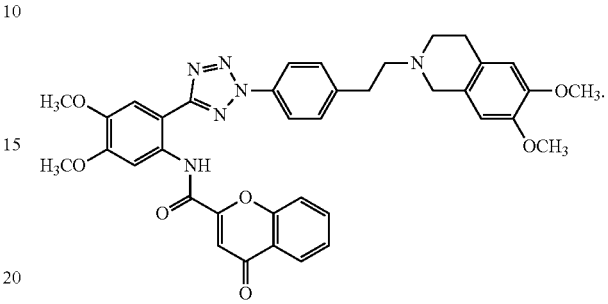

20. The method of claim 1, comprising oral administration of the methanesulfonate monohydrate of

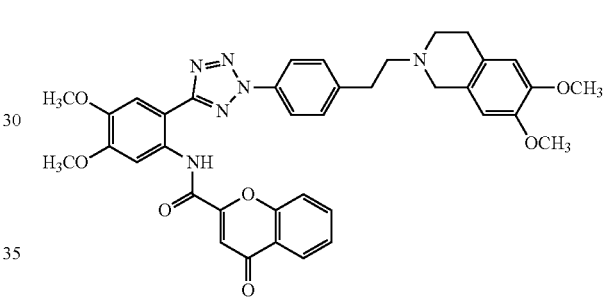

at an amount of about 15 mg.

21. The method of claim 1, wherein the cancer is breast cancer.

22. The method of claim 1, wherein the cancer is pancreatic cancer.

23. The method of claim 1, wherein the cancer is non-small cell lung cancer.

24. The method of claim 1, wherein the cancer is ovarian cancer.

25. The method of claim 1, wherein the cancer is esophageal cancer.

26. The method of claim 1, wherein the cancer is endometrial cancer.

27. The method of claim 1, wherein the cancer is cervical cancer.

28. The method of claim 1, wherein the cancer is urothelial cancer.

29. The method of claim 1, wherein the cancer is prostate cancer.

30. The method of claim 1, comprising oral administration of docetaxel once per week.

31. The method of claim 1, comprising oral administration of docetaxel once over a three-week period.

32. The method of claim 1, comprising oral administration of docetaxel as one single dose over a three-week period.

* * * * *